US011230719B2

(12) United States Patent
Gruber et al.

(10) Patent No.: US 11,230,719 B2
(45) **Date of Patent: *Jan. 25, 2022**

(54) RETROVIRAL VECTOR HAVING IMMUNE-STIMULATING ACTIVITY

(71) Applicant: DENOVO BIOPHARMA LLC, San Diego, CA (US)

(72) Inventors: Harry E. Gruber, Rancho Santa Fe, CA (US); Douglas J. Jolly, Encinitas, CA (US); Amy H. Lin, San Diego, CA (US); Joan M. Robbins, San Diego, CA (US); Derek G. Ostertag, San Diego, CA (US)

(73) Assignee: DENOVO BIOPHARMA LLC, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/127,388

(22) PCT Filed: Mar. 25, 2015

(86) PCT No.: PCT/US2015/022512

§ 371 (c)(1),
(2) Date: Sep. 19, 2016

(87) PCT Pub. No.: WO2015/148683

PCT Pub. Date: Oct. 1, 2015

(65) Prior Publication Data

US 2017/0175137 A1 Jun. 22, 2017

Related U.S. Application Data

(60) Provisional application No. 61/970,823, filed on Mar. 26, 2014.

(51) Int. Cl.

| | |
|---|---|
| ***C12N 15/86*** | (2006.01) |
| ***A61K 38/20*** | (2006.01) |
| ***A61K 38/21*** | (2006.01) |
| ***C12N 15/113*** | (2010.01) |
| ***A61K 35/76*** | (2015.01) |
| ***A61K 31/7088*** | (2006.01) |
| ***A61K 48/00*** | (2006.01) |

(52) U.S. Cl.

CPC .......... *C12N 15/86* (2013.01); *A61K 31/7088* (2013.01); *A61K 35/76* (2013.01); *A61K 38/2013* (2013.01); *A61K 38/217* (2013.01); *A61K 48/005* (2013.01); *C12N 15/113* (2013.01); *C12N 2310/14* (2013.01); *C12N 2310/141* (2013.01); *C12N 2310/531* (2013.01); *C12N 2320/31* (2013.01); *C12N 2330/51* (2013.01); *C12N 2740/13043* (2013.01)

(58) Field of Classification Search

CPC .. C12N 15/86; C12N 15/8636; C12N 15/113; C12N 15/1136; C12N 15/115; C12N 2310/141

See application file for complete search history.

(56) References Cited

U.S. PATENT DOCUMENTS

| | | | |
|---|---|---|---|
| 6,410,313 B1 * | 6/2002 | Kasahara | C12N 15/86 424/93.2 |
| 8,383,796 B2 * | 2/2013 | Korman | C07K 16/28 536/23.1 |
| 8,652,460 B2 | 2/2014 | Kasahara et al. | |
| 8,829,173 B2 | 9/2014 | Gruber et al. | |
| 9,669,049 B2 | 6/2017 | Gruber et al. | |
| 9,732,326 B2 | 8/2017 | Gruber et al. | |
| 10,035,983 B2 | 7/2018 | Gruber et al. | |
| 2005/0002903 A1 | 1/2005 | Kasahara et al. | |
| 2005/0123515 A1 | 6/2005 | Olsen | |
| 2010/0055111 A1 | 3/2010 | Sharma et al. | |
| 2012/0052554 A1 | 3/2012 | Kasahara et al. | |
| 2014/0234958 A1 | 8/2014 | Kasahara et al. | |
| 2015/0273029 A1 * | 10/2015 | Gruber | A61K 48/00 424/133.1 |
| 2016/0222412 A1 | 8/2016 | Lin et al. | |

FOREIGN PATENT DOCUMENTS

| | | |
|---|---|---|
| JP | 2009-201518 | 9/2009 |
| JP | 2010-6730 | 1/2010 |
| WO | 96/02143 A1 | 2/1996 |
| WO | 01/004266 A1 | 1/2001 |
| WO | 2006/127980 A2 | 11/2006 |
| WO | 2010/067882 A1 | 6/2010 |
| WO | 2011/126864 A2 | 10/2011 |
| WO | 2012-021794 A1 | 2/2012 |
| WO | 2013/019906 A1 | 2/2013 |
| WO | 2013/110464 | 8/2013 |
| WO | 2014/016817 | 1/2014 |

OTHER PUBLICATIONS

Zarrin et al. Biochimica et Biophysica Acta 1446:135-139, 1999 (Year: 1999).*

*Leo Pharmaceutical Products, Ltd* v. *Rea* (No. 2012-1520 Fed. Circ. Aug. 12, 2013) (Year: 2013).*

(Continued)

*Primary Examiner* — Marcia S Noble

(74) *Attorney, Agent, or Firm* — Rimon, P.C.

(57) ABSTRACT

The disclosure provides vectors for treating cancers, method of producing such vectors and methods of use of the vectors.

11 Claims, 13 Drawing Sheets

Specification includes a Sequence Listing.

(56) References Cited

OTHER PUBLICATIONS

Young, Lee W., International Search Report and Written Opinion, PCT/US2015/022512, dated Jul. 1, 2015.
Wittmann-Regis, Agnes, International Preliminary Report on Patentability and Written Opinion, PCT/US2015/022512, The International Bureau of WIPO, dated Oct. 6, 2016.
Borkner et al., "RNA interference targeting programmed death receptor-1 improves immune functions of tumor-specific T cells", Cancer Immunology, vol. 59, No. 8, Mar. 27, 2010, pp. 1173-1183.
Liu et al., "Inhibition of TGFbeta1 makes nonimmunogenic tumor cells effective for therapeutic vaccination", Journal of Immunotherapy, vol. 32, No. 3, Apr. 1, 2009, pp. 232-239.
Macagno M et al., "289 Indoleamine 2,3-Dioxygenase (IDO) silencing for improved antitumor vaccination", European Journal of Cancer, vol. 8, No. 5, Jun. 1, 2010, p. 75.
Stitch, David, Extended European Search Report, European Patent Office, Application No. 15769100.7, dated Oct. 11, 2017.
Wei et al., "Silencing of the TGF-[beta]1 Gene Increases the Immunogenicity of Cells from Human Ovarian Carcinoma", Journal of Immunotherapy, vol. 35, No. 3, Apr. 1, 2012, pp. 267-275.
Blache et al., "Systemic Delivery of *Salmonella typhimurium* Transformed with IDO shRNA Enhances Intratumoral Vector Colonization and Suppresses Tumor Growth", Cancer Res., Dec. 15, 2012, 72(24):6447-6456.
Okubo, Tomoyuki, Office Action, Japanese Patent Office, Application No. 2016-558674, dated Jan. 29, 2019.
Perez et al., Design and Selection of Toca 511 for Clinical Use: Modified Retroviral Replicating Vector with Improved Stability and Gene Expression, Molecular Therapy, Sep. 2012, vol. 21, No. 9, pp. 1689-1698.
Sitch, David et al., Summons to Attend Oral Proceedings, European Patent Office, Application No. 15769100.7, Nov. 20, 2018.
Okubo, Tomoyuki, Office Action, Japanese Patent Office, Application No. 2016-558674, dated Nov. 26, 2019.
Requirement for Restriction/Election for U.S. Appl. No. 14/438,564, dated Feb. 11, 2016, 8 pages.
Response to Requirement for Restriction/Election for U.S. Appl. No. 14/438,564, dated Apr. 11, 2016, 2 pages.
Non-Final Rejection for U.S. Appl. No. 14/438,564, dated Jun. 20, 2016, 14 pages.
Response to Non-Final Rejection for U.S. Appl. No. 14/438,564, dated Sep. 19, 2016, 14 pages.
Final Rejection for U.S. Appl. No. 14/438,564, dated May 4, 2017, 16 pages.
Response to Final Rejection for U.S. Appl. No. 14/438,564, dated Aug. 4, 2017, 16 pages.
Advisory Action for U.S. Appl. No. 14/438,564, dated Aug. 23, 2017, 3 pages.
Appeal Brief for U.S. Appl. No. 14/438,564, dated Apr. 5, 2018, 36 pages.
Examiner's Answer to Appeal Brief for U.S. Appl. No. 14/438,564, dated Aug. 8, 2018, 23 pages.
Reply Brief for U.S. Appl. No. 14/438,564, dated Oct. 8, 2018, 17 pages.
Patent Board Decision—Examiner Reversed for U.S. Appl. No. 14/438,564, dated Mar. 16, 2020, 17 pages.
Response to the Decision of the Board of the Patent Trial and Appeal Board for U.S. Appl. No. 14/438,564, dated May 18, 2020, 12 pages.
Non-Final Rejection for U.S. Appl. No. 14/438,564, dated Sep. 4, 2020, 12 pages.
Response to Non-Final Rejection for U.S. Appl. No. 14/438,564, dated Mar. 1, 2021, 12 pages.
Examiner Interview Summary Record for U.S. Appl. No. 14/438,564, dated Apr. 6, 2021, 1 page.
Notice of Allowance and Fee(s) Due for U.S. Appl. No. 14/438,564, dated Apr. 6, 2021, 10 pages.
International Search Report for international patent application PCT/US2013/066709 (WO2014066700), dated Jan. 28, 2014, 5 pages.
Written Opinion of The International Searching Authority for international patent application PCT/US2013/066709 (WO2014066700), dated Jan. 28, 2014, 8 pages.
International Preliminary Report on Patentability for international patent application PCT/US2013/066709 (WO2014066700), dated Apr. 28, 2015, 9 pages.
Papadakis, et al., "Promoters and Control Elements: Designing Expression Cassettes for Gene Therapy," Current Gene Therapy 4:89-113 (2004).
Zhao-Emonet et al., "T Cell-specific expression from MoMLV retroviral vectors containing a CD4 min-promoter/enhancer," J Gene Med 2000;2:416-425.

* cited by examiner pAC3-miR pri-miR pAC3-H1-shRNA H1 pre-miR pAC3-yCD2-H1-shRNAmiR H1 pre-miR 205 bp pAC3-scAB-H1-shRNAmiR H1 pre-miR 205 bp P = reference plasmid DNA for each vector 1. RSV- IDO1miR30shRNA2
2. RSV-yCD2-IDO1miR30shRNA2
3. RSV-yCD2-U6-IDO1miR30shRNA2
4. U6-IDO1miR30EshRNA2
5. H1-IDO1miR30shRNA2
6. U6-IDO1miR21shRNA2
7. U6-IDO1miR155shRNA2
8. RSV- PDL1miR30shRNA4
9. RSV-yCD2-PDL1miR30shRNA4
10. RSV-yCD2-U6-PDL1miR30shRNA4
11. U6-PDL1miR30EshRNA4
12. H1-PDL1miR30shRNA2
13. U6-PDL1miR21shRNA2
14. U6-PDL1miR155shRNA2

RRV-RSV-PDL1miR30shRNA

3/3

SEQUENCE LISTING

```
<160> NUMBER OF SEQ ID NOS: 33

<210> SEQ ID NO 1
<211> LENGTH: 11892
<212> TYPE: DNA
<213> ORGANISM: Artificial Sequence
<220> FEATURE:
<223> OTHER INFORMATION: Vector pAC3-yCD2

<400> SEQUENCE: 1

tagttattaa tagtaatcaa ttacggggtc attagttcat agcccatata tggagttccg      60

cgttacataa cttacggtaa atggcccgcc tggctgaccg cccaacgacc cccgcccatt     120

gacgtcaata atgacgtatg ttcccatagt aacgccaata gggactttcc attgacgtca     180

atgggtggag tatttacggt aaactgccca cttggcagta catcaagtgt atcatatgcc     240

aagtacgccc cctattgacg tcaatgacgg taaatggccc gcctggcatt atgcccagta     300

catgacctta tgggactttc ctacttggca gtacatctac gtattagtca tcgctattac     360

catggtgatg cggttttggc agtacatcaa tgggcgtgga tagcggtttg actcacgggg     420

atttccaagt ctccacccca ttgacgtcaa tgggagtttg ttttggcacc aaaatcaacg     480

ggactttcca aaatgtcgta acaactccgc cccattgacg caaatgggcg gtaggcgtgt     540

acggtgggag gtctatataa gcagagctgg tttagtgaac cggcgccagt cctccgattg     600

actgagtcgc ccgggtaccc gtgtatccaa taaaccctct tgcagttgca tccgacttgt     660

ggtctcgctg ttccttggga gggtctcctc tgagtgattg actacccgtc agcgggggtc     720

tttcatttgg gggctcgtcc gggatcggga gacccctgcc cagggaccac cgacccacca     780

ccgggaggta agctggccag caacttatct gtgtctgtcc gattgtctag tgtctatgac     840

tgattttatg cgcctgcgtc ggtactagtt agctaactag ctctgtatct ggcggacccg     900

tggtggaact gacgagttcg gaacacccgg ccgcaaccct gggagacgtc ccagggactt     960

cgggggccgt ttttgtggcc cgacctgagt ccaaaaatcc cgatcgtttt ggactctttg    1020

gtgcaccccc cttagaggag ggatatgtgg ttctggtagg agacgagaac ctaaaacagt    1080

tcccgcctcc gtctgaattt ttgctttcgg tttgggaccg aagccgcgcc gcgcgtcttg    1140

tctgctgcag catcgttctg tgttgtctct gtctgactgt gtttctgtat ttgtctgaga    1200

atatgggcca gactgttacc actcccttaa gtttgacctt aggtcactgg aaagatgtcg    1260
```

```
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc cccccttgaac  1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgttc   1980
tcatcaccca tcagcccacc tggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag catcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
```

```
accccaccag tcagcctctc ttcgcctttg agtggagaga tccagagatg ggaatctcag   3720

gacaattgac ctggaccaga ctcccacagg gtttcaaaaa cagtcccacc ctgtttgatg   3780

aggcactgca cagagaccta gcagacttcc ggatccagca cccagacttg atcctgctac   3840

agtacgtgga tgacttactg ctggccgcca cttctgagct agactgccaa caaggtactc   3900

gggccctgtt acaaacccta gggaacctcg ggtatcgggc ctcggccaag aaagcccaaa   3960

tttgccagaa acaggtcaag tatctggggt atcttctaaa agagggtcag agatggctga   4020

ctgaggccag aaaagagact gtgatggggc agcctactcc gaagacccct cgacaactaa   4080

gggagttcct agggacggca ggcttctgtc gcctctggat ccctgggttt gcagaaatgg   4140

cagcccccct gtaccctctc accaaaacgg ggactctgtt taattggggc ccagaccaac   4200

aaaaggccta tcaagaaatc aagcaagctc ttctaactgc cccagccctg ggggttgccag   4260

atttgactaa gccctttgaa ctctttgtcg acgagaagca gggctacgcc aaaggtgtcc   4320

taacgcaaaa actgggacct tggcgtcggc cggtggccta cctgtccaaa aagctagacc   4380

cagtagcagc tgggtggccc ccttgcctac ggatggtagc agccattgcc gtactgacaa   4440

aggatgcagg caagctaacc atgggacagc cactagtcat tctggccccc catgcagtag   4500

aggcactagt caaacaaccc cccgaccgct ggctttccaa cgcccggatg actcactatc   4560

aggccttgct tttggacacg gaccgggtcc agttcggacc ggtggtagcc ctgaacccgg   4620

ctacgctgct cccactgcct gaggaagggc tgcaacacaa ctgccttgat atcctggccg   4680

aagcccacgg aacccgaccc gacctaacgg accagccgct cccagacgcc gaccacacct   4740

ggtacacgga tggaagcagt ctcttacaag agggacagcg taaggcggga gctgcggtga   4800

ccaccgagac cgaggtaatc tgggctaaag ccctgccagc cgggacatcc gctcagcggg   4860

ctgaactgat agcactcacc caggccctaa agatggcaga aggtaagaag ctaaatgttt   4920

atactgatag ccgttatgct tttgctactg cccatatcca tggagaaata tacagaaggc   4980

gtgggttgct cacatcagaa ggcaaagaga tcaaaaataa agacgagatc ttggccctac   5040

taaaagccct ctttctgccc aaaagactta gcataatcca ttgtccagga catcaaaagg   5100

gacacagcgc cgaggctaga ggcaaccgga tggctgacca agcggcccga aaggcagcca   5160

tcacagagac tccagacacc tctaccctcc tcatagaaaa ttcatcaccc tacacctcag   5220

aacattttca ttacacagtg actgatataa aggacctaac caagttgggg gccatttatg   5280

ataaaacaaa gaagtattgg gtctaccaag gaaaacctgt gatgcctgac cagtttactt   5340

ttgaattatt agactttctt catcagctga ctcacctcag cttctcaaaa atgaaggctc   5400

tcctagagag aagccacagt ccctactaca tgctgaaccg ggatcgaaca ctcaaaaata   5460

tcactgagac ctgcaaagct tgtgcacaag tcaacgccag caagtctgcc gttaaacagg   5520

gaactagggt ccgcgggcat cggcccggca ctcattggga gatcgatttc accgagataa   5580

agcccggatt gtatggctat aaatatcttc tagtttttat agatacccttt tctggctgga   5640

tagaagcctt cccaaccaag aaagaaaccg ccaaggtcgt aaccaagaag ctactagagg   5700

agatcttccc caggttcggc atgcctcagg tattgggaac tgacaatggg cctgccttcg   5760

tctccaaggt gagtcagaca gtggccgatc tgttggggat tgattggaaa ttacattgtg   5820

catacagacc ccaaagctca ggccaggtag aaagaatgaa tagaaccatc aaggagactt   5880

taactaaatt aacgcttgca actggctcta gagactgggt gctcctactc cccttagccc   5940

tgtaccgagc ccgcaacacg ccgggccccc atggcctcac cccatatgag atcttatatg   6000
```

```
gggcaccccc gcccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca cccccctggga   6840
cacgggatgc tctaaagttg cctgtggccc ctgctacgac ctctccaaag tatccaattc   6900
cttccaaggg gctactcgag gggggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagccccct caataccagt tacccccctt ccactaccag   7200
tacaccctca acctccccta caagtccaag tgtcccacag ccacccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtt actggccgaa   8340
gccgcttgga ataaggccgg tgtgcgtttg tctatatgtt attttccacc atattgccgt   8400
```

```
cttttggcaa tgtgagggcc cggaaacctg gccctgtctt cttgacgagc attcctaggg   8460
gtctttcccc tctcgccaaa ggaatgcaag gtctgttgaa tgtcgtgaag gaagcagttc   8520
ctctggaagc ttcttgaaga caaacaacgt ctgtagcgac cctttgcagg cagcggaacc   8580
ccccacctgg cgacaggtgc ctctgcggcc aaaagccacg tgtataagat acacctgcaa   8640
aggcggcaca accccagtgc cacgttgtga gttggatagt tgtggaaaga gtcaaatggc   8700
tctcctcaag cgtattcaac aaggggctga aggatgccca gaaggtaccc cattgtatgg   8760
gatctgatct ggggcctcgg tgcacatgct ttacatgtgt ttagtcgagg ttaaaaaaac   8820
gtctaggccc cccgaaccac ggggacgtgg ttttcctttg aaaaacacga ttataaatgg   8880
tgaccggcgg catggcctcc aagtgggatc aaaagggcat ggatatcgct tacgaggagg   8940
ccctgctggg ctacaaggag ggcggcgtgc ctatcggcgg ctgtctgatc aacaacaagg   9000
acggcagtgt gctgggcagg ggccacaaca tgaggttcca gaagggctcc gccaccctgc   9060
acggcgagat ctccaccctg gagaactgtg gcaggctgga gggcaaggtg tacaaggaca   9120
ccaccctgta caccaccctg tccccttgtg acatgtgtac cggcgctatc atcatgtacg   9180
gcatccctag gtgtgtgatc ggcgagaacg tgaacttcaa gtccaagggc gagaagtacc   9240
tgcaaaccag gggccacgag gtggtggttg ttgacgatga gaggtgtaag aagctgatga   9300
agcagttcat cgacgagagg cctcaggact ggttcgagga tatcggcgag taagcggccg   9360
cagataaaat aaaagatttt atttagtctc cagaaaaagg ggggaatgaa agaccccacc   9420
tgtaggtttg gcaagctagc ttaagtaacg ccattttgca aggcatggaa aaatacataa   9480
ctgagaatag agaagttcag atcaaggtca ggaacagatg gaacagctga atatgggcca   9540
aacaggatat ctgtggtaag cagttcctgc cccggctcag ggccaagaac agatggaaca   9600
gctgaatatg ggccaaacag gatatctgtg gtaagcagtt cctgccccgg ctcagggcca   9660
agaacagatg gtccccagat gcggtccagc cctcagcagt ttctagagaa ccatcagatg   9720
tttccagggt gccccaagga cctgaaatga ccctgtgcct tatttgaact aaccaatcag   9780
ttcgcttctc gcttctgttc gcgcgcttct gctccccgag ctcaataaaa gagcccacaa   9840
cccctcactc ggggcgccag tcctccgatt gactgagtcg cccgggtacc cgtgtatcca   9900
ataaaccctc ttgcagttgc atccgacttg tggtctcgct gttccttggg agggtctcct   9960
ctgagtgatt gactacccgt cagcgggggt ctttcattac atgtgagcaa aaggccagca  10020
aaaggccagg aaccgtaaaa aggccgcgtt gctggcgttt ttccataggc tccgcccccc  10080
tgacgagcat cacaaaaatc gacgctcaag tcagaggtgg cgaaacccga caggactata  10140
aagataccag gcgtttcccc ctggaagctc cctcgtgcgc tctcctgttc cgaccctgcc  10200
gcttaccgga tacctgtccg cctttctccc ttcgggaagc gtggcgcttt ctcaatgctc  10260
acgctgtagg tatctcagtt cggtgtaggt cgttcgctcc aagctgggct gtgtgcacga  10320
accccccgtt cagcccgacc gctgcgcctt atccggtaac tatcgtcttg agtccaaccc  10380
ggtaagacac gacttatcgc cactggcagc agccactggt aacaggatta gcagagcgag  10440
gtatgtaggc ggtgctacag agttcttgaa gtggtggcct aactacggct acactagaag  10500
gacagtattt ggtatctgcg ctctgctgaa gccagttacc ttcggaaaaa gagttggtag  10560
ctcttgatcc ggcaaacaaa ccaccgctgg tagcggtggt ttttttgttt gcaagcagca  10620
gattacgcgc agaaaaaaag gatctcaaga agatcctttg atcttttcta cggggtctga  10680
cgctcagtgg aacgaaaact cacgttaagg gattttggtc atgagattat caaaaaggat  10740
```

cttcacctag atccttttaa attaaaaatg aagttttaaa tcaatctaaa gtatatatga 10800
gtaaacttgg tctgacagtt accaatgctt aatcagtgag gcacctatct cagcgatctg 10860
tctatttcgt tcatccatag ttgcctgact ccccgtcgtg tagataacta cgatacggga 10920
gggcttacca tctggcccca gtgctgcaat gataccgcga gacccacgct caccggctcc 10980
agatttatca gcaataaacc agccagccgg aagggccgag cgcagaagtg gtcctgcaac 11040
tttatccgcc tccatccagt ctattaattg ttgccgggaa gctagagtaa gtagttcgcc 11100
agttaatagt ttgcgcaacg ttgttgccat tgctgcaggc atcgtggtgt cacgctcgtc 11160
gtttggtatg gcttcattca gctccggttc ccaacgatca aggcgagtta catgatcccc 11220
catgttgtgc aaaaaagcgg ttagctcctt cggtcctccg atcgttgtca gaagtaagtt 11280
ggccgcagtg ttatcactca tggttatggc agcactgcat aattctctta ctgtcatgcc 11340
atccgtaaga tgcttttctg tgactggtga gtactcaacc aagtcattct gagaatagtg 11400
tatgcggcga ccgagttgct cttgcccggc gtcaacacgg gataataccg cgccacatag 11460
cagaacttta aaagtgctca tcattggaaa acgttcttcg gggcgaaaac tctcaaggat 11520
cttaccgctg ttgagatcca gttcgatgta acccactcgt gcacccaact gatcttcagc 11580
atcttttact ttcaccagcg tttctgggtg agcaaaaaca ggaaggcaaa atgccgcaaa 11640
aaagggaata agggcgacac ggaaatgttg aatactcata ctcttccttt ttcaatatta 11700
ttgaagcatt tatcagggtt attgtctcat gagcggatac atatttgaat gtatttagaa 11760
aaataaacaa ataggggttc cgcgcacatt tccccgaaaa gtgccacctg acgtctaaga 11820
aaccattatt atcatgacat taacctataa aaataggcgt atcacgaggc cctttcgtct 11880
tcaagaattc at 11892

<210> SEQ ID NO 2
<211> LENGTH: 19
<212> TYPE: DNA
<213> ORGANISM: Artificial Sequence
<220> FEATURE:
<223> OTHER INFORMATION: MLV-U3-B Primer

<400> SEQUENCE: 2
agcccacaac ccctcactc 19

<210> SEQ ID NO 3
<211> LENGTH: 18
<212> TYPE: DNA
<213> ORGANISM: Artificial Sequence
<220> FEATURE:
<223> OTHER INFORMATION: MLV-Psi Primer

<400> SEQUENCE: 3
tctcccgatc ccggacga 18

<210> SEQ ID NO 4
<211> LENGTH: 26
<212> TYPE: DNA
<213> ORGANISM: Artificial Sequence
<220> FEATURE:
<223> OTHER INFORMATION: Probe

<400> SEQUENCE: 4
ccccaaatga aagacccccg ctgacg 26

<210> SEQ ID NO 5
<211> LENGTH: 23

<212> TYPE: DNA
<213> ORGANISM: Artificial Sequence
<220> FEATURE:
<223> OTHER INFORMATION: 3' Env primer

<400> SEQUENCE: 5
ctgatcttac tctttggacc ttg 23

<210> SEQ ID NO 6
<211> LENGTH: 24
<212> TYPE: DNA
<213> ORGANISM: Artificial Sequence
<220> FEATURE:
<223> OTHER INFORMATION: 3' UTR Primer

<400> SEQUENCE: 6 ccccttttc tggagactaa ataa 24

<210> SEQ ID NO 7
<211> LENGTH: 11489
<212> TYPE: DNA
<213> ORGANISM: Artificial Sequence
<220> FEATURE:
<223> OTHER INFORMATION: Vector pAC3-H1-IDO1miR30shRNA2

<400> SEQUENCE: 7
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440

-continued

```
tcccctacat cgtgacctgg gaagccttgg cttttgaccc ccctccctgg gtcaagccct   1500
ttgtacaccc taagcctccg cctcctcttc ctccatccgc cccgtctctc cccttgaac    1560
ctcctcgttc gaccccgcct cgatcctccc tttatccagc cctcactcct tctctaggcg   1620
ccaaacctaa acctcaagtt ctttctgaca gtgggggcc gctcatcgac ctacttacag    1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc gggggggcaac   2880
ccgtcacctt cctggtagat actggggccc aacactccgt gctgacccaa aatcctggac   2940
ccctaagtga taagtctgcc tgggtccaag gggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
```

```
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc ccccagccctg gggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
```

-continued

```
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc ccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc    6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagcccccct caataccagt taccccccctt ccactaccag   7200
tacaccctca acctcccta caagtccaag tgtcccacag ccacccccag gaactggaga    7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtg aacgctgacg   8340
tcatcaaccc gctccaagga atcgcgggcc cagtgtcact aggcgggaac acccagcgcg   8400
cgtgcgccct ggcaggaaga tggctgtgag ggacagggga gtggcgccct gcaatatttg   8460
catgtcgcta tgtgttctgg gaaatcacca taaacgtgaa atgtctttgg atttgggaat   8520
cttataagtt ctgtatgaga ccactctttc ccggatcctg ctcgcttcgg cagcacatat   8580
```

```
actagtcgac tagggataac agggtaattg tttgaatgag gcttcagtac tttacagaat   8640
cgttgcctgc acatcttgga aacacttgct gggattactt cttcaggtta acccaacaga   8700
aggctcgaga aggtatattg ctgttgacag tgagcgacac gatcatgtga acccaaatag   8760
tgaagccaca gatgtatttg ggttcacatg atcgtggtgc ctactgcctc ggaattcaag   8820
gggctacttt aggagcaatt atcttgttta ctaaaactga ataccttgct atctctttga   8880
tacattttta caaagctgaa ttaaaatggt ataaattaaa tcactttttt caattggaag   8940
actaatgcgg cggccgcaga taaaataaaa gattttattt agtctccaga aaaagggggg   9000
aatgaaagac cccacctgta ggtttggcaa gctagcttaa gtaacgccat tttgcaaggc   9060
atggaaaaat acataactga gaatagagaa gttcagatca aggtcaggaa cagatggaac   9120
agctgaatat gggccaaaca ggatatctgt ggtaagcagt tcctgccccg gctcagggcc   9180
aagaacagat ggaacagctg aatatgggcc aaacaggata tctgtggtaa gcagttcctg   9240
ccccggctca gggccaagaa cagatggtcc ccagatgcgg tccagccctc agcagtttct   9300
agagaaccat cagatgtttc cagggtgccc caaggacctg aaatgaccct gtgccttatt   9360
tgaactaacc aatcagttcg cttctcgctt ctgttcgcgc gcttctgctc cccgagctca   9420
ataaaagagc ccacaacccc tcactcgggg cgccagtcct ccgattgact gagtcgcccg   9480
ggtacccgtg tatccaataa accctcttgc agttgcatcc gacttgtggt ctcgctgttc   9540
cttgggaggg tctcctctga gtgattgact acccgtcagc gggggtcttt cattacatgt   9600
gagcaaaagg ccagcaaaag gccaggaacc gtaaaaaggc cgcgttgctg gcgtttttcc   9660
ataggctccg cccccctgac gagcatcaca aaaatcgacg ctcaagtcag aggtggcgaa   9720
acccgacagg actataaaga taccaggcgt ttccccctgg aagctccctc gtgcgctctc   9780
ctgttccgac cctgccgctt accggatacc tgtccgcctt tctcccttcg ggaagcgtgg   9840
cgctttctca tagctcacgc tgtaggtatc tcagttcggt gtaggtcgtt cgctccaagc   9900
tgggctgtgt gcacgaaccc cccgttcagc ccgaccgctg cgccttatcc ggtaactatc   9960
gtcttgagtc caacccggta agacacgact tatcgccact ggcagcagcc actggtaaca  10020
ggattagcag agcgaggtat gtaggcggtg ctacagagtt cttgaagtgg tggcctaact  10080
acggctacac tagaaggaca gtatttggta tctgcgctct gctgaagcca gttaccttcg  10140
gaaaaagagt tggtagctct tgatccggca aacaaaccac cgctggtagc ggtggttttt  10200
ttgtttgcaa gcagcagatt acgcgcagaa aaaaaggatc tcaagaagat cctttgatct  10260
tttctacggg gtctgacgct cagtggaacg aaaactcacg ttaagggatt ttggtcatga  10320
gattatcaaa aaggatcttc acctagatcc ttttaaatta aaaatgaagt tttaaatcaa  10380
tctaaagtat atatgagtaa acttggtctg acagttacca atgcttaatc agtgaggcac  10440
ctatctcagc gatctgtcta tttcgttcat ccatagttgc ctgactcccc gtcgtgtaga  10500
taactacgat acgggagggc ttaccatctg gccccagtgc tgcaatgata ccgcgagacc  10560
cacgctcacc ggctccagat ttatcagcaa taaaccagcc agccggaagg gccgagcgca  10620
gaagtggtcc tgcaacttta tccgcctcca tccagtctat taattgttgc cgggaagcta  10680
gagtaagtag ttcgccagtt aatagtttgc gcaacgttgt tgccattgct gcaggcatcg  10740
tggtgtcacg ctcgtcgttt ggtatggctt cattcagctc cggttcccaa cgatcaaggc  10800
gagttacatg atcccccatg ttgtgcaaaa aagcggttag ctccttcggt cctccgatcg  10860
ttgtcagaag taagttggcc gcagtgttat cactcatggt tatggcagca ctgcataatt  10920
```

```
ctcttactgt catgccatcc gtaagatgct tttctgtgac tggtgagtac tcaaccaagt  10980

cattctgaga atagtgtatg cggcgaccga gttgctcttg cccggcgtca acacgggata  11040

ataccgcgcc acatagcaga actttaaaag tgctcatcat tggaaaacgt tcttcggggc  11100

gaaaactctc aaggatctta ccgctgttga gatccagttc gatgtaaccc actcgtgcac  11160

ccaactgatc ttcagcatct tttactttca ccagcgtttc tgggtgagca aaaacaggaa  11220

ggcaaaatgc cgcaaaaaag ggaataaggg cgacacggaa atgttgaata ctcatactct  11280

tcctttttca atattattga agcatttatc agggttattg tctcatgagc ggatacatat  11340

ttgaatgtat ttagaaaaat aaacaaatag gggttccgcg cacatttccc cgaaaagtgc  11400

cacctgacgt ctaagaaacc attattatca tgacattaac ctataaaaat aggcgtatca  11460

cgaggccctt tcgtcttcaa gaattccat                                   11489
```

<210> SEQ ID NO 8
<211> LENGTH: 11526
<212> TYPE: DNA
<213> ORGANISM: Artificial Sequence
<220> FEATURE:
<223> OTHER INFORMATION: Vector pAC3-U6-IDO1miRshRNA2

<400> SEQUENCE: 8

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cggcgccagt cctccgattg    600

actgagtcgc ccgggtaccc gtgtatccaa taaaccctct tgcagttgca tccgacttgt    660

ggtctcgctg ttccttggga gggtctcctc tgagtgattg actacccgtc agcgggggtc    720

tttcatttgg gggctcgtcc gggatcggga gacccctgcc cagggaccac cgacccacca    780

ccgggaggta agctggccag caacttatct gtgtctgtcc gattgtctag tgtctatgac    840

tgattttatg cgcctgcgtc ggtactagtt agctaactag ctctgtatct ggcggacccg    900

tggtggaact gacgagttcg gaacacccgg ccgcaaccct gggagacgtc ccagggactt    960

cgggggccgt ttttgtggcc cgacctgagt ccaaaaatcc cgatcgtttt ggactctttg   1020

gtgcaccccc cttagaggag ggatatgtgg ttctggtagg agacgagaac ctaaaacagt   1080

tcccgcctcc gtctgaattt ttgctttcgg tttgggaccg aagccgcgcc gcgcgtcttg   1140

tctgctgcag catcgttctg tgttgtctct gtctgactgt gtttctgtat ttgtctgaaa   1200

atatgggcca gactgttacc actcccttaa gtttgacctt aggtcactgg aaagatgtcg   1260

agcggatcgc tcacaaccag tcggtagatg tcaagaagag acgttgggtt accttctgct   1320

ctgcagaatg gccaaccttt aacgtcggat ggccgcgaga cggcaccttt aaccgagacc   1380

tcatcaccca ggttaagatc aaggtctttt cacctggccc gcatggacac ccagaccagg   1440

tcccctacat cgtgacctgg gaagccttgg cttttgaccc ccctccctgg gtcaagccct   1500
```

```
ttgtacaccc taagcctccg cctcctcttc ctccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtgggggggcc gctcatcgac ctacttacag   1680
aagacccccc gccttatagg gacccaagac caccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
```

-continued

```
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc ccccagccctg gggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
```

```
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagcccct caataccagt taccccctt ccactaccag   7200
tacaccctca acctccccta caagtccaag tgtcccacag ccacccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta aggtcgggca   8340
ggaagagggc ctatttccca tgattccttc atatttgcat atacgataca aggctgttag   8400
agagataatt agaattaatt tgactgtaaa cacaaagata ttagtacaaa atacgtgacg   8460
tagaaagtaa taatttcttg ggtagtttgc agtttttaaa attatgtttt aaaatggact   8520
atcatatgct taccgtaact tgaaagtatt tcgatttctt ggctttatat atcttgtgga   8580
```

```
aaggacgaaa caccgtgctc gcttcggcag cacatatact agtcgactag ggataacagg   8640
gtaattgttt gaatgaggct tcagtacttt acagaatcgt tgcctgcaca tcttggaaac   8700
acttgctggg attacttctt caggttaacc caacagaagg ctcgagaagg tatattgctg   8760
ttgacagtga gcgacacgat catgtgaacc caaatagtga agccacagat gtatttgggt   8820
tcacatgatc gtggtgccta ctgcctcgga attcaagggg ctactttagg agcaattatc   8880
ttgtttacta aaactgaata ccttgctatc tctttgatac atttttacaa agctgaatta   8940
aaatggtata aattaaatca ctttttttcaa ttggaagact aatgcggcgg ccgcagataa   9000
aataaaagat tttatttagt ctccagaaaa aggggggaat gaaagacccc acctgtaggt   9060
ttggcaagct agcttaagta acgccatttt gcaaggcatg gaaaaataca taactgagaa   9120
tagagaagtt cagatcaagg tcaggaacag atggaacagc tgaatatggg ccaaacagga   9180
tatctgtggt aagcagttcc tgccccggct cagggccaag aacagatgga acagctgaat   9240
atgggccaaa caggatatct gtggtaagca gttcctgccc cggctcaggg ccaagaacag   9300
atggtcccca gatgcggtcc agccctcagc agtttctaga gaaccatcag atgtttccag   9360
ggtgccccaa ggacctgaaa tgaccctgtg ccttatttga actaaccaat cagttcgctt   9420
ctcgcttctg ttcgcgcgct tctgctcccc gagctcaata aaagagccca caacccctca   9480
ctcggggcgc cagtcctccg attgactgag tcgcccgggt acccgtgtat ccaataaacc   9540
ctcttgcagt tgcatccgac ttgtggtctc gctgttcctt gggagggtct cctctgagtg   9600
attgactacc cgtcagcggg ggtctttcat tacatgtgag caaaaggcca gcaaaaggcc   9660
aggaaccgta aaaaggccgc gttgctggcg tttttccata ggctccgccc ccctgacgag   9720
catcacaaaa atcgacgctc aagtcagagg tggcgaaacc cgacaggact ataaagatac   9780
caggcgtttc cccctggaag ctccctcgtg cgctctcctg ttccgaccct gccgcttacc   9840
ggatacctgt ccgcctttct cccttcggga agcgtggcgc tttctcatag ctcacgctgt   9900
aggtatctca gttcggtgta ggtcgttcgc tccaagctgg gctgtgtgca cgaacccccc   9960
gttcagcccg accgctgcgc cttatccggt aactatcgtc ttgagtccaa cccggtaaga  10020
cacgacttat cgccactggc agcagccact ggtaacagga ttagcagagc gaggtatgta  10080
ggcggtgcta cagagttctt gaagtggtgg cctaactacg gctacactag aaggacagta  10140
tttggtatct gcgctctgct gaagccagtt accttcggaa aaagagttgg tagctcttga  10200
tccggcaaac aaaccaccgc tggtagcggt ggtttttttg tttgcaagca gcagattacg  10260
cgcagaaaaa aaggatctca agaagatcct ttgatctttt ctacggggtc tgacgctcag  10320
tggaacgaaa actcacgtta agggattttg gtcatgagat tatcaaaaag gatcttcacc  10380
tagatccttt taaattaaaa atgaagtttt aaatcaatct aaagtatata tgagtaaact  10440
tggtctgaca gttaccaatg cttaatcagt gaggcaccta tctcagcgat ctgtctattt  10500
cgttcatcca tagttgcctg actccccgtc gtgtagataa ctacgatacg ggagggctta  10560
ccatctggcc ccagtgctgc aatgataccg cgagacccac gctcaccggc tccagattta  10620
tcagcaataa accagccagc cggaagggcc gagcgcagaa gtggtcctgc aactttatcc  10680
gcctccatcc agtctattaa ttgttgccgg gaagctagag taagtagttc gccagttaat  10740
agtttgcgca acgttgttgc cattgctgca ggcatcgtgg tgtcacgctc gtcgtttggt  10800
atggcttcat tcagctccgg ttcccaacga tcaaggcgag ttacatgatc ccccatgttg  10860
tgcaaaaaag cggttagctc cttcggtcct ccgatcgttg tcagaagtaa gttggccgca  10920
gtgttatcac tcatggttat ggcagcactg cataattctc ttactgtcat gccatccgta  10980
```

```
agatgctttt ctgtgactgg tgagtactca accaagtcat tctgagaata gtgtatgcgg  11040

cgaccgagtt gctcttgccc ggcgtcaaca cgggataata ccgcgccaca tagcagaact  11100

ttaaaagtgc tcatcattgg aaaacgttct tcggggcgaa aactctcaag gatcttaccg  11160

ctgttgagat ccagttcgat gtaacccact cgtgcaccca actgatcttc agcatctttt  11220

actttcacca gcgtttctgg gtgagcaaaa acaggaaggc aaaatgccgc aaaaaaggga  11280

ataagggcga cacggaaatg ttgaatactc atactcttcc tttttcaata ttattgaagc  11340

atttatcagg gttattgtct catgagcgga tacatatttg aatgtattta gaaaaataaa  11400

caaatagggg ttccgcgcac atttccccga aaagtgccac ctgacgtcta agaaaccatt  11460

attatcatga cattaaccta taaaaatagg cgtatcacga ggccctttcg tcttcaagaa  11520

ttccat                                                             11526
```

<210> SEQ ID NO 9
<211> LENGTH: 11528
<212> TYPE: DNA
<213> ORGANISM: Artificial Sequence
<220> FEATURE:
<223> OTHER INFORMATION: Vector pAC3-RSV-IDO1miR30shRNA2

<400> SEQUENCE: 9

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cggcgccagt cctccgattg    600

actgagtcgc ccgggtaccc gtgtatccaa taaaccctct tgcagttgca tccgacttgt    660

ggtctcgctg ttccttggga gggtctcctc tgagtgattg actacccgtc agcgggggtc    720

tttcatttgg gggctcgtcc gggatcggga gacccctgcc cagggaccac cgacccacca    780

ccgggaggta agctggccag caacttatct gtgtctgtcc gattgtctag tgtctatgac    840

tgattttatg cgcctgcgtc ggtactagtt agctaactag ctctgtatct ggcggacccg    900

tggtggaact gacgagttcg gaacacccgg ccgcaaccct gggagacgtc ccagggactt    960

cgggggccgt ttttgtggcc cgacctgagt ccaaaaatcc cgatcgtttt ggactctttg   1020

gtgcaccccc cttagaggag ggatatgtgg ttctggtagg agacgagaac ctaaaacagt   1080

tcccgcctcc gtctgaattt ttgctttcgg tttgggaccg aagccgcgcc gcgcgtcttg   1140

tctgctgcag catcgttctg tgttgtctct gtctgactgt gtttctgtat ttgtctgaaa   1200

atatgggcca gactgttacc actcccttaa gtttgacctt aggtcactgg aaagatgtcg   1260

agcggatcgc tcacaaccag tcggtagatg tcaagaagag acgttgggtt accttctgct   1320

ctgcagaatg gccaaccttt aacgtcggat ggccgcgaga cggcaccttt aaccgagacc   1380

tcatcaccca ggttaagatc aaggtctttt cacctggccc gcatggacac ccagaccagg   1440
```

-continued

```
tcccctacat cgtgacctgg gaagccttgg cttttgaccc ccctccctgg gtcaagccct   1500
ttgtacaccc taagcctccg cctcctcttc ctccatccgc cccgtctctc cccttgaac    1560
ctcctcgttc gaccccgcct cgatcctccc tttatccagc cctcactcct tctctaggcg   1620
ccaaacctaa acctcaagtt ctttctgaca gtgggggccc gctcatcgac ctacttacag   1680
aagacccccc gccttatagg gacccaagac caccccccttc cgacagggac ggaaatggtg  1740
gagaagcgac ccctgcggga gaggcaccgg accccctcccc aatggcatct cgcctacgtg  1800
ggagacggga gcccccctgtg gccgactcca ctacctcgca ggcattcccc ctccgcgcag  1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc cccccctgaac ccaggataac cctcaaagtc gggggggcaac  2880
ccgtcacctt cctggtagat actggggccc aacactccgt gctgacccaa aatcctggac   2940
ccctaagtga taagtctgcc tgggtccaag gggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtcccccctg gaacacgccc ctgctacccg  3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
```

```
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagcccccctt gtaccctctc accaaaacgg ggactctgtt taattggggc ccagaccaac   4200
aaaaggccta tcaagaaatc aagcaagctc ttctaactgc ccccagccctg ggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
```

```
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aacccctca agataagatt aacccgtgga agcccttaat   6420
agtcatggga gtcctgttag gagtagggat ggcagagagc ccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagcccct caataccagt taccccctt ccactaccag   7200
tacaccctca acctcccta caagtccaag tgtcccacag ccaccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta atgtagtctt   8340
atgcaatact cttgtagtct tgcaacatgg taacgatgag ttagcaacat gccttacaag   8400
gagagaaaaa gcaccgtgca tgccgattgg tggaagtaag gtggtacgat cgtgccttat   8460
taggaaggca acagacgggt ctgacatgga ttggacgaac cactgaattc cgcattgcag   8520
agatattgta tttaagtgcc tagctcgata caataaacgc catttgacca ttcaccacat   8580
```

```
tggtgtgcac cggatcctgc tcgcttcggc agcacatata ctagtcgact agggataaca   8640
gggtaattgt ttgaatgagg cttcagtact ttacagaatc gttgcctgca catcttggaa   8700
acacttgctg ggattacttc ttcaggttaa cccaacagaa ggctcgagaa ggtatattgc   8760
tgttgacagt gagcgacacg atcatgtgaa cccaaatagt gaagccacag atgtatttgg   8820
gttcacatga tcgtggtgcc tactgcctcg gaattcaagg ggctacttta ggagcaatta   8880
tcttgtttac taaaactgaa taccttgcta tctctttgat acatttttac aaagctgaat   8940
taaaatggta taaattaaat cactttttc aattggaaga ctaatgcggc ggccgcagat   9000
aaaataaaag attttattta gtctccagaa aaagggggga atgaaagacc ccacctgtag   9060
gtttggcaag ctagcttaag taacgccatt ttgcaaggca tggaaaaata cataactgag   9120
aatagagaag ttcagatcaa ggtcaggaac agatggaaca gctgaatatg ggccaaacag   9180
gatatctgtg gtaagcagtt cctgccccgg ctcagggcca agaacagatg gaacagctga   9240
atatgggcca aacaggatat ctgtggtaag cagttcctgc cccggctcag ggccaagaac   9300
agatggtccc cagatgcggt ccagccctca gcagtttcta gagaaccatc agatgtttcc   9360
agggtgcccc aaggacctga aatgaccctg tgccttattt gaactaacca atcagttcgc   9420
ttctcgcttc tgttcgcgcg cttctgctcc ccgagctcaa taaaagagcc cacaacccct   9480
cactcggggc gccagtcctc cgattgactg agtcgcccgg gtacccgtgt atccaataaa   9540
ccctcttgca gttgcatccg acttgtggtc tcgctgttcc ttgggagggt ctcctctgag   9600
tgattgacta cccgtcagcg ggggtctttc attacatgtg agcaaaaggc cagcaaaagg   9660
ccaggaaccg taaaaaggcc gcgttgctgg cgtttttcca taggctccgc ccccctgacg   9720
agcatcacaa aaatcgacgc tcaagtcaga ggtggcgaaa cccgacagga ctataaagat   9780
accaggcgtt tccccctgga agctccctcg tgcgctctcc tgttccgacc ctgccgctta   9840
ccggatacct gtccgccttt ctcccttcgg gaagcgtggc gctttctcat agctcacgct   9900
gtaggtatct cagttcggtg taggtcgttc gctccaagct gggctgtgtg cacgaacccc   9960
ccgttcagcc cgaccgctgc gccttatccg gtaactatcg tcttgagtcc aacccggtaa  10020
gacacgactt atcgccactg gcagcagcca ctggtaacag gattagcaga gcgaggtatg  10080
taggcggtgc tacagagttc ttgaagtggt ggcctaacta cggctacact agaaggacag  10140
tatttggtat ctgcgctctg ctgaagccag ttaccttcgg aaaaagagtt ggtagctctt  10200
gatccggcaa acaaaccacc gctggtagcg gtggtttttt tgtttgcaag cagcagatta  10260
cgcgcagaaa aaaaggatct caagaagatc ctttgatctt ttctacgggg tctgacgctc  10320
agtggaacga aaactcacgt taagggattt tggtcatgag attatcaaaa aggatcttca  10380
cctagatcct tttaaattaa aaatgaagtt ttaaatcaat ctaaagtata tatgagtaaa  10440
cttggtctga cagttaccaa tgcttaatca gtgaggcacc tatctcagcg atctgtctat  10500
ttcgttcatc catagttgcc tgactccccg tcgtgtagat aactacgata cgggagggct  10560
taccatctgg ccccagtgct gcaatgatac cgcgagaccc acgctcaccg gctccagatt  10620
tatcagcaat aaaccagcca gccggaaggg ccgagcgcag aagtggtcct gcaactttat  10680
ccgcctccat ccagtctatt aattgttgcc gggaagctag agtaagtagt tcgccagtta  10740
atagtttgcg caacgttgtt gccattgctg caggcatcgt ggtgtcacgc tcgtcgtttg  10800
gtatggcttc attcagctcc ggttcccaac gatcaaggcg agttacatga tcccccatgt  10860
tgtgcaaaaa agcggttagc tccttcggtc ctccgatcgt tgtcagaagt aagttggccg  10920
```

```
cagtgttatc actcatggtt atggcagcac tgcataattc tcttactgtc atgccatccg  10980

taagatgctt ttctgtgact ggtgagtact caaccaagtc attctgagaa tagtgtatgc  11040

ggcgaccgag ttgctcttgc ccggcgtcaa cacgggataa taccgcgcca catagcagaa  11100

ctttaaaagt gctcatcatt ggaaaacgtt cttcggggcg aaaactctca aggatcttac  11160

cgctgttgag atccagttcg atgtaaccca ctcgtgcacc caactgatct tcagcatctt  11220

ttactttcac cagcgtttct gggtgagcaa aaacaggaag gcaaaatgcc gcaaaaaagg  11280

gaataagggc gacacggaaa tgttgaatac tcatactctt cctttttcaa tattattgaa  11340

gcatttatca gggttattgt ctcatgagcg gatacatatt tgaatgtatt tagaaaaata  11400

aacaaatagg ggttccgcgc acatttcccc gaaaagtgcc acctgacgtc taagaaacca  11460

ttattatcat gacattaacc tataaaaata ggcgtatcac gaggcccttt cgtcttcaag  11520

aattccat                                                          11528
```

<210> SEQ ID NO 10
<211> LENGTH: 12008
<212> TYPE: DNA
<213> ORGANISM: Artificial Sequence
<220> FEATURE:
<223> OTHER INFORMATION: Vector pAC3-RSV-yCD2-IDO1miR30shRNA2

<400> SEQUENCE: 10

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cggcgccagt cctccgattg    600

actgagtcgc ccgggtaccc gtgtatccaa taaaccctct tgcagttgca tccgacttgt    660

ggtctcgctg ttccttggga gggtctcctc tgagtgattg actacccgtc agcgggggtc    720

tttcatttgg gggctcgtcc gggatcggga gacccctgcc cagggaccac cgacccacca    780

ccgggaggta agctggccag caacttatct gtgtctgtcc gattgtctag tgtctatgac    840

tgattttatg cgcctgcgtc ggtactagtt agctaactag ctctgtatct ggcggacccg    900

tggtggaact gacgagttcg gaacacccgg ccgcaaccct gggagacgtc ccagggactt    960

cgggggccgt ttttgtggcc cgacctgagt ccaaaaatcc cgatcgtttt ggactctttg   1020

gtgcaccccc cttagaggag ggatatgtgg ttctggtagg agacgagaac ctaaaacagt   1080

tcccgcctcc gtctgaattt ttgctttcgg tttgggaccg aagccgcgcc gcgcgtcttg   1140

tctgctgcag catcgttctg tgttgtctct gtctgactgt gtttctgtat ttgtctgaaa   1200

atatgggcca gactgttacc actcccttaa gtttgacctt aggtcactgg aaagatgtcg   1260

agcggatcgc tcacaaccag tcggtagatg tcaagaagag acgttgggtt accttctgct   1320

ctgcagaatg gccaaccttt aacgtcggat ggccgcgaga cggcaccttt aaccgagacc   1380

tcatcaccca ggttaagatc aaggtctttt cacctggccc gcatggacac ccagaccagg   1440
```

```
tcccctacat cgtgacctgg gaagccttgg cttttgaccc ccctccctgg gtcaagccct   1500
ttgtacaccc taagcctccg cctcctcttc ctccatccgc cccgtctctc cccccttgaac  1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gcccccctgtg gccgactcca ctacctcgca ggcattcccc ctccgcgcag  1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc gggggggcaac  2880
ccgtcacctt cctggtagat actggggccc aacactccgt gctgacccaa aatcctggac   2940
ccctaagtga taagtctgcc tgggtccaag ggctactgg aggaaagcgg tatcgctgga    3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
```

```
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc ccagccctg gggttgccag    4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
```

-continued

```
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag ggggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagccccct caataccagt tacccccctt ccactaccag   7200
tacaccctca acctccccta caagtccaag tgtcccacag ccacccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta atgtagtctt   8340
atgcaatact cttgtagtct tgcaacatgg taacgatgag ttagcaacat gccttacaag   8400
gagagaaaaa gcaccgtgca tgccgattgg tggaagtaag gtggtacgat cgtgccttat   8460
taggaaggca acagacgggt ctgacatgga ttggacgaac cactgaattc cgcattgcag   8520
```

```
agatattgta tttaagtgcc tagctcgata caataaacgc catttgacca ttcaccacat   8580
tggtgtgcac catggtgacc ggcggcatgg cctccaagtg ggatcaaaag ggcatggata   8640
tcgcttacga ggaggccctg ctgggctaca aggagggcgg cgtgcctatc ggcggctgtc   8700
tgatcaacaa caaggacggc agtgtgctgg gcaggggcca caacatgagg ttccagaagg   8760
gctccgccac cctgcacggc gagatctcca ccctggagaa ctgtggcagg ctggagggca   8820
aggtgtacaa ggacaccacc ctgtacacca ccctgtcccc ttgtgacatg tgtaccggcg   8880
ctatcatcat gtacggcatc cctaggtgtg tgatcggcga gaacgtgaac ttcaagtcca   8940
agggcgagaa gtacctgcaa accaggggcc acgaggtggt ggttgttgac gatgagaggt   9000
gtaagaagct gatgaagcag ttcatcgacg agaggcctca ggactggttc gaggatatcg   9060
gcgagtaatg aggatcctgc tcgcttcggc agcacatata ctagtcgact agggataaca   9120
gggtaattgt ttgaatgagg cttcagtact ttacagaatc gttgcctgca catcttggaa   9180
acacttgctg ggattacttc ttcaggttaa cccaacagaa ggctcgagaa ggtatattgc   9240
tgttgacagt gagcgacacg atcatgtgaa cccaaatagt gaagccacag atgtatttgg   9300
gttcacatga tcgtggtgcc tactgcctcg gaattcaagg ggctacttta ggagcaatta   9360
tcttgtttac taaaactgaa taccttgcta tctctttgat acatttttac aaagctgaat   9420
taaaatggta taaattaaat cacttttttc aattggaaga ctaatgcggc ggccgcagat   9480
aaaataaaag attttattta gtctccagaa aaagggggga atgaaagacc ccacctgtag   9540
gtttggcaag ctagcttaag taacgccatt ttgcaaggca tggaaaaata cataactgag   9600
aatagagaag ttcagatcaa ggtcaggaac agatggaaca gctgaatatg ggccaaacag   9660
gatatctgtg gtaagcagtt cctgccccgg ctcagggcca agaacagatg gaacagctga   9720
atatgggcca aacaggatat ctgtggtaag cagttcctgc cccggctcag ggccaagaac   9780
agatggtccc cagatgcggt ccagccctca gcagtttcta gagaaccatc agatgtttcc   9840
agggtgcccc aaggacctga aatgaccctg tgccttattt gaactaacca atcagttcgc   9900
ttctcgcttc tgttcgcgcg cttctgctcc ccgagctcaa taaaagagcc cacaacccct   9960
cactcggggc gccagtcctc cgattgactg agtcgcccgg gtacccgtgt atccaataaa  10020
ccctcttgca gttgcatccg acttgtggtc tcgctgttcc ttgggagggt ctcctctgag  10080
tgattgacta cccgtcagcg ggggtctttc attacatgtg agcaaaaggc cagcaaaagg  10140
ccaggaaccg taaaaaggcc gcgttgctgg cgtttttcca taggctccgc ccccctgacg  10200
agcatcacaa aaatcgacgc tcaagtcaga ggtggcgaaa cccgacagga ctataaagat  10260
accaggcgtt tccccctgga agctccctcg tgcgctctcc tgttccgacc ctgccgctta  10320
ccggatacct gtccgccttt ctcccttcgg gaagcgtggc gctttctcat agctcacgct  10380
gtaggtatct cagttcggtg taggtcgttc gctccaagct gggctgtgtg cacgaacccc  10440
ccgttcagcc cgaccgctgc gccttatccg gtaactatcg tcttgagtcc aacccggtaa  10500
gacacgactt atcgccactg gcagcagcca ctggtaacag gattagcaga gcgaggtatg  10560
taggcggtgc tacagagttc ttgaagtggt ggcctaacta cggctacact agaaggacag  10620
tatttggtat ctgcgctctg ctgaagccag ttaccttcgg aaaaagagtt ggtagctctt  10680
gatccggcaa acaaaccacc gctggtagcg gtggtttttt tgtttgcaag cagcagatta  10740
cgcgcagaaa aaaaggatct caagaagatc ctttgatctt ttctacgggg tctgacgctc  10800
agtggaacga aaactcacgt taagggattt tggtcatgag attatcaaaa aggatcttca  10860
cctagatcct tttaaattaa aaatgaagtt ttaaatcaat ctaaagtata tatgagtaaa  10920
```

```
cttggtctga cagttaccaa tgcttaatca gtgaggcacc tatctcagcg atctgtctat  10980

ttcgttcatc catagttgcc tgactccccg tcgtgtagat aactacgata cgggagggct  11040

taccatctgg ccccagtgct gcaatgatac cgcgagaccc acgctcaccg gctccagatt  11100

tatcagcaat aaaccagcca gccggaaggg ccgagcgcag aagtggtcct gcaactttat  11160

ccgcctccat ccagtctatt aattgttgcc gggaagctag agtaagtagt tcgccagtta  11220

atagtttgcg caacgttgtt gccattgctg caggcatcgt ggtgtcacgc tcgtcgtttg  11280

gtatggcttc attcagctcc ggttcccaac gatcaaggcg agttacatga tcccccatgt  11340

tgtgcaaaaa agcggttagc tccttcggtc ctccgatcgt tgtcagaagt aagttggccg  11400

cagtgttatc actcatggtt atggcagcac tgcataattc tcttactgtc atgccatccg  11460

taagatgctt ttctgtgact ggtgagtact caaccaagtc attctgagaa tagtgtatgc  11520

ggcgaccgag ttgctcttgc ccggcgtcaa cacgggataa taccgcgcca catagcagaa  11580

ctttaaaagt gctcatcatt ggaaaacgtt cttcggggcg aaaactctca aggatcttac  11640

cgctgttgag atccagttcg atgtaaccca ctcgtgcacc caactgatct tcagcatctt  11700

ttactttcac cagcgtttct gggtgagcaa aaacaggaag gcaaaatgcc gcaaaaaagg  11760

gaataagggc gacacggaaa tgttgaatac tcatactctt cctttttcaa tattattgaa  11820

gcatttatca gggttattgt ctcatgagcg gatacatatt tgaatgtatt tagaaaaata  11880

aacaaatagg ggttccgcgc acatttcccc gaaaagtgcc acctgacgtc taagaaacca  11940

ttattatcat gacattaacc tataaaaata ggcgtatcac gaggcccttt cgtcttcaag  12000

aattccat                                                           12008
```

<210> SEQ ID NO 11
<211> LENGTH: 12273
<212> TYPE: DNA
<213> ORGANISM: Artificial Sequence
<220> FEATURE:
<223> OTHER INFORMATION: Vector pAC3-RSV-yCD2-U6-IDO1miR30shRNA2

<400> SEQUENCE: 11

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cggcgccagt cctccgattg    600

actgagtcgc ccgggtaccc gtgtatccaa taaaccctct tgcagttgca tccgacttgt    660

ggtctcgctg ttccttggga gggtctcctc tgagtgattg actacccgtc agcgggggtc    720

tttcatttgg gggctcgtcc gggatcggga gacccctgcc cagggaccac cgacccacca    780

ccgggaggta agctggccag caacttatct gtgtctgtcc gattgtctag tgtctatgac    840

tgattttatg cgcctgcgtc ggtactagtt agctaactag ctctgtatct ggcggacccg    900
```

-continued

```
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaaa   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc cccctgaac    1560
ctcctcgttc gaccccgcct cgatcctccc tttatccagc cctcactcct tctctaggcg   1620
ccaaacctaa acctcaagtt ctttctgaca gtgggggggcc gctcatcgac ctacttacag   1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga    3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
```

```
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg ggtttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
```

-continued

```
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc    6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagcccccct caataccagt taccccccctt ccactaccag 7200
tacaccctca acctccccta caagtccaag tgtcccacag ccacccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
```

```
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta atgtagtctt   8340
atgcaatact cttgtagtct tgcaacatgg taacgatgag ttagcaacat gccttacaag   8400
gagagaaaaa gcaccgtgca tgccgattgg tggaagtaag gtggtacgat cgtgccttat   8460
taggaaggca acagacgggt ctgacatgga ttggacgaac cactgaattc cgcattgcag   8520
agatattgta tttaagtgcc tagctcgata caataaacgc catttgacca ttcaccacat   8580
tggtgtgcac catggtgacc ggcggcatgg cctccaagtg ggatcaaaag ggcatggata   8640
tcgcttacga ggaggccctg ctgggctaca aggagggcgg cgtgcctatc ggcggctgtc   8700
tgatcaacaa caaggacggc agtgtgctgg gcaggggcca caacatgagg ttccagaagg   8760
gctccgccac cctgcacggc gagatctcca ccctggagaa ctgtggcagg ctggagggca   8820
aggtgtacaa ggacaccacc ctgtacacca ccctgtcccc ttgtgacatg tgtaccggcg   8880
ctatcatcat gtacggcatc cctaggtgtg tgatcggcga gaacgtgaac ttcaagtcca   8940
agggcgagaa gtacctgcaa accaggggcc acgaggtggt ggttgttgac gatgagaggt   9000
gtaagaagct gatgaagcag ttcatcgacg agaggcctca ggactggttc gaggatatcg   9060
gcgagtaatg aaaggtcggg caggaagagg gcctatttcc catgattcct tcatatttgc   9120
atatacgata caaggctgtt agagagataa ttagaattaa tttgactgta aacacaaaga   9180
tattagtaca aaatacgtga cgtagaaagt aataatttct tgggtagttt gcagttttta   9240
aaattatgtt ttaaaatgga ctatcatatg cttaccgtaa cttgaaagta tttcgatttc   9300
ttggctttat atatcttgtg gaaaggacga aacaccggat cctgctcgct tcggcagcac   9360
atatactagt cgactaggga taacagggta attgtttgaa tgaggcttca gtactttaca   9420
gaatcgttgc ctgcacatct tggaaacact tgctgggatt acttcttcag gttaacccaa   9480
cagaaggctc gagaaggtat attgctgttg acagtgagcg acacgatcat gtgaacccaa   9540
atagtgaagc cacagatgta tttgggttca catgatcgtg gtgcctactg cctcggaatt   9600
caaggggcta ctttaggagc aattatcttg tttactaaaa ctgaatacct tgctatctct   9660
ttgatacatt tttacaaagc tgaattaaaa tggtataaat taaatcactt ttttcaattg   9720
gaagactaat gcggcggccg cagataaaat aaaagatttt atttagtctc cagaaaaagg   9780
ggggaatgaa agaccccacc tgtaggtttg gcaagctagc ttaagtaacg ccattttgca   9840
aggcatggaa aaatacataa ctgagaatag agaagttcag atcaaggtca ggaacagatg   9900
gaacagctga atatgggcca aacaggatat ctgtggtaag cagttcctgc cccggctcag   9960
ggccaagaac agatggaaca gctgaatatg ggccaaacag gatatctgtg gtaagcagtt  10020
cctgccccgg ctcagggcca agaacagatg gtccccagat gcggtccagc cctcagcagt  10080
ttctagagaa ccatcagatg tttccagggt gccccaagga cctgaaatga ccctgtgcct  10140
tatttgaact aaccaatcag ttcgcttctc gcttctgttc gcgcgcttct gctccccgag  10200
ctcaataaaa gagcccacaa cccctcactc ggggcgccag tcctccgatt gactgagtcg  10260
cccgggtacc cgtgtatcca ataaaccctc ttgcagttgc atccgacttg tggtctcgct  10320
gttccttggg agggtctcct ctgagtgatt gactacccgt cagcgggggt ctttcattac  10380
```

```
atgtgagcaa aaggccagca aaaggccagg aaccgtaaaa aggccgcgtt gctggcgttt  10440
ttccataggc tccgcccccc tgacgagcat cacaaaaatc gacgctcaag tcagaggtgg  10500
cgaaacccga caggactata aagataccag gcgtttcccc ctggaagctc cctcgtgcgc  10560
tctcctgttc cgaccctgcc gcttaccgga tacctgtccg cctttctccc ttcgggaagc  10620
gtggcgcttt ctcatagctc acgctgtagg tatctcagtt cggtgtaggt cgttcgctcc  10680
aagctgggct gtgtgcacga accccccgtt cagcccgacc gctgcgcctt atccggtaac  10740
tatcgtcttg agtccaaccc ggtaagacac gacttatcgc cactggcagc agccactggt  10800
aacaggatta gcagagcgag gtatgtaggc ggtgctacag agttcttgaa gtggtggcct  10860
aactacggct acactagaag gacagtattt ggtatctgcg ctctgctgaa gccagttacc  10920
ttcggaaaaa gagttggtag ctcttgatcc ggcaaacaaa ccaccgctgg tagcggtggt  10980
tttttgttt gcaagcagca gattacgcgc agaaaaaaag gatctcaaga agatcctttg  11040
atcttttcta cggggtctga cgctcagtgg aacgaaaact cacgttaagg gattttggtc  11100
atgagattat caaaaaggat cttcacctag atccttttaa attaaaaatg aagttttaaa  11160
tcaatctaaa gtatatatga gtaaacttgg tctgacagtt accaatgctt aatcagtgag  11220
gcacctatct cagcgatctg tctatttcgt tcatccatag ttgcctgact ccccgtcgtg  11280
tagataacta cgatacggga gggcttacca tctggcccca gtgctgcaat gataccgcga  11340
gacccacgct caccggctcc agatttatca gcaataaacc agccagccgg aagggccgag  11400
cgcagaagtg gtcctgcaac tttatccgcc tccatccagt ctattaattg ttgccgggaa  11460
gctagagtaa gtagttcgcc agttaatagt ttgcgcaacg ttgttgccat tgctgcaggc  11520
atcgtggtgt cacgctcgtc gtttggtatg gcttcattca gctccggttc ccaacgatca  11580
aggcgagtta catgatcccc catgttgtgc aaaaaagcgg ttagctcctt cggtcctccg  11640
atcgttgtca gaagtaagtt ggccgcagtg ttatcactca tggttatggc agcactgcat  11700
aattctctta ctgtcatgcc atccgtaaga tgcttttctg tgactggtga gtactcaacc  11760
aagtcattct gagaatagtg tatgcggcga ccgagttgct cttgcccggc gtcaacacgg  11820
gataataccg cgccacatag cagaacttta aaagtgctca tcattggaaa acgttcttcg  11880
gggcgaaaac tctcaaggat cttaccgctg ttgagatcca gttcgatgta acccactcgt  11940
gcacccaact gatcttcagc atcttttact ttcaccagcg tttctgggtg agcaaaaaca  12000
ggaaggcaaa atgccgcaaa aaagggaata agggcgacac ggaaatgttg aatactcata  12060
ctcttccttt ttcaatatta ttgaagcatt tatcagggtt attgtctcat gagcggatac  12120
atatttgaat gtatttagaa aaataaacaa ataggggttc cgcgcacatt tccccgaaaa  12180
gtgccacctg acgtctaaga aaccattatt atcatgacat taacctataa aaataggcgt  12240
atcacgaggc cctttcgtct tcaagaattc cat                               12273
```

<210> SEQ ID NO 12
<211> LENGTH: 11489
<212> TYPE: DNA
<213> ORGANISM: Artificial Sequence
<220> FEATURE:
<223> OTHER INFORMATION: Vector pAC3-H1-PDL1miR30shRN4

<400> SEQUENCE: 12

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
```

```
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga gacccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaaa   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttcttttttct gaagatccag gtaaactgac agctctgatc gagtctgtcc   1980
tcatcaccca tcagcccacc tggggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
```

```
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg ggggttgccag  4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
```

```
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc ccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagccccct caataccagt tacccccctt ccactaccag   7200
tacaccctca acctccccta caagtccaag tgtcccacag ccacccccag gaactggaga   7260
```

```
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtg aacgctgacg   8340
tcatcaaccc gctccaagga atcgcgggcc cagtgtcact aggcgggaac acccagcgcg   8400
cgtgcgccct ggcaggaaga tggctgtgag ggacagggga gtggcgccct gcaatatttg   8460
catgtcgcta tgtgttctgg gaaatcacca taaacgtgaa atgtctttgg atttgggaat   8520
cttataagtt ctgtatgaga ccactctttc ccggatcctg ctcgcttcgg cagcacatat   8580
actagtcgac tagggataac agggtaattg tttgaatgag gcttcagtac tttacagaat   8640
cgttgcctgc acatcttgga aacacttgct gggattactt cttcaggtta acccaacaga   8700
aggctcgaga aggtatattg ctgttgacag tgagcgcggt agcaatatga caattgatag   8760
tgaagccaca gatgtatcaa ttgtcatatt gctaccatgc ctactgcctc ggaattcaag   8820
gggctacttt aggagcaatt atcttgttta ctaaaactga ataccttgct atctctttga   8880
tacattttta caaagctgaa ttaaaatggt ataaattaaa tcactttttt caattggaag   8940
actaatgcgg cggccgcaga taaaataaaa gattttattt agtctccaga aaaagggggg   9000
aatgaaagac cccacctgta ggtttggcaa gctagcttaa gtaacgccat tttgcaaggc   9060
atggaaaaat acataactga gaatagagaa gttcagatca aggtcaggaa cagatggaac   9120
agctgaatat gggccaaaca ggatatctgt ggtaagcagt tcctgccccg gctcagggcc   9180
aagaacagat ggaacagctg aatatgggcc aaacaggata tctgtggtaa gcagttcctg   9240
ccccggctca gggccaagaa cagatggtcc ccagatgcgg tccagccctc agcagtttct   9300
agagaaccat cagatgtttc cagggtgccc caaggacctg aaatgaccct gtgccttatt   9360
tgaactaacc aatcagttcg cttctcgctt ctgttcgcgc gcttctgctc cccgagctca   9420
ataaaagagc ccacaacccc tcactcgggg cgccagtcct ccgattgact gagtcgcccg   9480
ggtacccgtg tatccaataa accctcttgc agttgcatcc gacttgtggt ctcgctgttc   9540
cttgggaggg tctcctctga gtgattgact acccgtcagc gggggtcttt cattacatgt   9600
gagcaaaagg ccagcaaaag gccaggaacc gtaaaaaggc cgcgttgctg gcgtttttcc   9660
```

```
ataggctccg ccccctgac gagcatcaca aaaatcgacg ctcaagtcag aggtggcgaa   9720

acccgacagg actataaaga taccaggcgt ttccccctgg aagctccctc gtgcgctctc   9780

ctgttccgac cctgccgctt accggatacc tgtccgcctt tctcccttcg ggaagcgtgg   9840

cgctttctca tagctcacgc tgtaggtatc tcagttcggt gtaggtcgtt cgctccaagc   9900

tgggctgtgt gcacgaaccc cccgttcagc ccgaccgctg cgccttatcc ggtaactatc   9960

gtcttgagtc caacccggta agacacgact tatcgccact ggcagcagcc actggtaaca  10020

ggattagcag agcgaggtat gtaggcggtg ctacagagtt cttgaagtgg tggcctaact  10080

acggctacac tagaaggaca gtatttggta tctgcgctct gctgaagcca gttaccttcg  10140

gaaaaagagt tggtagctct tgatccggca aacaaaccac cgctggtagc ggtggttttt  10200

ttgtttgcaa gcagcagatt acgcgcagaa aaaaaggatc tcaagaagat cctttgatct  10260

tttctacggg gtctgacgct cagtggaacg aaaactcacg ttaagggatt ttggtcatga  10320

gattatcaaa aaggatcttc acctagatcc ttttaaatta aaaatgaagt tttaaatcaa  10380

tctaaagtat atatgagtaa acttggtctg acagttacca atgcttaatc agtgaggcac  10440

ctatctcagc gatctgtcta tttcgttcat ccatagttgc ctgactcccc gtcgtgtaga  10500

taactacgat acgggagggc ttaccatctg gccccagtgc tgcaatgata ccgcgagacc  10560

cacgctcacc ggctccagat ttatcagcaa taaaccagcc agccggaagg gccgagcgca  10620

gaagtggtcc tgcaacttta tccgcctcca tccagtctat taattgttgc cgggaagcta  10680

gagtaagtag ttcgccagtt aatagtttgc gcaacgttgt tgccattgct gcaggcatcg  10740

tggtgtcacg ctcgtcgttt ggtatggctt cattcagctc cggttcccaa cgatcaaggc  10800

gagttacatg atcccccatg ttgtgcaaaa aagcggttag ctccttcggt cctccgatcg  10860

ttgtcagaag taagttggcc gcagtgttat cactcatggt tatggcagca ctgcataatt  10920

ctcttactgt catgccatcc gtaagatgct tttctgtgac tggtgagtac tcaaccaagt  10980

cattctgaga atagtgtatg cggcgaccga gttgctcttg cccggcgtca acacgggata  11040

ataccgcgcc acatagcaga actttaaaag tgctcatcat tggaaaacgt tcttcggggc  11100

gaaaactctc aaggatctta ccgctgttga gatccagttc gatgtaaccc actcgtgcac  11160

ccaactgatc ttcagcatct tttactttca ccagcgtttc tgggtgagca aaaacaggaa  11220

ggcaaaatgc cgcaaaaaag ggaataaggg cgacacggaa atgttgaata ctcatactct  11280

tcctttttca atattattga agcatttatc agggttattg tctcatgagc ggatacatat  11340

ttgaatgtat ttagaaaaat aaacaaatag gggttccgcg cacatttccc cgaaaagtgc  11400

cacctgacgt ctaagaaacc attattatca tgacattaac ctataaaaat aggcgtatca  11460

cgaggccctt tcgtcttcaa gaattccat                                    11489
```

<210> SEQ ID NO 13
<211> LENGTH: 11526
<212> TYPE: DNA
<213> ORGANISM: Artificial Sequence
<220> FEATURE:
<223> OTHER INFORMATION: Vector pAC3-U6-PDL1-miR30shRNA4

<400> SEQUENCE: 13

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180
```

-continued

```
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga gacccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaaa   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc cccctgaac    1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac caccccctc cgacagggac ggaaatggtg    1740
gagaagcgac ccctgcggga gaggcaccgg accccctccc aatggcatct cgcctacgtg   1800
ggagacggga gcccccctgtg gccgactcca ctacctcgca ggcattcccc ctccgcgcag  1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tggacgact gtcagcagct gttggggact ctgctgaccg    2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
```

```
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtcccccctg gaacacgccc ctgctacccg   3480
ttaagaaacc agggactaat gattataggc ctgtccagga tctgagagaa gtcaacaagc   3540
gggtggaaga catccacccc accgtgccca accccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagcccccctt gtaccctctc accaaaacgg ggactctgtt taattggggc ccagaccaac   4200
aaaaggccta tcaagaaatc aagcaagctc ttctaactgc ccccagccctg ggggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
```

```
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aacccctca agataagatt aacccgtgga agcccttaat   6420
agtcatggga gtcctgttag gagtagggat ggcagagagc cccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca cccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagcccct caataccagt tacccccctt ccactaccag   7200
tacaccctca acctccccta caagtccaag tgtcccacag ccacccccag gaactggaga   7260
tagactacta gctctagtca aaggagccta tcaggcgctt aacctcacca atcccgacaa   7320
```

```
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta aggtcgggca   8340
ggaagagggc ctatttccca tgattccttc atatttgcat atacgataca aggctgttag   8400
agagataatt agaattaatt tgactgtaaa cacaaagata ttagtacaaa atacgtgacg   8460
tagaaagtaa taatttcttg ggtagtttgc agtttttaaa attatgtttt aaaatggact   8520
atcatatgct taccgtaact tgaaagtatt tcgatttctt ggctttatat atcttgtgga   8580
aaggacgaaa caccgtgctc gcttcggcag cacatatact agtcgactag ggataacagg   8640
gtaattgttt gaatgaggct tcagtacttt acagaatcgt tgcctgcaca tcttggaaac   8700
acttgctggg attacttctt caggttaacc caacagaagg ctcgagaagg tatattgctg   8760
ttgacagtga gcgcggtagc aatatgacaa ttgatagtga agccacagat gtatcaattg   8820
tcatattgct accatgccta ctgcctcgga attcaagggg ctactttagg agcaattatc   8880
ttgtttacta aaactgaata ccttgctatc tctttgatac atttttacaa agctgaatta   8940
aaatggtata aattaaatca ctttttttcaa ttggaagact aatgcggcgg ccgcagataa   9000
aataaaagat tttatttagt ctccagaaaa aggggggaat gaaagacccc acctgtaggt   9060
ttggcaagct agcttaagta acgccatttt gcaaggcatg gaaaaataca taactgagaa   9120
tagagaagtt cagatcaagg tcaggaacag atggaacagc tgaatatggg ccaaacagga   9180
tatctgtggt aagcagttcc tgccccggct cagggccaag aacagatgga acagctgaat   9240
atgggccaaa caggatatct gtggtaagca gttcctgccc cggctcaggg ccaagaacag   9300
atggtcccca gatgcggtcc agccctcagc agtttctaga gaaccatcag atgtttccag   9360
ggtgccccaa ggacctgaaa tgaccctgtg ccttatttga actaaccaat cagttcgctt   9420
ctcgcttctg ttcgcgcgct tctgctcccc gagctcaata aaagagccca caacccctca   9480
ctcggggcgc cagtcctccg attgactgag tcgcccgggt acccgtgtat ccaataaacc   9540
ctcttgcagt tgcatccgac ttgtggtctc gctgttcctt gggagggtct cctctgagtg   9600
attgactacc cgtcagcggg ggtctttcat tacatgtgag caaaaggcca gcaaaaggcc   9660
```

```
aggaaccgta aaaaggccgc gttgctggcg tttttccata ggctccgccc ccctgacgag   9720

catcacaaaa atcgacgctc aagtcagagg tggcgaaacc cgacaggact ataaagatac   9780

caggcgtttc cccctggaag ctccctcgtg cgctctcctg ttccgaccct gccgcttacc   9840

ggatacctgt ccgcctttct cccttcggga agcgtggcgc tttctcatag ctcacgctgt   9900

aggtatctca gttcggtgta ggtcgttcgc tccaagctgg gctgtgtgca cgaacccccc   9960

gttcagcccg accgctgcgc cttatccggt aactatcgtc ttgagtccaa cccggtaaga  10020

cacgacttat cgccactggc agcagccact ggtaacagga ttagcagagc gaggtatgta  10080

ggcggtgcta cagagttctt gaagtggtgg cctaactacg gctacactag aaggacagta  10140

tttggtatct gcgctctgct gaagccagtt accttcggaa aaagagttgg tagctcttga  10200

tccggcaaac aaaccaccgc tggtagcggt ggtttttttg tttgcaagca gcagattacg  10260

cgcagaaaaa aaggatctca agaagatcct ttgatctttt ctacggggtc tgacgctcag  10320

tggaacgaaa actcacgtta agggattttg gtcatgagat tatcaaaaag gatcttcacc  10380

tagatccttt taaattaaaa atgaagtttt aaatcaatct aaagtatata tgagtaaact  10440

tggtctgaca gttaccaatg cttaatcagt gaggcaccta tctcagcgat ctgtctattt  10500

cgttcatcca tagttgcctg actccccgtc gtgtagataa ctacgatacg ggagggctta  10560

ccatctggcc ccagtgctgc aatgataccg cgagacccac gctcaccggc tccagattta  10620

tcagcaataa accagccagc cggaagggcc gagcgcagaa gtggtcctgc aactttatcc  10680

gcctccatcc agtctattaa ttgttgccgg gaagctagag taagtagttc gccagttaat  10740

agtttgcgca acgttgttgc cattgctgca ggcatcgtgg tgtcacgctc gtcgtttggt  10800

atggcttcat tcagctccgg ttcccaacga tcaaggcgag ttacatgatc ccccatgttg  10860

tgcaaaaaag cggttagctc cttcggtcct ccgatcgttg tcagaagtaa gttggccgca  10920

gtgttatcac tcatggttat ggcagcactg cataattctc ttactgtcat gccatccgta  10980

agatgctttt ctgtgactgg tgagtactca accaagtcat tctgagaata gtgtatgcgg  11040

cgaccgagtt gctcttgccc ggcgtcaaca cgggataata ccgcgccaca tagcagaact  11100

ttaaaagtgc tcatcattgg aaaacgttct tcggggcgaa aactctcaag gatcttaccg  11160

ctgttgagat ccagttcgat gtaacccact cgtgcaccca actgatcttc agcatctttt  11220

actttcacca gcgtttctgg gtgagcaaaa acaggaaggc aaaatgccgc aaaaaaggga  11280

ataagggcga cacggaaatg ttgaatactc atactcttcc tttttcaata ttattgaagc  11340

atttatcagg gttattgtct catgagcgga tacatatttg aatgtattta gaaaaataaa  11400

caaatagggg ttccgcgcac atttccccga aaagtgccac ctgacgtcta agaaaccatt  11460

attatcatga cattaaccta taaaaatagg cgtatcacga ggccctttcg tcttcaagaa  11520

ttccat                                                             11526
```

<210> SEQ ID NO 14
<211> LENGTH: 11528
<212> TYPE: DNA
<213> ORGANISM: Artificial Sequence
<220> FEATURE:
<223> OTHER INFORMATION: Vector pAC3-RSV-PDL1miR30shRNA4

<400> SEQUENCE: 14

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180
```

```
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga gacccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaaa   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac caccccctc cgacagggac ggaaatggtg    1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
```

-continued

```
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc ccagccctg gggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
```

```
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agatacettt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt  6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagccccct caataccagt taccccccttt ccactaccag  7200
tacaccctca acctccccta caagtccaag tgtcccacag ccaccccccag gaactggaga  7260
```

```
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta atgtagtctt   8340
atgcaatact cttgtagtct tgcaacatgg taacgatgag ttagcaacat gccttacaag   8400
gagagaaaaa gcaccgtgca tgccgattgg tggaagtaag gtggtacgat cgtgccttat   8460
taggaaggca acagacgggt ctgacatgga ttggacgaac cactgaattc cgcattgcag   8520
agatattgta tttaagtgcc tagctcgata caataaacgc catttgacca ttcaccacat   8580
tggtgtgcac cggatcctgc tcgcttcggc agcacatata ctagtcgact agggataaca   8640
gggtaattgt ttgaatgagg cttcagtact ttacagaatc gttgcctgca catcttggaa   8700
acacttgctg ggattacttc ttcaggttaa cccaacagaa ggctcgagaa ggtatattgc   8760
tgttgacagt gagcgcggta gcaatatgac aattgatagt gaagccacag atgtatcaat   8820
tgtcatattg ctaccatgcc tactgcctcg gaattcaagg ggctacttta ggagcaatta   8880
tcttgtttac taaaactgaa taccttgcta tctctttgat acatttttac aaagctgaat   8940
taaaatggta taaattaaat cacttttttc aattggaaga ctaatgcggc ggccgcagat   9000
aaaataaaag attttattta gtctccagaa aaagggggga atgaaagacc ccacctgtag   9060
gtttggcaag ctagcttaag taacgccatt ttgcaaggca tggaaaaata cataactgag   9120
aatagagaag ttcagatcaa ggtcaggaac agatggaaca gctgaatatg ggccaaacag   9180
gatatctgtg gtaagcagtt cctgccccgg ctcagggcca agaacagatg gaacagctga   9240
atatgggcca aacaggatat ctgtggtaag cagttcctgc cccggctcag ggccaagaac   9300
agatggtccc cagatgcggt ccagccctca gcagtttcta gagaaccatc agatgtttcc   9360
agggtgcccc aaggacctga aatgaccctg tgccttattt gaactaacca atcagttcgc   9420
ttctcgcttc tgttcgcgcg cttctgctcc ccgagctcaa taaaagagcc cacaacccct   9480
cactcggggc gccagtcctc cgattgactg agtcgcccgg gtacccgtgt atccaataaa   9540
ccctcttgca gttgcatccg acttgtggtc tcgctgttcc ttgggagggt ctcctctgag   9600
tgattgacta cccgtcagcg gggtctttc attacatgtg agcaaaaggc cagcaaaagg   9660
```

```
ccaggaaccg taaaaaggcc gcgttgctgg cgtttttcca taggctccgc cccccctgacg   9720

agcatcacaa aaatcgacgc tcaagtcaga ggtggcgaaa cccgacagga ctataaagat   9780

accaggcgtt tccccctgga agctccctcg tgcgctctcc tgttccgacc ctgccgctta   9840

ccggatacct gtccgccttt ctcccttcgg gaagcgtggc gctttctcat agctcacgct   9900

gtaggtatct cagttcggtg taggtcgttc gctccaagct gggctgtgtg cacgaacccc   9960

ccgttcagcc cgaccgctgc gccttatccg gtaactatcg tcttgagtcc aacccggtaa  10020

gacacgactt atcgccactg gcagcagcca ctggtaacag gattagcaga gcgaggtatg  10080

taggcggtgc tacagagttc ttgaagtggt ggcctaacta cggctacact agaaggacag  10140

tatttggtat ctgcgctctg ctgaagccag ttaccttcgg aaaaagagtt ggtagctctt  10200

gatccggcaa acaaaccacc gctggtagcg gtggtttttt tgtttgcaag cagcagatta  10260

cgcgcagaaa aaaaggatct caagaagatc ctttgatctt ttctacgggg tctgacgctc  10320

agtggaacga aaactcacgt taagggattt tggtcatgag attatcaaaa aggatcttca  10380

cctagatcct tttaaattaa aaatgaagtt ttaaatcaat ctaaagtata tatgagtaaa  10440

cttggtctga cagttaccaa tgcttaatca gtgaggcacc tatctcagcg atctgtctat  10500

ttcgttcatc catagttgcc tgactccccg tcgtgtagat aactacgata cgggagggct  10560

taccatctgg ccccagtgct gcaatgatac cgcgagaccc acgctcaccg gctccagatt  10620

tatcagcaat aaaccagcca gccggaaggg ccgagcgcag aagtggtcct gcaactttat  10680

ccgcctccat ccagtctatt aattgttgcc gggaagctag agtaagtagt tcgccagtta  10740

atagtttgcg caacgttgtt gccattgctg caggcatcgt ggtgtcacgc tcgtcgtttg  10800

gtatggcttc attcagctcc ggttcccaac gatcaaggcg agttacatga tcccccatgt  10860

tgtgcaaaaa agcggttagc tccttcggtc ctccgatcgt tgtcagaagt aagttggccg  10920

cagtgttatc actcatggtt atggcagcac tgcataattc tcttactgtc atgccatccg  10980

taagatgctt ttctgtgact ggtgagtact caaccaagtc attctgagaa tagtgtatgc  11040

ggcgaccgag ttgctcttgc ccggcgtcaa cacgggataa taccgcgcca catagcagaa  11100

ctttaaaagt gctcatcatt ggaaaacgtt cttcggggcg aaaactctca aggatcttac  11160

cgctgttgag atccagttcg atgtaaccca ctcgtgcacc caactgatct tcagcatctt  11220

ttactttcac cagcgtttct gggtgagcaa aaacaggaag gcaaaatgcc gcaaaaaagg  11280

gaataagggc gacacggaaa tgttgaatac tcatactctt cctttttcaa tattattgaa  11340

gcatttatca gggttattgt ctcatgagcg gatacatatt tgaatgtatt tagaaaaata  11400

aacaaatagg ggttccgcgc acatttcccc gaaaagtgcc acctgacgtc taagaaacca  11460

ttattatcat gacattaacc tataaaaata ggcgtatcac gaggcccttt cgtcttcaag  11520

aattccat                                                           11528
```

<210> SEQ ID NO 15
<211> LENGTH: 12008
<212> TYPE: DNA
<213> ORGANISM: Artificial Sequence
<220> FEATURE:
<223> OTHER INFORMATION: Vector pAC3-RSV-yCD2-PDL1miR30shRNA4

<400> SEQUENCE: 15

```
tagttattaa tagtaatcaa ttacggggtc attagttcat agcccatata tggagttccg     60

cgttacataa cttacggtaa atggcccgcc tggctgaccg cccaacgacc cccgcccatt    120
```

-continued gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440
tcccctacat cgtgacctgg gaagccttgg cttttgaccc ccctccctgg gtcaagccct 1500
ttgtacaccc taagcctccg cctcctcttc ctccatccgc cccgtctctc ccccttgaac 1560
ctcctcgttc gaccccgcct cgatcctccc tttatccagc cctcactcct tctctaggcg 1620
ccaaacctaa acctcaagtt ctttctgaca gtggggggcc gctcatcgac ctacttacag 1680
aagacccccc gccttatagg gacccaagac caccccctc cgacagggac ggaaatggtg 1740
gagaagcgac ccctgcggga gaggcaccgg acccctcccc aatggcatct cgcctacgtg 1800
ggagacggga gccccctgtg gccgactcca ctacctcgca ggcattcccc ctccgcgcag 1860
gaggaaacgg acagcttcaa tactggccgt tctcctcttc tgacctttac aactggaaaa 1920
ataataaccc ttctttttct gaagatccag gtaaactgac agctctgatc gagtctgtcc 1980
tcatcaccca tcagcccacc tgggacgact gtcagcagct gttggggact ctgctgaccg 2040
gagaagaaaa acaacgggtg ctcttagagg ctagaaaggc ggtgcggggc gatgatgggc 2100
gccccactca actgcccaat gaagtcgatg ccgcttttcc cctcgagcgc ccagactggg 2160
attacaccac ccaggcaggt aggaaccacc tagtccacta tcgccagttg ctcctagcgg 2220
gtctccaaaa cgcgggcaga agccccacca atttggccaa ggtaaaagga ataacacaag 2280
ggcccaatga gtctccctcg gccttcctag agagacttaa ggaagcctat cgcaggtaca 2340
ctccttatga ccctgaggac ccagggcaag aaactaatgt gtctatgtct ttcatttggc 2400
agtctgcccc agacattggg agaaagttag agaggttaga agatttaaaa aacaagacgc 2460
ttggagattt ggttagagag gcagaaaaga tctttaataa acgagaaacc ccggaagaaa 2520

```
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg ggggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
```

-continued

```
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aacccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagcccccct caataccagt taccccccctt ccactaccag   7200
tacaccctca acctccccta caagtccaag tgtcccacag ccaccccccag gaactggaga   7260
```

```
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta atgtagtctt   8340
atgcaatact cttgtagtct tgcaacatgg taacgatgag ttagcaacat gccttacaag   8400
gagagaaaaa gcaccgtgca tgccgattgg tggaagtaag gtggtacgat cgtgccttat   8460
taggaaggca acagacgggt ctgacatgga ttggacgaac cactgaattc cgcattgcag   8520
agatattgta tttaagtgcc tagctcgata caataaacgc catttgacca ttcaccacat   8580
tggtgtgcac catggtgacc ggcggcatgg cctccaagtg ggatcaaaag ggcatggata   8640
tcgcttacga ggaggccctg ctgggctaca aggagggcgg cgtgcctatc ggcggctgtc   8700
tgatcaacaa caaggacggc agtgtgctgg gcaggggcca caacatgagg ttccagaagg   8760
gctccgccac cctgcacggc gagatctcca ccctggagaa ctgtggcagg ctggagggca   8820
aggtgtacaa ggacaccacc ctgtacacca ccctgtcccc ttgtgacatg tgtaccggcg   8880
ctatcatcat gtacggcatc cctaggtgtg tgatcggcga gaacgtgaac ttcaagtcca   8940
agggcgagaa gtacctgcaa accaggggcc acgaggtggt ggttgttgac gatgagaggt   9000
gtaagaagct gatgaagcag ttcatcgacg agaggcctca ggactggttc gaggatatcg   9060
gcgagtaatg aggatcctgc tcgcttcggc agcacatata ctagtcgact agggataaca   9120
gggtaattgt ttgaatgagg cttcagtact ttacagaatc gttgcctgca catcttggaa   9180
acacttgctg ggattacttc ttcaggttaa cccaacagaa ggctcgagaa ggtatattgc   9240
tgttgacagt gagcgcggta gcaatatgac aattgatagt gaagccacag atgtatcaat   9300
tgtcatattg ctaccatgcc tactgcctcg gaattcaagg ggctacttta ggagcaatta   9360
tcttgtttac taaaactgaa taccttgcta tctctttgat acatttttac aaagctgaat   9420
taaaatggta taaattaaat cacttttttc aattggaaga ctaatgcggc ggccgcagat   9480
aaaataaaag attttattta gtctccagaa aaagggggga atgaaagacc ccacctgtag   9540
gtttggcaag ctagcttaag taacgccatt ttgcaaggca tggaaaaata cataactgag   9600
```

```
aatagagaag ttcagatcaa ggtcaggaac agatggaaca gctgaatatg ggccaaacag   9660
gatatctgtg gtaagcagtt cctgccccgg ctcagggcca agaacagatg gaacagctga   9720
atatgggcca aacaggatat ctgtggtaag cagttcctgc cccggctcag ggccaagaac   9780
agatggtccc cagatgcggt ccagccctca gcagtttcta gagaaccatc agatgtttcc   9840
agggtgcccc aaggacctga aatgaccctg tgccttattt gaactaacca atcagttcgc   9900
ttctcgcttc tgttcgcgcg cttctgctcc ccgagctcaa taaaagagcc cacaacccct   9960
cactcggggc gccagtcctc cgattgactg agtcgcccgg gtacccgtgt atccaataaa  10020
ccctcttgca gttgcatccg acttgtggtc tcgctgttcc ttgggagggt ctcctctgag  10080
tgattgacta cccgtcagcg ggggtctttc attacatgtg agcaaaaggc cagcaaaagg  10140
ccaggaaccg taaaaaggcc gcgttgctgg cgtttttcca taggctccgc ccccctgacg  10200
agcatcacaa aaatcgacgc tcaagtcaga ggtggcgaaa cccgacagga ctataaagat  10260
accaggcgtt tccccctgga agctccctcg tgcgctctcc tgttccgacc ctgccgctta  10320
ccggatacct gtccgccttt ctcccttcgg gaagcgtggc gctttctcat agctcacgct  10380
gtaggtatct cagttcggtg taggtcgttc gctccaagct gggctgtgtg cacgaacccc  10440
ccgttcagcc cgaccgctgc gccttatccg gtaactatcg tcttgagtcc aacccggtaa  10500
gacacgactt atcgccactg gcagcagcca ctggtaacag gattagcaga gcgaggtatg  10560
taggcggtgc tacagagttc ttgaagtggt ggcctaacta cggctacact agaaggacag  10620
tatttggtat ctgcgctctg ctgaagccag ttaccttcgg aaaaagagtt ggtagctctt  10680
gatccggcaa acaaaccacc gctggtagcg gtggtttttt tgtttgcaag cagcagatta  10740
cgcgcagaaa aaaaggatct caagaagatc ctttgatctt ttctacgggg tctgacgctc  10800
agtggaacga aaactcacgt taagggattt tggtcatgag attatcaaaa aggatcttca  10860
cctagatcct tttaaattaa aaatgaagtt ttaaatcaat ctaaagtata tatgagtaaa  10920
cttggtctga cagttaccaa tgcttaatca gtgaggcacc tatctcagcg atctgtctat  10980
ttcgttcatc catagttgcc tgactccccg tcgtgtagat aactacgata cgggagggct  11040
taccatctgg ccccagtgct gcaatgatac cgcgagaccc acgctcaccg gctccagatt  11100
tatcagcaat aaaccagcca gccggaaggg ccgagcgcag aagtggtcct gcaactttat  11160
ccgcctccat ccagtctatt aattgttgcc gggaagctag agtaagtagt tcgccagtta  11220
atagtttgcg caacgttgtt gccattgctg caggcatcgt ggtgtcacgc tcgtcgtttg  11280
gtatggcttc attcagctcc ggttcccaac gatcaaggcg agttacatga tcccccatgt  11340
tgtgcaaaaa agcggttagc tccttcggtc ctccgatcgt tgtcagaagt aagttggccg  11400
cagtgttatc actcatggtt atggcagcac tgcataattc tcttactgtc atgccatccg  11460
taagatgctt ttctgtgact ggtgagtact caaccaagtc attctgagaa tagtgtatgc  11520
ggcgaccgag ttgctcttgc ccggcgtcaa cacgggataa taccgcgcca catagcagaa  11580
ctttaaaagt gctcatcatt ggaaaacgtt cttcggggcg aaaactctca aggatcttac  11640
cgctgttgag atccagttcg atgtaaccca ctcgtgcacc caactgatct tcagcatctt  11700
ttactttcac cagcgtttct gggtgagcaa aaacaggaag gcaaaatgcc gcaaaaaagg  11760
gaataagggc gacacggaaa tgttgaatac tcatactctt cctttttcaa tattattgaa  11820
gcatttatca gggttattgt ctcatgagcg gatacatatt tgaatgtatt tagaaaaata  11880
aacaaatagg ggttccgcgc acatttcccc gaaaagtgcc acctgacgtc taagaaacca  11940
ttattatcat gacattaacc tataaaaata ggcgtatcac gaggcccttt cgtcttcaag  12000
```

aattccat 12008

<210> SEQ ID NO 16
<211> LENGTH: 12273
<212> TYPE: DNA
<213> ORGANISM: Artificial Sequence
<220> FEATURE:
<223> OTHER INFORMATION: Vector pAC3-RSV-yCD2-U6-PDL1miR30shRNA4

<400> SEQUENCE: 16
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440
tcccctacat cgtgacctgg gaagccttgg cttttgaccc ccctccctgg gtcaagccct 1500
ttgtacaccc taagcctccg cctcctcttc ctccatccgc cccgtctctc ccccttgaac 1560
ctcctcgttc gaccccgcct cgatcctccc tttatccagc cctcactcct tctctaggcg 1620
ccaaacctaa acctcaagtt ctttctgaca gtggggggcc gctcatcgac ctacttacag 1680
aagacccccc gccttatagg gacccaagac caccccttc cgacagggac ggaaatggtg 1740
gagaagcgac ccctgcggga gaggcaccgg acccctcccc aatggcatct cgcctacgtg 1800
ggagacggga gccccctgtg gccgactcca ctacctcgca ggcattcccc ctccgcgcag 1860
gaggaaacgg acagcttcaa tactggccgt tctcctcttc tgacctttac aactggaaaa 1920
ataataaccc ttctttttct gaagatccag gtaaactgac agctctgatc gagtctgtcc 1980

```
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg ggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
```

```
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
```

```
tggggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc    6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagcccct caataccagt tacccccctt ccactaccag    7200
tacaccctca acctccccta caagtccaag tgtcccacag ccaccccccag gaactggaga  7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta atgtagtctt   8340
atgcaatact cttgtagtct tgcaacatgg taacgatgag ttagcaacat gccttacaag   8400
gagagaaaaa gcaccgtgca tgccgattgg tggaagtaag gtggtacgat cgtgccttat   8460
taggaaggca acagacgggt ctgacatgga ttggacgaac cactgaattc cgcattgcag   8520
agatattgta tttaagtgcc tagctcgata caataaacgc catttgacca ttcaccacat   8580
tggtgtgcac catggtgacc ggcggcatgg cctccaagtg ggatcaaaag ggcatggata   8640
tcgcttacga ggaggccctg ctgggctaca aggagggcgg cgtgcctatc ggcggctgtc   8700
tgatcaacaa caaggacggc agtgtgctgg gcaggggcca caacatgagg ttccagaagg   8760
gctccgccac cctgcacggc gagatctcca ccctggagaa ctgtggcagg ctggagggca   8820
aggtgtacaa ggacaccacc ctgtacacca ccctgtcccc ttgtgacatg tgtaccggcg   8880
ctatcatcat gtacggcatc cctaggtgtg tgatcggcga gaacgtgaac ttcaagtcca   8940
agggcgagaa gtacctgcaa accaggggcc acgaggtggt ggttgttgac gatgagaggt   9000
gtaagaagct gatgaagcag ttcatcgacg agaggcctca ggactggttc gaggatatcg   9060
gcgagtaatg aaaggtcggg caggaagagg gcctatttcc catgattcct tcatatttgc   9120
```

```
atatacgata caaggctgtt agagagataa ttagaattaa tttgactgta aacacaaaga   9180
tattagtaca aaatacgtga cgtagaaagt aataatttct tgggtagttt gcagttttta   9240
aaattatgtt ttaaaatgga ctatcatatg cttaccgtaa cttgaaagta tttcgatttc   9300
ttggctttat atatcttgtg gaaaggacga aacaccggat cctgctcgct tcggcagcac   9360
atatactagt cgactaggga taacagggta attgtttgaa tgaggcttca gtactttaca   9420
gaatcgttgc ctgcacatct tggaaacact tgctgggatt acttcttcag gttaacccaa   9480
cagaaggctc gagaaggtat attgctgttg acagtgagcg cggtagcaat atgacaattg   9540
atagtgaagc cacagatgta tcaattgtca tattgctacc atgcctactg cctcggaatt   9600
caaggggcta ctttaggagc aattatcttg tttactaaaa ctgaatacct tgctatctct   9660
ttgatacatt tttacaaagc tgaattaaaa tggtataaat taaatcactt ttttcaattg   9720
gaagactaat gcggcggccg cagataaaat aaaagatttt atttagtctc cagaaaaagg   9780
ggggaatgaa agaccccacc tgtaggtttg gcaagctagc ttaagtaacg ccattttgca   9840
aggcatggaa aaatacataa ctgagaatag agaagttcag atcaaggtca ggaacagatg   9900
gaacagctga atatgggcca aacaggatat ctgtggtaag cagttcctgc cccggctcag   9960
ggccaagaac agatggaaca gctgaatatg ggccaaacag gatatctgtg gtaagcagtt  10020
cctgccccgg ctcagggcca agaacagatg gtccccagat gcggtccagc cctcagcagt  10080
ttctagagaa ccatcagatg tttccagggt gccccaagga cctgaaatga ccctgtgcct  10140
tatttgaact aaccaatcag ttcgcttctc gcttctgttc gcgcgcttct gctccccgag  10200
ctcaataaaa gagcccacaa cccctcactc ggggcgccag tcctccgatt gactgagtcg  10260
cccgggtacc cgtgtatcca ataaaccctc ttgcagttgc atccgacttg tggtctcgct  10320
gttccttggg agggtctcct ctgagtgatt gactacccgt cagcgggggt ctttcattac  10380
atgtgagcaa aaggccagca aaaggccagg aaccgtaaaa aggccgcgtt gctggcgttt  10440
ttccataggc tccgcccccc tgacgagcat cacaaaaatc gacgctcaag tcagaggtgg  10500
cgaaacccga caggactata aagataccag gcgtttcccc ctggaagctc cctcgtgcgc  10560
tctcctgttc cgaccctgcc gcttaccgga tacctgtccg cctttctccc ttcgggaagc  10620
gtggcgcttt ctcatagctc acgctgtagg tatctcagtt cggtgtaggt cgttcgctcc  10680
aagctgggct gtgtgcacga accccccgtt cagcccgacc gctgcgcctt atccggtaac  10740
tatcgtcttg agtccaaccc ggtaagacac gacttatcgc cactggcagc agccactggt  10800
aacaggatta gcagagcgag gtatgtaggc ggtgctacag agttcttgaa gtggtggcct  10860
aactacggct acactagaag gacagtattt ggtatctgcg ctctgctgaa gccagttacc  10920
ttcggaaaaa gagttggtag ctcttgatcc ggcaaacaaa ccaccgctgg tagcggtggt  10980
tttttgttt gcaagcagca gattacgcgc agaaaaaaag gatctcaaga agatcctttg  11040
atcttttcta cggggtctga cgctcagtgg aacgaaaact cacgttaagg gattttggtc  11100
atgagattat caaaaaggat cttcacctag atccttttaa attaaaaatg aagttttaaa  11160
tcaatctaaa gtatatatga gtaaacttgg tctgacagtt accaatgctt aatcagtgag  11220
gcacctatct cagcgatctg tctatttcgt tcatccatag ttgcctgact ccccgtcgtg  11280
tagataacta cgatacggga gggcttacca tctggcccca gtgctgcaat gataccgcga  11340
gacccacgct caccggctcc agatttatca gcaataaacc agccagccgg aagggccgag  11400
cgcagaagtg gtcctgcaac tttatccgcc tccatccagt ctattaattg ttgccgggaa  11460
```

```
gctagagtaa gtagttcgcc agttaatagt ttgcgcaacg ttgttgccat tgctgcaggc  11520

atcgtggtgt cacgctcgtc gtttggtatg gcttcattca gctccggttc ccaacgatca  11580

aggcgagtta catgatcccc catgttgtgc aaaaaagcgg ttagctcctt cggtcctccg  11640

atcgttgtca gaagtaagtt ggccgcagtg ttatcactca tggttatggc agcactgcat  11700

aattctctta ctgtcatgcc atccgtaaga tgcttttctg tgactggtga gtactcaacc  11760

aagtcattct gagaatagtg tatgcggcga ccgagttgct cttgcccggc gtcaacacgg  11820

gataataccg cgccacatag cagaacttta aaagtgctca tcattggaaa acgttcttcg  11880

gggcgaaaac tctcaaggat cttaccgctg ttgagatcca gttcgatgta acccactcgt  11940

gcacccaact gatcttcagc atcttttact ttcaccagcg tttctgggtg agcaaaaaca  12000

ggaaggcaaa atgccgcaaa aaagggaata agggcgacac ggaaatgttg aatactcata  12060

ctcttccttt ttcaatatta ttgaagcatt tatcagggtt attgtctcat gagcggatac  12120

atatttgaat gtatttagaa aaataaacaa ataggggttc cgcgcacatt tccccgaaaa  12180

gtgccacctg acgtctaaga aaccattatt atcatgacat taacctataa aaataggcgt  12240

atcacgaggc cctttcgtct tcaagaattc cat                                12273
```

<210> SEQ ID NO 17
<211> LENGTH: 31
<212> TYPE: DNA
<213> ORGANISM: Artificial Sequence
<220> FEATURE:
<223> OTHER INFORMATION: SALI-IRES Forward Primer

<400> SEQUENCE: 17

```
gtacgtcgac tactggccga agccgcttgg a                                    31
```

<210> SEQ ID NO 18
<211> LENGTH: 32
<212> TYPE: DNA
<213> ORGANISM: Artificial Sequence
<220> FEATURE:
<223> OTHER INFORMATION: ClaI-yCD2-Reverse Primer

<400> SEQUENCE: 18

```
gtacatcgat ttactcgccg atatcctcga ac                                   32
```

<210> SEQ ID NO 19
<211> LENGTH: 32
<212> TYPE: DNA
<213> ORGANISM: Artificial Sequence
<220> FEATURE:
<223> OTHER INFORMATION: ClaI-hIL-2-Reverse Primer

<400> SEQUENCE: 19

```
gtacatcgat tcaagtcagt gttgagatga tg                                   32
```

<210> SEQ ID NO 20
<211> LENGTH: 32
<212> TYPE: DNA
<213> ORGANISM: Artificial Sequence
<220> FEATURE:
<223> OTHER INFORMATION: ClaI-mIL-2-Reverse Primer

<400> SEQUENCE: 20

```
gtacatcgat ttattgaggg cttgttgaga tg                                   32
```

<210> SEQ ID NO 21
<211> LENGTH: 33

<212> TYPE: DNA
<213> ORGANISM: Artificial Sequence
<220> FEATURE:
<223> OTHER INFORMATION: hU6-NotI Forward Primer

<400> SEQUENCE: 21
gatcgcggcc gcacgcgtaa ggtcgggcag gaa 33

<210> SEQ ID NO 22
<211> LENGTH: 22
<212> TYPE: DNA
<213> ORGANISM: Artificial Sequence
<220> FEATURE:
<223> OTHER INFORMATION: shRNA-NotI-Reverse Primer

<400> SEQUENCE: 22
atctgcggcc gcctagaaaa aa 22

<210> SEQ ID NO 23
<211> LENGTH: 27
<212> TYPE: DNA
<213> ORGANISM: Artificial Sequence
<220> FEATURE:
<223> OTHER INFORMATION: miR30-NotI-Reverse Primer

<400> SEQUENCE: 23
gcggccgccg cattagtctt ccaattg 27

<210> SEQ ID NO 24
<211> LENGTH: 19
<212> TYPE: DNA
<213> ORGANISM: Artificial Sequence
<220> FEATURE:
<223> OTHER INFORMATION: IDO-1 siRNA sequence

<400> SEQUENCE: 24
tattctatag tcttacttg 19

<210> SEQ ID NO 25
<211> LENGTH: 19
<212> TYPE: DNA
<213> ORGANISM: Artificial Sequence
<220> FEATURE:
<223> OTHER INFORMATION: IDO-1 siRNA sequence

<400> SEQUENCE: 25
tcaacttctt ctcgaagct 19

<210> SEQ ID NO 26
<211> LENGTH: 19
<212> TYPE: DNA
<213> ORGANISM: Artificial Sequence
<220> FEATURE:
<223> OTHER INFORMATION: IDO-1 siRNA sequence

<400> SEQUENCE: 26
tgaaatgaca aactcacgg 19

<210> SEQ ID NO 27
<211> LENGTH: 19
<212> TYPE: DNA
<213> ORGANISM: Artificial Sequence
<220> FEATURE:
<223> OTHER INFORMATION: PDL-1 siRNA sequence

<400> SEQUENCE: 27
tagttcatgc tcagaagtg 19

<210> SEQ ID NO 28
<211> LENGTH: 19
<212> TYPE: DNA
<213> ORGANISM: Artificial Sequence
<220> FEATURE:
<223> OTHER INFORMATION: PDL-1 siRNA sequence

<400> SEQUENCE: 28
aatgctagac aatgaactg 19

<210> SEQ ID NO 29
<211> LENGTH: 19
<212> TYPE: DNA
<213> ORGANISM: Artificial Sequence
<220> FEATURE:
<223> OTHER INFORMATION: PDL-1 siRNA sequence

<400> SEQUENCE: 29
tatgcagcag taaacgcct 19

<210> SEQ ID NO 30
<211> LENGTH: 19
<212> TYPE: DNA
<213> ORGANISM: Artificial Sequence
<220> FEATURE:
<223> OTHER INFORMATION: PDL-1 siRNA sequence

<400> SEQUENCE: 30
agtccgcacc accgtagct 19

<210> SEQ ID NO 31
<211> LENGTH: 19
<212> TYPE: DNA
<213> ORGANISM: Artificial Sequence
<220> FEATURE:
<223> OTHER INFORMATION: TGFb2 siRNA sequence

<400> SEQUENCE: 31
ttgtggtgaa gccactcct 19

<210> SEQ ID NO 32
<211> LENGTH: 19
<212> TYPE: DNA
<213> ORGANISM: Artificial Sequence
<220> FEATURE:
<223> OTHER INFORMATION: TGFb2 siRNA sequence

<400> SEQUENCE: 32
tctcctgcag taagtccct 19

<210> SEQ ID NO 33
<211> LENGTH: 19
<212> TYPE: DNA
<213> ORGANISM: Artificial Sequence
<220> FEATURE:
<223> OTHER INFORMATION: TGFb2 siRNA sequence

<400> SEQUENCE: 33
aacaaacaga acacaagct 19

RETROVIRAL VECTOR HAVING IMMUNE-STIMULATING ACTIVITY

CROSS REFERENCE TO RELATED APPLICATIONS

This application is a U.S. National Stage Application filed under 35 U.S.C. § 371 and claims priority to International Application No. PCT/US2015/022512, filed Mar. 25, 2015, which application claims priority to U.S. Provisional Application Serial No. 61/970,823, filed Mar. 26, 2014, the disclosures of which are incorporated herein by reference.

TECHNICAL FIELD

This disclosure relates to cancer therapy and more specifically to inhibiting the growth of a tumor utilizing various vector constructs.

BACKGROUND

Cancer accounts for a large portion of morbidity and mortality in the United States, and is the second leading cause of death. Cancer is typically characterized by the uncontrolled division of a population of cells. This uncontrolled division typically leads to the formation of a tumor, which may subsequently metastasize to other sites. There is a need for additional cancer therapeutics and strategies to not only treat solid tumors but the micrometastases that occur during cancer progression.

SUMMARY

The disclosure provides a recombinant retroviral vector comprising at least one expression cassette comprising at least one agent that down regulates an immune inhibitory agent. In one embodiment, the vector comprises at least two cassettes. In a further embodiment, the recombinant retroviral vector comprises two agents that down regulate an immune inhibitory agent. In any of the foregoing embodiments, the at least one agent comprises a polynucleotide encoding a single-chain antibody and/or an inhibitory nucleic acid sequence. In still other embodiments of the foregoing, the at least one agent comprises an inhibitory nucleic acid sequence and a polynucleotide encoding a polypeptide having cytosine deaminase activity. In still further embodiments of any of the foregoing embodiments, the at least one agent comprises an inhibitory nucleic acid sequence and wherein the vector further comprises a second agent selected from the group consisting of (i) a second inhibitory nucleic acid sequence, (ii) a polynucleotide encoding a single-chain antibody, (iii) a polynucleotide encoding an polypeptide the converts a prodrug to a cytotoxic drug, and (iv) a polynucleotide encoding a cytokine or chemokine. In another embodiment, a first cassette comprises a polIII promoter operably linked to an inhibitory nucleic acid sequence; and a second cassette comprises a mini-promoter operably linked to a polynucleotide encoding a polypeptide having cytosine deaminase or a single chain antibody. In yet another embodiment, a first cassette comprises a polIII promoter operably linked to a first inhibitory nucleic acid sequence; and a second cassette comprises a mini-promoter operably linked to a second inhibitory nucleic acid sequence. In yet another embodiment of any of the foregoing, the retroviral vector is replication competent. In an alternative embodiment, the retroviral vector is replication defective. In one embodiment, the replication competent retroviral vector comprises the general structure from 5' to 3' comprising a long terminal repeat (LTR)-gag sequence-pol sequence-env sequence-(at least one expression cassette)-LTR. In a further embodiment, the vector comprises a retroviral polynucleotide sequence derived from murine leukemia virus (MLV), Moloney murine leukemia virus (MoMLV), Feline leukemia virus (FeLV) or Gibbon ape leukemia virus (GALV). In still a further embodiment, the MLV is an amphotropic MLV. In yet another embodiment of the replication competent retroviral vector the vector comprises: a retroviral GAG protein; a retroviral POL protein; a retroviral envelope; a retroviral polynucleotide comprising: Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain; and an env nucleic acid domain; at least one cassette comprising a heterologous nucleic acid sequence, wherein the cassette is positioned 5' to the 3' LTR and 3' to the env nucleic acid domain encoding the retroviral envelope; and cis-acting sequences necessary for reverse transcription, packaging and integration in a target cell. In a further embodiment, the promoter comprises a CMV promoter having a sequence as set forth in SEQ ID NO:1-15 or 16 from nucleotide 1 to about nucleotide 582 and may include modification to one or more nucleic acid bases and which is capable of directing and initiating transcription. In yet a further embodiment, the promoter comprises a sequence as set forth in SEQ ID NO: 1-15 or 16 from nucleotide 1 to about nucleotide 582. In still a further embodiment, the promoter comprises a CMV-R-U5 domain polynucleotide. In yet another embodiment, the CMV-R-U5 domain comprises the immediately early promoter from human cytomegalovirus linked to an MLV R-U5 region. In yet a further embodiment, the CMV-R-U5 domain polynucleotide comprises a sequence as set forth in SEQ ID NO: 1-15 or 16 from about nucleotide 1 to about nucleotide 1202 or sequences that are at least 95% identical to a sequence as set forth in SEQ ID NO: 1-15 or 16 from nucleotide 1 to about nucleotide 1202, wherein the polynucleotide promotes transcription of a nucleic acid molecule operably linked thereto. In another embodiment, the gag nucleic acid domain comprises a sequence from about nucleotide number 1203 to about nucleotide 2819 of SEQ ID NO: 1-15 or 16 or a sequence having at least 95%, 98%, 99% or 99.8% identity thereto. In still another embodiment, the pol domain can comprise a sequence from about nucleotide number 2820 to about nucleotide 6358 of SEQ ID NO: 1-15 or 16 or a sequence having at least 95%, 98%, 99% or 99.9% identity thereto. In a further embodiment, the env domain encodes an amphotropic env protein. In yet a further embodiment, the env domain can comprise a sequence from about nucleotide number 6359 to about nucleotide 8323 of SEQ ID NO: 1-15 or 16 or a sequence having at least 95%, 98%, 99% or 99.8% identity thereto. In another embodiment, the at least one cassette comprises a polIII promoter operably linked to an inhibitory nucleic acid sequence such that the inhibitory nucleic acid sequence is expressed. In a further embodiment, the polIII promoter comprises an H1 promoter or a U6 promoter. In a further embodiment, the H1 promoter comprises a sequence as set forth in SEQ ID NO:7 or 12 from about 8330 to 8553 and comprises polIII termination sequences from about 8885 to 8889 and 8925 to 8930. In another embodiment, the U6 promoter comprises a sequence as set forth in SEQ ID NO:8 or 13 from about 8330-8595 and comprises polIII termination sequence from about 8922-8926 and 8962 to 8967. In another embodiment, the at least one cassette comprises a mini-promoter. In a further embodiment, the mini-promoter is an RSV promoter. In still a further embodiment, the RSV promoter comprises a sequence from about 8330 to about 8591 of SEQ ID NO:9, 10, 14, 15, or 16. In yet another embodiment, the RSV promoter is operably linked to an inhibitory nucleic acid sequence. In another embodiment, the RSV promoter is operably linked to a polynucleotide encoding a polypeptide having cytosine deaminase activity. In still another embodiment, the RSV promoter is operably linked to a polynucleotide encoding a polypeptide having cytosine deaminase followed by and operably linked to an inhibitory nucleic acid sequence. In yet another embodiment of the foregoing, the at least one cassette comprises two cassettes. In a further embodiment, a first cassette comprises an H1 or U6 promoter linked to an inhibitory nucleic acid sequence and the second cassette comprises an RSV promoter operably linked to a polynucleotide encoding a polypeptide. In a specification embodiment, the vector comprises a sequence selected from the group consisting of SEQ ID NO: 7-15 and 16. In yet another embodiment, wherein the vector comprises a cassette encoding a polypeptide, the polynucleotide that encodes the polypeptide is human codon optimized. In still another embodiment, the polypeptide having cytosine deaminase activity is heat stabilized. In yet another embodiment, the inhibitory nucleic acid sequence inhibits PDL1 or IDO1. In another embodiment, when the vector is replication defective, the vector comprises the following structure when in linear form from 5' to 3': a 5'LTR, a primer binding site for reverse transcriptase (PBS), an optional 5' splice site; Psi (Ψ) packaging signal, mutated gag gene comprising sufficient sequences for packaging and integration but lacking a functional start site, at least one cassette, a polypurine tract and a 3'LTR (U3-R-U5). In a further embodiment, the vector comprises at least two cassettes. In still another embodiment, at least one of the at least two cassettes comprises an interferon-γ gene (IFNγ). In a further embodiment, at least one of the cassettes comprises a polynucleotide that encodes a polypeptide having cytosine deaminase activity. In another embodiment, at least one cassette comprises an inhibitory nucleic acid sequence and the heterologous sequence is preceded by a polIII promoter or RSV promoter.

The disclosure also provides a method of treating a cancer or cell proliferative disorder comprising contacting a subject with the cancer of cell proliferative disorder with a recombinant retroviral vector as described herein.

The disclosure also provides a method of treating a cancer or cell proliferative disorder comprising contacting a subject with the cancer of cell proliferative disorder with a recombinant retroviral vector described herein, that comprises a cytosine deaminase gene, and additionally treating the subject with 5-fluorocytosine.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

Like reference symbols in the various drawings indicate like elements.

DETAILED DESCRIPTION

Figure 1A:
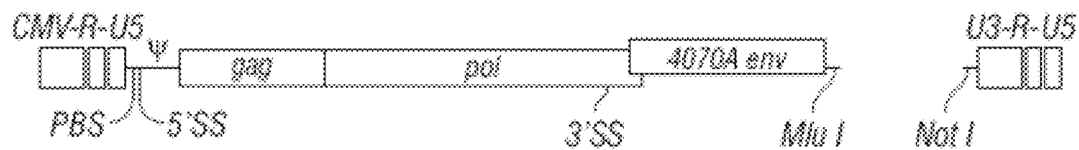
FIG. 1A-C shows schematic constructs of the disclosure. (A) Shows an RRV backbone with a MluI/NotI cloning site for insertion of a cassette containing a pri-miRNA or a pri-miRNA driven by an H1 promoter. (B) Shows a pAC3-yCD2 backbone with an IRES or RSV promoter cassette with a NotI cloning site for insertion of a cassette comprising an H1 promoter driving a pre-miRNA. (C) Shows a pAC3 backbone with an IRES or RSV promoter cassette linked to an antibody (e.g., a single chain antibody (scAB) and a NotI cloning site for optional cassette comprising an H1 promoter driving an pre-miRNA.

As used herein and in the appended claims, the singular forms “a,” “and,” and “the” include plural referents unless the context clearly dictates otherwise. Thus, for example, reference to “a cell” includes a plurality of such cells and reference to “the agent” includes reference to one or more agents known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous cell cancer, malignant melanoma, sinonasal undifferentiated carcinoma (SNUC), brain (including glioblastomas) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp 1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer, skin cancer and ovarian cancer.

The term "codon optimized sequences" generally refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

As used herein, a "core promoter" refers to a minimal promoter comprising about 50-100 bp and lacks enhancer elements. Such core promoters include, but are not limited to, SCP1, AdML and CMV core promoters. More particularly, where a core-promoter cassette is present a second cassette (e.g., a second mini-promoter cassette, a polIII promoter cassette or IRES cassette) will be present. In some embodiments, a vector comprising a cassette with a core promoter specifically excludes the use of SCP1, AdML and CMV core promoters, but rather utilize designer core promoters as described further herein and below.

Core promoters include certain viral promoters. Viral promoters, as used herein, are promoters that have a core sequence but also usually some further accessory elements. For example, the early promoter for SV40 contains three types of elements: a TATA box, an initiation site and a GC repeat (Barrera-Saldana et al., EMBO J, 4:3839-3849, 1985; Yaniv, Virology, 384:369-374, 2009). The TATA box is located approximately 20 base-pairs upstream from the transcriptional start site. The GC repeat regions is a 21 base-pair repeat containing six GC boxes and is the site that determines the direction of transcription. This core promoter sequence is around 100 bp. Adding an additional 72 base-pair repeats, thus making it a "mini-promoter," is useful as a transcriptional enhancer that increase the functionality of the promoter by a factor of about 10. When the SP1 protein interacts with the 21 bp repeats it binds either the first or the last three GC boxes. Binding of the first three initiates early expression, and binding of the last three initiates late expression. The function of the 72 bp repeats is to enhance the amount of stable RNA and increase the rate of synthesis. This is done by binding (dimerization) with the AP1 (activator protein 1) to give a primary transcript that is 3' polyadenylated and 5' capped. Other viral promoters, such as the Rous Sarcom Virus (RSV), the HBV X gene promoter, and the Herpes Thymidine kinase core promoter can also be used as the basis for selection desired function.

A core promoter typically encompasses −40 to +40 relative to the +1 transcription start site (Juven-Gershon and Kadonaga, Dev. Biol. 339:225-229, 2010), which defines the location at which the RNA polymerase II machinery initiates transcription. Typically, RNA polymerase II interacts with a number of transcription factors that bind to DNA motifs in the promoter. These factors are commonly known as "general" or "basal" transcriptions factors and include, but are not limited to, TFIIA (transcription factor for RNA polymerase IIA), TFIIB, TFIID, TFIIE, TFIIF, and TFIIH. These factors act in a "general" manner with all core promoters; hence they are often referred to as the "basal" transcription factors. See PCT Publication No. WO2014/066700, which is incorporated herein by reference and which further describes core promoters useful in the methods and compositions of the disclosure.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells.

As used herein, the term "heterologous" nucleic acid sequence or transgene refers to (i) a sequence that does not normally exist in a wild-type retrovirus, (ii) a sequence that originates from a foreign species, or (iii) if from the same species, it may be substantially modified from its original form. Alternatively, an unchanged nucleic acid sequence that is not normally expressed in a cell or carried by a virus is a heterologous nucleic acid sequence. In a specific embodiment, the heterologous polynucleotide is (i) a polypeptide of the disclosure having cytosine deaminase activity or (ii) a polynucleotide that comprises RNAi activity.

The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As used herein a "mini-promoter" or "small promoter" refers to a regulatory domain that promotes transcription of an operably linked gene or coding nucleic acid sequence. The mini-promoter, as the name implies, includes the minimal amount of elements necessary for effective transcription and/or translation of an operably linked coding sequence. A mini-promoter can comprise a "core promoter" in combination with additional regulatory elements or a "modified core promoter". Typically, the mini-promoter or modified core promoter will be about 100-600 bp in length while a core promoter is typically less than about 100 bp (e.g., about 70-80 bp). In other embodiments, where a core promoter is present, the cassette will typically comprise an enhancer element or another element either upstream or downstream of the core promoter sequence that facilitates expression of an operably linked coding sequence above the expression levels of the core promoter alone. Ubiquitously expressed small promoters also include viral promoters such as the SV40 early and late promoters (about 340 bp), the RSV LTR promoter (about 270 bp) and the HBV X gene promoter (about 180 bp). See PCT Publication No. WO2014/066700, which is incorporated herein by reference and which further describes mini-promoters useful in the methods and compositions of the disclosure.

The phrase "non-dividing" cell refers to a cell that does not go through mitosis. Non-dividing cells may be blocked at any point in the cell cycle, (e.g., $G_0/G_1$, $G_{1/S}$, $G_{2/M}$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). For example, a recombinant lentivirus vector is capable of infecting non-dividing cell. Examples of pre-existing non-dividing cells in the body include neuronal, muscle, liver, skin, heart, lung, and bone marrow cells, and their derivatives. For dividing cells onco-retroviral vectors can be used.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter as described herein.

The term "regulatory nucleic acid sequence" refers collectively to promoter sequences, polyadenylation signals, transcription termination sequences, upstream regulatory domains, origins of replication, enhancers and the like, which collectively provide for the replication, transcription and translation of a coding sequence in a recipient cell. Not all of these control sequences need always be present so long as the selected coding sequence is capable of being replicated, transcribed and translated in an appropriate host cell. One skilled in the art can readily identify regulatory nucleic acid sequence from public databases and materials. Furthermore, one skilled in the art can identify a regulatory sequence that is applicable for the intended use, for example, in vivo, ex vivo, or in vitro.

Primary solid tumors are generally treated by surgical resection. However, the majority of patients which have solid tumors also possess micrometastases beyond the primary tumor site. If treated with surgery alone, approximately 70% of these patients will experience recurrence of the cancer. In addition to surgery, many cancers are now also treated with a combination of therapies involving cytotoxic chemotherapeutic drugs (e.g., Vincristine, vinblastine, cisplatin, methotrexate, 5-FU, etc.) and/or radiation therapy. One difficulty with this approach however, is that radiotherapeutic and chemotherapeutic agents are toxic to normal tissues, and often create life-threatening side effects. In addition, these approaches often have extremely high failure/remission rates (up to 90% depending upon the type of cancer).

Despite many years of research and development of newer treatment modalities, cancer remains the second leading cause of death in the USA, and a major scourge world-wide. Modulation of the immune response has been recognized for some time as a potential new therapeutic target for cancer therapy (Franks, H. A., Q. Wang, and P. M. Patel, *New anticancer immunotherapies*. Anticancer Res, 2012. 32: 2439-53).

Several immunotherapies have utilized bacterial or viral components as adjuvants, in order to stimulate the immune system to destroy the tumor cells. Examples of such components include BCG, endotoxin, mixed bacterial vaccines, interferons (α, β and γ), interferon inducers (e.g., *Brucella abortus*, and various viruses), and thymic factors (e.g., thymosin fraction 5, and thymosin alpha-1) (see generally "Principles of Cancer Biotherapy," Oldham (ed.), Raven Press, New York, 1987). Such agents have generally been useful as adjuvants and as nonspecific stimulants in animal tumor models, but have not yet proved to be generally effective in humans.

Lymphokines have also been utilized in the treatment of cancer. Briefly, lymphokines are secreted by a variety of cells, and generally have an effect on specific cells in the generation of an immune response. Examples of lymphokines include Interleukins (IL)-1, -2, -3, and -4, as well as colony stimulating factors such as G-CSF, GM-CSF, and M-CSF. One group utilized IL-2 to stimulate peripheral blood cells in order to expand and produce large quantities of cells which are cytotoxic to tumor cells (Rosenberg et al., N. Engl. J. Med. 313:1485-1492, 1985).

However, even in view of the cited methodologies above, current immune modulating therapies have met with limited success in clinical trials (Zhou, G. and H. Levitsky, *Towards curative cancer immunotherapy: overcoming posttherapy tumor escape*. Clin Dev Immunol, 2012. 2012: p. 12418) One of the reasons for the unexpectedly poor clinical outcomes from these therapies is likely due to the mono-therapeutic approach most immunotherapies rely on for efficacy when immune escape involves multiple mechanisms creating a tumor-immunosuppressive environment (Rolle et al., *Mechanisms of immune evasion by gliomas*. Adv Exp Med Biol, 746:53-76, 2012; Hong and Zeng, *Awaiting a new era of cancer immunotherapy*. Cancer Res, 72:3715-9, 2012; Ichim et al., *Exosomes as a tumor immune escape mechanism: possible therapeutic implications*. J Transl Med, 6:37, 2008).

Many tumors express or secrete a number of immunosuppressive molecules (Gajewski et al., Nature Immunol. 14:1014-1022, 2013; Motz G T. and Coukos G., immunity, 39:61-73, 2013) including PD-L1, PD-L2, IDO-1 and 2, CD31, Tim3, Prostoglandin E2 (PGE2), IL-6, IL-10, VEGF, HLA G, FasL, IL-10, adenosine and TGF-β1, 2 and 3, in order to escape the anti-tumor immune responses (Avril et al., Journal of Neuroimmunology 225:22-33, 2010). These molecules suppress T cell proliferation, inhibit T cell activation and differentiation into cytotoxic effector cells, or trigger T cells apoptosis. Immune escape is a central process for oncogenic success and plays a role in the development of many cancers.

Transforming Growth Factor-beta (TGF-β), in particular the TGF-β2 isoform, has been identified as a key factor in the progression of malignant gliomas. TGF-β2, originally described as "glioblastoma-derived T-cell suppressor factor", is associated with the immuno-suppressed status of patients with glioblastoma, and is therefore responsible for loss of tumor immune surveillance. TGF beta has effects on tumor invasiveness, angiogenesis, tumor proliferation and immune suppression. Elevated TGF beta is associated with GBM, pancreatic colorectal, NSCLC, prostate, melanoma, HCC and hematological malignancies.

A growing body of evidence implicates the involvement of the enzyme indoleamine 2,3-dioxygenase (IDO-1 or IDO-2), which catabolize tryptophan, in mediating immunosuppression. In preclinical models of cancer, IDO inhibition has been demonstrated to improve chemotherapeutic efficacy. The mechanism of action is through inhibition of immune suppression most likely caused by secretion of the tryptophan metabolite kynurenine that causes apoptosis, cell cycle arrest and decreased activation of T cells and NK cells. Elevated IDO has been shown to occur in colorectal cancers, hepatocellular carcinoma, glioma and other tumors.

The programmed death receptor (PD1, also known as PDCD1) has been shown to be involved in regulating the balance between T cell activation and T cell tolerance in response to chronic antigens. During HIV1 infection, expression of PD1 has been found to be increased in CD4+ T cells. It is thought that PD1 up-regulation is somehow tied to T cell exhaustion (defined as a progressive loss of key effector functions) when T cell dysfunction is observed in the presence of chronic antigen exposure as is the case in HIV infection. PD1 up-regulation may also be associated with increased apoptosis in these same sets of cells during chronic viral infection (see, Petrovas et al., J Immunol. 183(2):1120-32, 2009). PD1 may also play a role in tumor-specific escape from immune surveillance. It has been demonstrated that PD1 is highly expressed in tumor-specific cytotoxic T lymphocytes (CTLs) in both chronic myelogenous leukemia (CML) and acute myelogenous leukemia (AML). PD1 is also up-regulated in melanoma infiltrating T lymphocytes (TILS) (see, Dotti, Blood 114 (8): 1457-58, 2009). Tumors have been found to express the PD1 ligand (PDL-1 and PDL-2) which, when combined with the up-regulation of PD1 in CTLs, may be a contributory factor in the loss in T cell functionality and the inability of CTLs to mediate an effective anti-tumor response. Researchers have shown that in mice chronically infected with lymphocytic choriomeningitis virus (LCMV), administration of anti-PD1 antibodies blocked PD1-PDL interaction and was able to restore some T cell functionality (proliferation and cytokine secretion), and lead to a decrease in viral load (Barber et al., Nature 439(9): 682-687, 2006). Dysregulation of PD1 may also play a role in autoimmune disease. SNPs of PD1 (in particular PD 1.3) have also been associated with increased risk for systemic lupus erythematosus (SLE). It has been shown that SLE patients have a higher frequency of the PD 1.3 PD1 allele, and that these patients show reduced PD1 expression on their activated CD4+ T cells (see, Bertsias et al., Arthritis Rheum. 60(1):207-18, 2009).

Further, blockade of the interaction between PD-1 and its ligand (PD-L1) potentiates immune responses in vitro and mediates preclinical antitumor activity. PD-L1 is the primary PD-1 ligand that is up-regulated in solid tumors, where it can inhibit cytokine production and the cytolytic activity of PD-1+, tumor-infiltrating CD4+ and CD8+ T cells. These properties make PD-L1 a potentially promising target for cancer immunotherapy. (Brahmer et al., N Engl J Med., 366:2455-2465, 2012). Anti-PD-1 antibody produced objective responses in approximately one in four to one in five patients with non-small-cell lung cancer, melanoma, or renal-cell cancer.

IDO-1 and PDL-1 are overexpressed in gliomas which hampers sustained adaptive anti-tumor response (antigen presentation of DCs, activation/proliferation of T-cells, cytolytic activity of CTLs) (Fogel-Petrovic et al., Int Immunopharmacol., 7:1924-3, 2007; Wainwright et al., Clin Can Res, doi:10.1158/1078-0432.CCR-14-0514, 2012).

Small interfering RNAs (siRNAs) down-regulate gene expression in human cells. This technology has the potential to treat a wide range of diseases including cancers but delivery of these molecules has been a significant barrier to implementation and at least several major pharmaceutical companies (Novartis, Pfizer, Abbott and Merck) have withdrawn or reduced effort on this approach because of this issue.

Suppression of tumor production of immune-modulatory molecules has remained difficult because of the need to continually suppress such production, when utilizing with modalities such as small molecules or cytokine/anticytokines. Local continuous tumor-centered production of anti-suppressive or pro-inflammatory agents is desirable because this avoids toxicities due to systemic administration of such immune enhancing drugs, and also provides for continuous production of the anti-immune suppressive agent.

The disclosure describes various embodiments that accomplish the foregoing by using a viral vector to deliver anti-immune suppressive agent or agents to tumors directly. In one embodiment the vector is a replicative vector and the anti-immune suppressive agent is selected from the group consisting of a prodrug activating protein, a cytokine, a single chain antibody, a binding molecule, a sh-/si-RNA (e.g., an RNAi molecule), or an agent that causes the production of any of the above including aptamers. In a further embodiment the replicative vector is a retroviral replicating vector (RRV). In another embodiment, the vector is a non-replicative (e.g., a non-replication competent viral vector).

Various vectors can be used in the methods and compositions of the disclosure. Polynucleotides encoding, for example, IFNγ, CD, PD1 and other immune-stimulating components provided herein can be incorporated into any one of a variety of expression vectors suitable for expressing a polypeptide or RNAi molecule. Suitable vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell.

The viral vector can be an adenoviral vector, a measles vector, a herpes vector, a retroviral vector (including a lentiviral vector), a rhabdoviral vector such as a Vesicular Stomatitis viral vector, a reovirus vector, a Seneca Valley Virus vector, a poxvirus vector (including animal pox or vaccinia derived vectors), a parvovirus vector (including an AAV vector), an alphavirus vector or other viral vector known to one skilled in the art (see also, e.g., *Concepts in Genetic Medicine*, ed. Boro Dropulic and Barrie Carter, Wiley, 2008, Hoboken, N.J.; *The Development of Human Gene Therapy*, ed. Theodore Friedmann, Cold Springs Harbor Laboratory Press, Cold springs Harbor, New York, 1999; *Gene and Cell Therapy*, ed. Nancy Smyth Templeton, Marcel Dekker Inc., New York, N.Y., 2000 and *Gene Therapy: Therapeutic Mechanism and Strategies*, ed. Nancy Smyth Templetone and Danilo D Lasic, Marcel Dekker, Inc., New York, N.Y., 2000; the disclosures of which are incorporated herein by reference).

Retroviral replicating vector (RRV) have advantages over lytic replicating vectors because they do not kill target cells immediately leading to local inflammation and an immune response focused on the virus (rather than the tumor). The use of RRV as a delivery vehicle in vivo allows viral and transgene spread through tumors without direct tumor lysis, thus amplifying the signal of the transgene in the tumor without active antiviral immunity. Others have tried to express siRNA from RRV (Schaser T. et al. Gene Ther 2011 doi:10.1038/gt.2011.48), but these vectors were of limited use because of titer and safety limitations and were only able to incorporate one gene expression cassette. The disclosure provides RRVs that express prodrug activating genes at titers useful for pharmaceutical use or that incorporate multiple cassettes. In addition, the vector backbone of the disclosure are currently in clinical trials with prodrug activating genes (Cloughsey et al., Neuro-Oncology 16:v110-v118, 2014. doi:10.1093/neuonc/nou258) demonstrating the safety and potency of these vectors in the clinic.

In one embodiment, the disclosure provides RRVs that inhibit expression or production of immune suppressive molecules in tumors. These molecules can be small molecules (e.g. adenosine, kynurenine), immune suppressive secreted proteins, cytokines or chemokines (e.g., TGF beta 1, 2 or 3, IL-1, IL-6, IL-10), immune suppressive ligands (e.g. PD-L1, PD-L2, B7-H3, B7-H4, HVEM, GAL9) or other immune suppressive molecules (Pardoll D., Nat Rev Cancer, 12:252-264, 2012). In a further embodiment, the production or expression of the immune suppressive molecule is inhibited by expression of a single chain antibody or an interfering RNA molecule (RNAi molecule). In a further embodiment, the inhibition of expression or production is achieved by expressing two genes or cassettes in an RRV. In a further embodiment one of the heterologous polynucleotides present in the vector expresses an RNAi molecule. In yet a further embodiment, the RNAi is expressed with a pol III promoter driving a microRNA (miRNA) cassette. In a further embodiment, a second cassette encodes one of: another RNAi molecule; a protein such as, but not limited to, a prodrug activating gene; a single chain antibody; a cytokine/chemokine; or other anticancer gene.

The disclosure provides retroviral replicating vectors the contain a heterologous polynucleotide encoding, for example, a cytosine deaminase or mutant thereof, an miRNA or siRNA, a cytokine, an antibody binding domain etc., that can be delivered to a cell or subject.

The disclosure provides modified retroviral replicating vectors. The modified retroviral replicating vectors can be derived from members of the retroviridae family. The Retroviridae family consists of three groups: the spumaviruses-(or foamy viruses) such as the human foamy virus (HFV); the lentiviruses, as well as visna virus of sheep; and the oncoviruses (although not all viruses within this group are oncogenic). The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2) and simian immunodeficiency virus (SIV). The oncoviruses have historically been further subdivided into groups A, B, C and D on the basis of particle morphology, as seen under the electron microscope during viral maturation. A-type particles represent the immature particles of the B- and D-type viruses seen in the cytoplasm of infected cells. These particles are not infectious. B-type particles bud as mature virion from the plasma membrane by the enveloping of intracytoplasmic A-type particles. At the membrane they possess a toroidal core of 75 nm, from which long glycoprotein spikes project. After budding, B-type particles contain an eccentrically located, electron-dense core. The prototype B-type virus is mouse mammary tumor virus (MMTV). No intracytoplasmic particles can be observed in cells infected by C-type viruses. Instead, mature particles bud directly from the cell surface via a crescent 'C'-shaped condensation which then closes on itself and is enclosed by the plasma membrane. Envelope glycoprotein spikes may be visible, along with a uniformly electron-dense core. Budding may occur from the surface plasma membrane or directly into intracellular vacuoles. The C-type viruses are the most commonly studied and include many of the avian and murine leukemia viruses (MLV). Bovine leukemia virus (BLV), and the human T-cell leukemia viruses types I and II (HTLV-I/II) are similarly classified as C-type particles because of the morphology of their budding from the cell surface. However, they also have a regular hexagonal morphology and more complex genome structures than the prototypic C-type viruses such as the murine leukemia viruses (MLV). D-type particles resemble B-type particles in that they show as ring-like structures in the infected cell cytoplasm, which bud from the cell surface, but the virion incorporate short surface glycoprotein spikes. The electron-dense cores are also eccentrically located within the particles. Mason Pfizer monkey virus (MPMV) is the prototype D-type virus.

Retroviruses have been classified in various ways but the nomenclature has been standardized in the last decade (see ICTVdB—The Universal Virus Database, v 4 on the World Wide Web (www) at ncbi.nlm.nih.gov/ICTVdb/ICTVdB/ and the text book "Retroviruses" Eds Coffin, Hughs and Varmus, Cold Spring Harbor Press 1997; the disclosures of which are incorporated herein by reference). In one embodiment, the replication competent retroviral vector can comprise an Orthoretrovirus or more typically a gamma retrovirus vector.

Retroviruses are defined by the way in which they replicate their genetic material. During replication the RNA is converted into DNA. Following infection of the cell a double-stranded molecule of DNA is generated from the two molecules of RNA which are carried in the viral particle by the molecular process known as reverse transcription. The DNA form becomes covalently integrated in the host cell genome as a provirus, from which viral RNAs are expressed with the aid of cellular and/or viral factors. The expressed viral RNAs are packaged into particles and released as infectious virion.

The retrovirus particle is composed of two identical RNA molecules. Each wild-type genome has a positive sense, single-stranded RNA molecule, which is capped at the 5' end and polyadenylated at the 3' tail. The diploid virus particle contains the two RNA strands complexed with gag proteins, viral enzymes (pol gene products) and host tRNA molecules within a 'core' structure of gag proteins. Surrounding and protecting this capsid is a lipid bilayer, derived from host cell membranes and containing viral envelope (env) proteins. The env proteins bind to a cellular receptor for the virus and the particle typically enters the host cell via receptor-mediated endocytosis and/or membrane fusion.

After the outer envelope is shed, the viral RNA is copied into DNA by reverse transcription. This is catalyzed by the reverse transcriptase enzyme encoded by the pol region and uses the host cell tRNA packaged into the virion as a primer for DNA synthesis. In this way the RNA genome is converted into the more complex DNA genome.

The double-stranded linear DNA produced by reverse transcription may, or may not, have to be circularized in the nucleus. The provirus now has two identical repeats at either end, known as the long terminal repeats (LTR). The termini of the two LTR sequences produces the site recognized by a pol product—the integrase protein—which catalyzes integration, such that the provirus is always joined to host DNA two base pairs (bp) from the ends of the LTRs. A duplication of cellular sequences is seen at the ends of both LTRs, reminiscent of the integration pattern of transposable genetic elements. Retroviruses can integrate their DNAs at many sites in host DNA, but different retroviruses have different integration site preferences. HIV-1 and simian immunodeficiency virus DNAs preferentially integrate into expressed genes, murine leukemia virus (MLV) DNA preferentially integrates near transcriptional start sites (TSSs), and avian sarcoma leukosis virus (ASLV) and human T cell leukemia virus (HTLV) DNAs integrate nearly randomly, showing a slight preference for genes (Derse D. et al. (2007) Human T-cell leukemia virus type 1 integration target sites in the human genome: comparison with those of other retroviruses. J Virol 81:6731-6741; Lewinski M K, et al. (2006) Retroviral DNA integration: viral and cellular determinants of target-site selection. PLoS Pathog 2:e601).

Transcription, RNA splicing and translation of the integrated viral DNA is mediated by host cell proteins. Variously spliced transcripts are generated. In the case of the human retroviruses HIV-1/2 and HTLV-I/II viral proteins are also used to regulate gene expression. The interplay between cellular and viral factors is a factor in the control of virus latency and the temporal sequence in which viral genes are expressed.

Retroviruses can be transmitted horizontally and vertically. Efficient infectious transmission of retroviruses requires the expression on the target cell of receptors which specifically recognize the viral envelope proteins, although viruses may use receptor-independent, nonspecific routes of entry at low efficiency. Normally a viral infection leads to a single or few copies of viral genome per cell because of receptor masking or down-regulation that in turn leads to resistance to superinfection (Ch3 p104 in "Retroviruses," J M Coffin, S H Hughes, & H E Varmus 1997 Cold Spring Harbor Laboratory Press, Cold Spring Harbor N.Y.; Fan et al. J. Virol 28:802, 1978). By manipulating the situation in tissue culture it is possible to get some level of multiple infection but this is less than 5 copies/diploid genome. In addition, the target cell type must be able to support all stages of the replication cycle after virus has bound and penetrated. Vertical transmission occurs when the viral genome becomes integrated in the germ line of the host. The provirus will then be passed from generation to generation as though it were a cellular gene. Hence endogenous proviruses become established which frequently lie latent, but which can become activated when the host is exposed to appropriate agents.

A suitable vector of the disclosure has a general structure from 5' to 3' comprising a long terminal repeat (LTR)-gag sequence-pol sequence-env sequence-(at least one expression cassette)-LTR. The expression cassette(s) is just downstream (e.g., 1 to 50 bp, 2-40 bp, 3-20 bp, 5-15 bp or any value there between) from the end of the env gene, but upstream from the 3' LTR. Exemplary structures of a vector of the disclosure are set forth in FIGS. 1A-C.

In one embodiment, the retroviral polynucleotide sequence is derived from murine leukemia virus (MLV), Moloney murine leukemia virus (MoMLV), Feline leukemia virus (FeLV) or Gibbon ape leukemia virus (GALV). In another embodiment, the MLV is an amphotropic MLV. In yet another embodiment, the retrovirus is an oncoretrovirus or gamma retrovirus.

The disclosure thus provides a recombinant replication competent retrovirus (RCR) comprising: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; at least one cassette comprising a heterologous nucleic acid sequence, wherein the cassette is positioned 5' to the 3' LTR and 3' to the env nucleic acid domain encoding the retroviral envelope; and cis-acting sequences necessary for reverse transcription, packaging and integration in a target cell. In one embodiment, the retroviral polynucleotide sequence is derived from murine leukemia virus (MLV), Moloney murine leukemia virus (MoMLV), Feline leukemia virus (FeLV) or Gibbon ape leukemia virus (GALV). In another embodiment, the MLV is an amphotropic MLV. In yet another embodiment, the retrovirus is an oncoretrovirus or gamma retrovirus.

In one embodiment, the promoter comprises a CMV promoter having a sequence as set forth in SEQ ID NO:1-15 or 16 from nucleotide 1 to about nucleotide 582 and may include modification to one or more nucleic acid bases and which is capable of directing and initiating transcription. In yet a further embodiment, the promoter comprises a sequence as set forth in SEQ ID NO: 1-15 or 16 from nucleotide 1 to about nucleotide 582. In a further embodiment, the promoter comprises a CMV-R-U5 domain polynucleotide. In one embodiment, the CMV-R-U5 domain comprises the immediately early promoter from human cytomegalovirus linked to an MLV R-U5 region. In yet another embodiment, the CMV-R-U5 domain polynucleotide comprises a sequence as set forth in SEQ ID NO: 1-15 or 16 from about nucleotide 1 to about nucleotide 1202 or sequences that are at least 95% identical to a sequence as set forth in SEQ ID NO: 1-15 or 16 from nucleotide 1 to about nucleotide 1202, wherein the polynucleotide promotes transcription of a nucleic acid molecule operably linked thereto. In an alternative embodiment, the promoter can be a tissue specific promoters such as those described below. In a further embodiment, the gag and pol of the polynucleotide are derived from an oncoretrovirus or gamma retrovirus. The gag nucleic acid domain can comprise a sequence from about nucleotide number 1203 to about nucleotide 2819 of SEQ ID NO: 1-15 or 16 or a sequence having at least 95%, 98%, 99% or 99.8% identity thereto. The pol domain can comprise a sequence from about nucleotide number 2820 to about nucleotide 6358 of SEQ ID NO: 1-15 or 16 or a sequence having at least 95%, 98%, 99% or 99.9% identity thereto. In one embodiment, the env domain encodes an amphotropic env protein. The env domain can comprise a sequence from about nucleotide number 6359 to about nucleotide 8323 of SEQ ID NO: 1-15 or 16 or a sequence having at least 95%, 98%, 99% or 99.8% identity thereto. At least one cassette is 3' to the env gene sequence.

In one embodiment, the at least one cassette comprises a polIII promoter operably linked to an RNAi sequence to be expressed (see, e.g., FIG. 1A). In one embodiment, the polIII promoter comprises an H1 promoter (e.g., SEQ ID NO:7 or 12 from about 8330 to 8553, and an H1 termination sequence from about 8885 to 8889 and 8925 to 8930). In another embodiment, the polIII promoter comprises a U6 promoter (e.g., SEQ ID NO:8 or 13 from about 8330-8595 and a U6 termination sequence from about 8922-8926 and 8962 to 8967). In any of the foregoing embodiments, the polIII promoter (e.g., H1 or U6) are operably linked to an RNAi encoding sequence.

In some embodiments, the at least one cassette comprises a core- or mini-promoter such as the RSV promoter. For example, the RSV promoter can comprise a sequence from about 8330 to about 8591 of SEQ ID NO:9, 10, 14, 15, or 16. In any of the foregoing embodiments, the RSV promoter is operably linked to an RNAi encoding sequence. In another embodiment, the RSV promoter is operably linked to a polynucleotide encoding a polypeptide having cytosine deaminase activity (e.g., "yCD2" having a sequence from about 8592 to about 9068 or 9071 of SEQ ID NO:11 and 10, respectively). In still a further embodiment, the RSV promoter can be operably linked to a polynucleotide encoding a polypeptide having cytosine deaminase followed by a sequence encoding an RNAi molecule.

In some embodiments, the at least one cassette comprises two cassettes wherein a first cassette comprises an H1 or U6 promoter linked to an RNAi encoding sequence and the second cassette comprises an RSV promoter operably linked to a polynucleotide encoding a polypeptide (e.g., a cytosine deaminase or antibody domain).

Figure 1B:
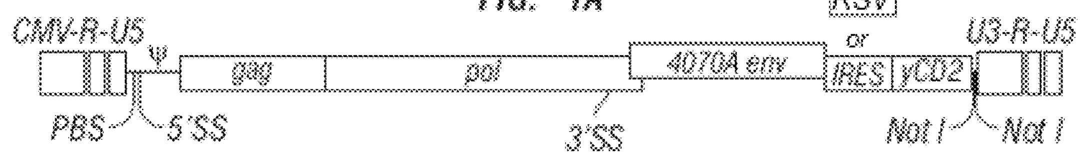
Figure 1C:
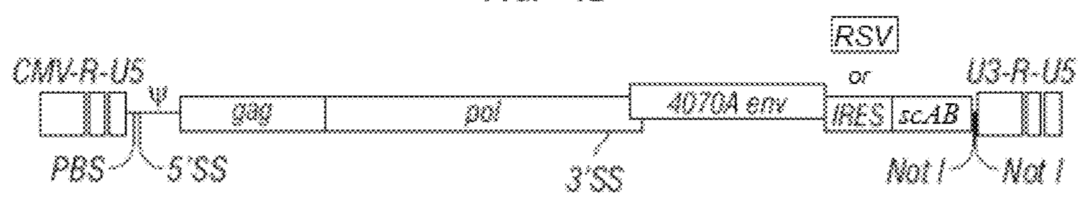

In some embodiments, the cassette comprises a promoter linked to an RNAi encoding sequence and further comprises an IRES operably linked a prodrug activating gene (e.g., cytosine deaminase) (see, e.g., FIG. 1B). In another embodiment, the cassette comprises a minipromoter or IRES operably linked to an antibody (e.g., a single chain antibody sequence). In still a further embodiment, the cassette comprising the antibody sequence can further comprise a polIII promoter operably linked to an RNAi sequence (see, e.g., FIG. 1C).

An internal ribosome entry sites ("IRES") refers to a segment of nucleic acid that promotes the entry or retention of a ribosome during translation of a coding sequence usually 3' to the IRES. In some embodiments the IRES may comprise a splice acceptor/donor site, however, preferred IRESs lack a splice acceptor/donor site. Normally, the entry of ribosomes into messenger RNA takes place via the cap located at the 5' end of all eukaryotic mRNAs. However, there are exceptions to this universal rule. The absence of a cap in some viral mRNAs suggests the existence of alternative structures permitting the entry of ribosomes at an internal site of these RNAs. To date, a number of these structures, designated IRES on account of their function, have been identified in the 5' noncoding region of uncapped viral mRNAs, such as that, in particular, of picornaviruses such as the poliomyelitis virus (Pelletier et al., 1988, Mol. Cell. Biol., 8, 1103-1112) and the EMCV virus (encephalomyocarditis virus (Jang et al., J. Virol., 1988, 62, 2636-2643). The disclosure provides the use of an IRES in the context of a replication-competent retroviral vector.

The IRES domain of the vector can be any IRES, however, in one embodiment the IRES is derived from an encephalomyocarditis virus. In a further embodiment, the IRES comprises a sequence from about nucleotide number 8327 to about nucleotide 8876 of SEQ ID NO: 1 or a sequence having at least 95%, 98%, or 99% identity thereto.

In another embodiment, the RNA polymerase III promoters can be a U6 or an H1 promoter. In one embodiment, the polIII promoter comprises an H1 promoter (e.g., SEQ ID NO:7 or 12 from about 8330 to 8553, and an H1 termination sequence from about 8885 to 8889 and 8925 to 8930). In another embodiment, the polIII promoter comprises a U6 promoter (e.g., SEQ ID NO:8 or 13 from about 8330-8595 and a U6 termination sequence from about 8922-8926 and 8962 to 8967).

The following table sets forth exemplary domains for a number of vector described herein.

TABLE 1

| Domain | Sequence |
|---|---|
| SEQ ID NO: 7 | |
| Gag | 1203-2819 |
| Pol | 2820-6358 |
| 4070A env | 6359-8323 |
| Mlu1 restriction site | 8324-8329 |
| Human H1 promoter | 8330-8553 |
| IDO1miR30shRNA2 | 8559-8973 |
| PolIII termination sequence | 8885-8889, 8925-8930 |
| Not I restriction site | 8950-8957 |
| SEQ ID NO: 8 | |
| Gag | 1203-2819 |
| Pol | 2820-6358 |
| 4070A env | 6359-8323 |
| Mlu1 restriction site | 8324-8929 |
| Human U6 promoter | 8330-8595 |
| IDO1miR30shRNA2 | 8645-8974 |
| PolIII termination sequence | 8922-8926, 8962-8967 |
| Not I restriction site | 8987-8994 |
| SEQ ID NO: 9 | |
| Gag | 1203-2819 |
| Pol | 2820-6358 |
| 4070A env | 6359-8323 |
| Mlu1 restriction site | 8324-8329 |
| RSV promoter | 8330-8591 |
| IDO1miR30shRNA2 | 8598-8976 |
| Not I restriction site | 8989-8996 |
| SEQ ID NO: 10 | |
| Gag | 1203-2819 |
| Pol | 2820-6358 |
| 4070A env | 6359-8323 |
| Mlu1 restriction site | 8324-8329 |
| RSV promoter | 8330-8591 |
| yCD2 | 8592-9071 |
| IDO1miR30shRNA2 | 9078-9456 |
| Not I restriction site | 9469-9476 |

TABLE 1-continued

| Domain | Sequence |
|---|---|
| SEQ ID NO: 11 | |
| Gag | 1203-2819 |
| Pol | 2820-6358 |
| 4070A env | 6359-8323 |
| Mlu1 restriction site | 8324-8329 |
| RSV promoter | 8330-8591 |
| yCD2 | 8592-9068 |
| Human U6 promoter | 9072-9337 |
| IDO1miR30shRNA2 | 9343-9721 |
| Pol III termination seq | 9669-9673, 9709-9714 |
| Not I restriction site | 9734-9741 |
| SEQ ID NO: 12 | |
| Gag | 1203-2819 |
| Pol | 2820-6358 |
| 4070A env | 6359-8323 |
| Mlu1 restriction site | 8324-8329 |
| Human H1 promoter | 8330-8553 |
| PDL1miR30shRNA4 | 8559-8937 |
| Pol III termination seq | 8885-8889, 8925-8930 |
| Not I restriction site | 8950-8957 |
| SEQ ID NO: 13 | |
| Gag | 1203-2819 |
| Pol | 2820-6358 |
| 4070A env | 6359-8323 |
| Mlu1 restriction site | 8324-8329 |
| Human U6 promoter | 8330-8595 |
| PDL1miR30shRNA4 | 8645-8974 |
| Pol III termination seq | 8922-8926, 8962-8967 |
| Not I restriction site | 8987-8994 |
| SEQ ID NO: 14 | |
| Gag | 1203-2819 |
| Pol | 2820-6358 |
| 4070A env | 6359-8323 |
| Mlu1 restriction site | 8324-8329 |
| RSV promoter | 8330-8591 |
| PDL1miR30shRNA4 | 8598-8976 |
| Not I restriction site | 8989-8996 |
| SEQ ID NO: 15 | |
| Gag | 1203-2819 |
| Pol | 2820-6358 |
| 4070A env | 6359-8323 |
| Mlu1 restriction site | 8324-8329 |
| RSV promoter | 8330-8591 |
| yCD2 | 8592-9071 |
| PDL1miR30shRNA4 | 9078-9456 |
| Not I restriction site | 9469-9476 |
| SEQ ID NO: 16 | |
| Gag | 1203-2819 |
| Pol | 2820-6358 |
| 4070A env | 6359-8323 |
| Mlu1 restriction site | 8324-8329 |
| RSV promoter | 8330-8591 |
| yCD2 | 8592-9068 |
| Human U6 promoter | 9072-9337 |
| PDL1miR30shRNA4 | 9343-9721 |
| Pol III termination seq | 9669-9673, 9709-9714 |
| Not I restriction site | 9734-9741 |

As will be recognized by one of skill in the art, the sequence 3' to the cassette comprise untranslated and 3' LTR sequences for each of the vectors described herein.

As used herein, the term "RNA interference" (RNAi) refers to the process of sequence-specific post-transcriptional gene silencing mediated by short interfering nucleic acids (siRNAs or microRNAs (miRNA)). RNAi generally refers to the process by which siRNA, miRNA and the like are expressed from an RNA polymerase transcript and inhibit expression of a target gene. An "inhibitory nucleic acid sequence" is an oligonucleotide or polynucleotide that when expressed causes post-transcriptional gene silencing. An inhibitory nucleic acid sequence thus comprises molecules that when processed include siRNA, miRNA and the like. The term "agent capable of mediating RNA interference" refers to siRNAs as well as DNA and RNA vectors that encode siRNAs when transcribed within a cell. The term siRNA or miRNA is meant to encompass any nucleic acid molecule that is capable of mediating sequence specific RNA interference, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and other non-coding RNAs.

Suitable range for designing stem lengths of a hairpin duplex, includes stem lengths of 20-30 nucleotides, 30-50 nucleotides, 50-100 nucleotides, 100-150 nucleotides, 150-200 nucleotides, 200-300 nucleotides, 300-400 nucleotides, 400-500 nucleotides, 500-600 nucleotides, and 600-700 nucleotides. Suitable range for designing loop lengths of a hairpin duplex, includes loop lengths of 4-25 nucleotides, 25-50 nucleotides, or longer if the stem length of the hair duplex is substantial. In certain context, hairpin structures with duplexed regions that are longer than 21 nucleotides may promote effective siRNA-directed silencing, regardless of the loop sequence and length.

MicroRNAs (miRNA) are small, non-coding RNAs. They are located within introns of coding or non-coding gene, exons of non-coding genes or in inter-genic regions. miRNA genes are transcribed by RNA polymerase II that generate precursor polynucleotides called primary precursor miRNA (pri-miRNA). The pri-miRNA in the nucleus is processed by the ribonuclease Drosha to produce the miRNA precursor (pre-miRNA) that forms a short hairpin structure. Subsequently, pre-miRNA is transported to the cytoplasm via Exportin 5 and further processed by another ribonuclease called Dicer to generate an active, mature miRNA.

A mature miRNA is approximately 21 nucleotides in length. It exerts in function by binding to the 3' untranslated region of mRNA of targeted genes and suppressing protein expression either by repression of protein translation or degradation of mRNA. miRNA are involved in biological processes including development, cell proliferation, differentiation and cancer progression. Studies of miRNA profiling indicate that some miRNA expressions are tissue specific or enriched in certain tissues. For example, miR-142-3p, miR-181 and miR-223 expressions have demonstrated to be enriched in hematopoietic tissues in human and mouse (Baskerville et al., 2005 *RNA* 11, 241-247; Chen et al., 2004 *Science* 303, 83-86).

Some miRNAs have been observed to be up-regulated (oncogenic miRNA) or down-regulated (repressor) in several tumors (Spizzo et al., 2009 *Cell* 137, 586e1). For example, miR-21 is overexpressed in glioblastoma, breast, lung, prostate, colon, stomach, esophageal, and cervical cancer, uterine leiomyosarcoma, DLBCL, head and neck cancer. In contrast, members of let-7 have reported to be down-regulated in glioblastoma, lung, breast, gastric, ovary, prostate and colon cancers. Re-establishment of homeostasis of miRNA expression in cancer is an imperative mechanism to inhibit or reverse cancer progression.

As a consequence of the vital functions modulated by miRNAs in cancers, focus in developing potential therapeutic approaches has been directed toward antisense-mediated inhibition (antigomers) of oncogenic miRNAs. However, miRNA replacement might represent an equally efficacious strategy. In this approach, the most therapeutically useful miRNAs are the ones expressed at low levels in tumors but at high level, and therefore tolerated, in normal tissues.

miRNAs that are down-regulated in cancers could be useful as anticancer agents. Examples include mir-128-1, let-7, miR-26, miR-124, and miR-137 (Esquela-Kerscher et al., 2008 Cell Cycle 7, 759-764; Kumar et al., 2008 *Proc Natl Acad Sci USA* 105, 3903-3908; Kota et al., 2009 Cell 137, 1005-1017; Silber et al., 2008 BMC Medicine 6:14 1-17). miR-128 expression has reported to be enriched in the central nervous system and has been observed to be down-regulated in glioblastomas (Sempere et al., 2004 *Genome Biology* 5:R13.5-11; Godlewski et al., 2008 *Cancer Res* 68: (22) 9125-9130). miR-128 is encoded by two distinct genes, miR-128-1 and miR-128-2. Both are processed into identical mature sequence. Bmi-1 and E2F3a have been reported to be the direct targets of miR-128 (Godlewski et al., 2008 *Cancer Res* 68: (22) 9125-9130; Zhang et al., 2009 *J. Mol Med* 87:43-51). In addition, Bmi-1 expression has been observed to be up-regulated in a variety of human cancers, including gliomas, mantle cell lymphomas, and non-small cell lung cancer B-cell non-Hodgkin's lymphoma, and breast, colorectal and prostate cancer. Furthermore, Bmi-1 has been demonstrated to be required for the self-renewal of stem cells from diverse tissues, including neuronal stem cells as well as "stem-like" cell population in gliomas.

Exemplary RNAi sequences are set forth in Table 1 (above) and are defined by their sequences identified in the table. Such RNAi include, but are not limited to: IDO1miR30shRNA2 and PDL1miR30shRNA4 sequences set forth herein.

The replicating retroviral vectors of the disclosure can be used to treat disease by expressing engineered siRNA or miRNA (Dennis, Nature, 418: 122 2002) that switches off or lowers expression of key genes that govern the proliferation or survival of diseased cells including tumor cells. Such targets include genes like Rad 51 a central enzyme in DNA repair, and without which cell growth is drastically restricted. Other targets include many of the signaling pathway molecules that control cell growth (Marquez & McCaffrey Hum Gene Ther. 19:27 2008). The siRNA or miRNA may be combined with expression of a cytotoxic gene from the same or different retroviral vector of the disclosure. An example of a suitable cytotoxic gene comprise a cytosine deaminase or modified cytosine deaminase of the disclosure. Examples of siRNA or miRNA that can be expressed from the same vector or a different vector with cytosine deaminase are siRNA or miRNA's that target thymidilate synthase, dihydropyrimidine dehydrogenase or other nucleic acid anabolic or synthetic enzymes, that can enhance or complement the action of 5-FU produced locally in a tumor or tissue from 5-FC activation by cytosine deaminase.

In use, the retroviral vector(s) will replicate through the tumor or other target tissue and before growth inhibition occurs the virus first integrates into the host genome and continues to make virus after growth of that cell is inhibited. Methods for selecting functional miRNA or siRNA sequences are known in the art. Key feature in general in designing effective siRNA or miRNA sequences is usually avoiding "off-target" effects. However for the use of replicating vectors that are highly specific to tumor cells such as those of the disclosure, these side effects are not very important, as the cells are expected to eventually die. A retroviral vector of this disclosure can be made using cells from other species for which the corresponding protein is not significantly targeted. Such cells include dog cell lines or chicken cell line. Alternatively the virus is made by transient transfection on human 293 derived cells or other cell line that allows efficient transient transfection. For this use the virus does not need to utilize an IRES, and the siRNA or miRNA sequence can simply be inserted at a convenient site on the viral genome. This site includes the region downstream of the envelope and upstream of the 3'LTR of the replicating retrovirus.

As described above, polIII transcription units can be inserted in the viral genome with the appropriate siRNA or miRNA's, typically downstream of the 3' envelope gene. Several different siRNA or miRNA sequences can be inserted to ensure efficient down regulation of the target gene or down regulation of more than one gene. Suitable sequences and targets can be obtained from sources known to those skilled in the art. For example:

The MIT/ICBP siRNA Database http:(//)[web.]_[mit.edu/sirna/ - "The MIT [Massachusetts Institute of Technology]/ICBP [Integrative Cancer Biology Program] siRNA Database is a university-wide effort to catalog these experimentally validated reagents and make that information available to other researchers, both within and outside the MIT community. (Massachusetts Institute of Technology).

RNAi Central - http:(//)[_]katandin.cshl.org:9331/RNAi_web/ scripts/main2.pl RNAi resources, including siRNA and shRNA design tools. (Hannon Lab, Cold Spring Harbor Laboratory)

The RNAi Web - http:(//)[www.]_[rnaiweb.com/ General resource.

siDIRECT - http:(//)]_[genomics.jp/sidirect/ Online target-specific siRNA design program for mammalian RNA interference. (University of Tokyo, Japan).

siRNA Database - A comprehensive siRNA database that contains siRNA targets against all known mRNA sequences throughout a variety of organisms. (Part of the Protein Lounge systems biology Web site)

siRNA Database and Resources for RNA Interference Studies http:(//)[www.][mainterference.org/ siRNA Selector - http:(//)]_[bioinfo.wistar.upenn.edu/siRNA /siRNA.htm. A set of rules was used for evaluating siRNA functionality based on thermodynamics parameters (Khvorova et al., 2003, Schwarz et al., 2003) and sequence-related determinants developed by Dharmacon (Reynolds et al., 2004). Specificity is determined using BLAST against UniGene databases. (Wistar Institute)

siRNA Target Finder http:(//)]_[www(.)ambion.com/techlib/misc/ siRNA_finder.html (Ambion).

In another embodiment, a vector of the disclosure comprise a retroviral non-replicating vector (RNV, aka a replication defective retrovirus). Retroviral non-replicating vectors (RNV) are engineered to lack key genes and elements for transmission. For example, an RNV lacks one or more of the pol or env genes or the necessary cis acting (W) sequences for transcription and packaging in a host cell.

The RNV of the disclosure includes at least one transcriptional promoter/enhancer or locus defining element(s), or other elements which control gene expression by other means such as alternate splicing, nuclear RNA export, post-translational modification of messenger, or post-transcriptional modification of protein. Such vector constructs include a packaging signal, long terminal repeats (LTRs) or portion thereof, and positive and negative strand primer binding sites appropriate to the retrovirus used (if these are not already present in the retroviral vector). Optionally, the recombinant retroviral vector may also include a signal which directs polyadenylation, a selectable marker such as a non-antibiotic selectable marker (e.g., cytosine deaminase, thymidine kinase and the like), as well as one or more restriction sites and a translation termination sequence. By way of example, such vectors typically include a 5' LTR, a tRNA binding site, a packaging signal, an origin of second strand DNA synthesis, and a 3' LTR or a portion thereof. Various modifications or additions to these specifications of the RNV structure may also be uses that may increase safety or performance (see e.g. Corrigan-Curay et al., Mol Ther op.cit; Stein et al. Hum Gene Ther-Clin Develop 24:86-98 2013, DOI: 10.1089/humc.2013.019)

As noted above, the disclosure provides recombinant retroviruses which are constructed to carry at least one cassette or express one or more nucleic acid molecule of interest. The RNVs of the disclosure may be readily constructed from a wide variety of retroviruses, including for example, B, C, and D type retroviruses as well as spumaviruses and lentiviruses. Typically, retroviruses for the preparation or construction of RNV delivery vehicles of the disclosure include retroviruses selected from the group consisting of Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. In a specific embodiment, a Murine Leukemia Viruses such as MLV 4070A and 1504A (Hartley and Rowe, 1976, J. Virol. 19:19-25), Abelson (ATCC No. VR-999), Friend ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190) can be used. Such retroviruses may be readily obtained from depositories or collections such as the American Type Culture Collection ("ATCC"; Manasassas, Va.), or isolated from known sources using commonly available techniques.

Any of the above retroviruses may be readily utilized in order to assemble or construct a RNV gene delivery vehicles given the disclosure provided herein, and standard recombinant techniques (e.g., Sambrook et al., Molecular Cloning: A Laboratory Manual, 2d ed., Cold Spring Harbor Laboratory Press, 1989; Kunkle, 1985, PNAS 82:488). In addition, within certain embodiments of the disclosure, portions of the retroviral gene delivery vehicles may be derived from different retroviruses. For example, within one embodiment of the disclosure, retroviral vector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

In another embodiment, an RNV may be made by introducing a vector construct as discussed above, into a cell (termed a, "packaging cell") which contains those elements necessary for production of infectious recombinant retrovirus which are lacking in the vector construct. A wide variety of retroviral vector constructs may be utilized within the disclosure in order to prepare an RNV. For example, within one embodiment of the disclosure retroviral vector constructs are provided comprising a 5' LTR, a tRNA binding site, a packaging signal, one or more cassettes (e.g., heterologous sequences), an origin of second strand DNA synthesis and a 3' LTR, wherein the vector construct lacks all or a portion of the gag/pol or env coding sequences. Briefly, Long Terminal Repeats ("LTRs") are subdivided into three elements, designated U5, R and U3. These elements contain a variety of signals which are responsible for the biological activity of a retrovirus, including for example, promoter and enhancer elements which are located within U3. LTRs may be readily identified in the provirus due to their precise duplication at either end of the genome. As utilized herein, a 5' LTR should be understood to include a 5' promoter element, and sufficient LTR sequence to allow reverse transcription and integration of the DNA form of the vector. The 3' LTR should be understood to include a polyadenylation signal, and sufficient LTR sequence to allow reverse transcription and integration of the DNA form of the vector.

The tRNA binding site and origin of second strand DNA synthesis are also important for a retrovirus to be biologically active, and may be readily identified by one of skill in the art. For example, retroviral tRNA binds to a tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5' LTR. Similarly, the origin of second strand DNA synthesis is, as its name implies, important for the second strand DNA synthesis of a retrovirus. This region, which is also referred to as the poly-purine tract, is located just upstream of the 3' LTR.

In addition to a 5' and 3' LTR, tRNA binding site, and origin of second strand DNA synthesis, certain RNV constructs which are provided herein also comprise a packaging signal, as well as one or more nucleic acid molecules (e.g., heterologous sequences), each of which is discussed in more detail below.

In one embodiment, the retroviral vector constructs are provided which lack both gag/pol and env coding sequences. As utilized herein, the phrase "lacks gag/pol or env coding sequences" should be understood to mean that the retroviral vector does not contain at least 20, at least 15, at least 10, or at least 8 consecutive nucleotides which are found in gag/pol or env genes, and in particular, within gag/pol or env expression cassettes that are used to construct packaging cell lines for the retroviral vector construct. Alternatively, the retroviral vector constructs are provided that lack pol or env sequences but carry the gag sequences that correspond to the extended packaging sequence but with translation disabling mutations in those gag sequences.

The heterologous nucleic acid sequence of the disclosure are typically present in a cassette under control of either the viral LTR promoter-enhancer signals or an internal promoter, and retained signals within the retroviral LTR can still bring about efficient integration of the vector into the host cell genome. Accordingly, the recombinant retroviral vectors of the disclosure, the desired sequences, genes and/or gene fragments can be inserted at several sites and under different regulatory sequences. For example, a site for insertion can be the viral enhancer/promoter proximal site (i.e., 5' LTR-driven gene locus). Alternatively, the desired sequences can be inserted into a distal site (e.g., downstream of the IRES sequence 3' to the env gene, the RSV sequence 3' to the env gene, and/or the H1 or U6 promoter sequence 3' to the env gene) or where two or more heterologous sequences are present one heterologous sequence may be under the control of a first regulatory region and a second heterologous sequence under the control of a second regulatory region. Other distal sites include viral promoter sequences, where the expression of the desired sequence or sequences is through splicing of the promoter proximal cistron, an internal heterologous promoter as SV40 or CMV, or an internal ribosome entry site (IRES) can be used.

In addition, this list of promoters should not be construed to be exhaustive or limiting, those of skill in the art will know of other promoters that may be used in conjunction with the promoters and methods disclosed herein.

TABLE 2

| TISSUE SPECIFIC PROMOTERS | |
|---|---|
| Tissue | Promoter |
| Pancreas | Insulin Elastin Amylase pdr-1 pdx-1 glucokinase |
| Liver | Albumin PEPCK HBV enhancer α fetoprotein apolipoprotein C α-1 antitrypsin vitellogenin, NF-AB Transthyretin |
| Skeletal muscle | Myosin H chain Muscle creatine kinase Dystrophin Calpain p94 Skeletal alpha-actin fast troponin 1 |
| Skin | Keratin K6 Keratin K1 |
| Lung | CFTR Human cytokeratin 18 (K18) Pulmonary surfactant proteins A, B and C CC-10 P1 |
| Smooth muscle | sm22 α SM-alpha-actin |
| Endothelium | Endothelin-1 E-selectin von Willebrand factor TIE, KDR/flk-1 Melanocytes Tyrosinase |
| Adipose tissue | Lipoprotein lipase (Zechner et al., 1988) Adipsin (Spiegelman et al., 1989) acetyl-CoA carboxylase (Pape and Kim, 1989) glycerophosphate dehydrogenase (Dani et al., 1989) adipocyte P2 (Hunt et al., 1986) |
| Breast | Whey Acidic Protein (WAP) (Andres et al. PNAS 84: 1299-1303 1987 |
| Blood | β-globin |

"Tissue-specific regulatory elements" are regulatory elements (e.g., promoters) that are capable of driving transcription of a gene in one tissue while remaining largely "silent" in other tissue types. It will be understood, however, that tissue-specific promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the disclosure typically has a selectivity ratio of greater than about 5. Preferably, the selectivity ratio is greater than about 15.

It will be further understood that certain promoters, while not restricted in activity to a single tissue type, may nevertheless show selectivity in that they may be active in one group of tissues, and less active or silent in another group. Such promoters are also termed "tissue specific", and are contemplated for use with the disclosure. Accordingly, the tissue-specific regulatory elements used in the disclosure, have applicability to regulation of the heterologous proteins such as the polypeptides having cytosine deaminase activity of the disclosure as well as a applicability as a targeting polynucleotide sequence in retroviral vectors.

As noted above, the disclosure is directed generally towards methods of inhibiting the growth of a selected tumor utilizing vector constructs which direct the expression of an anti-tumor agent. In particular, the disclosure provides methods for inhibiting the growth of a selected tumor in a warm-blooded animal, comprising the step of directly administering to the tumor a vector construct of the disclosure (e.g., an RRV or RNV), which directs the expression of at least one anti-tumor agent, such that the growth of the tumor is inhibited.

Within the context of the disclosure, "inhibiting the growth of a selected tumor" refers to either (1) the direct inhibition of tumor cell division, or (2) immune cell mediated tumor cell lysis, or both, which leads to a suppression in the net expansion of tumor cells. Inhibition of tumor growth by either of these two mechanisms may be readily determined by one of ordinary skill in the art based upon a number of well-known methods. For example, tumor inhibition may be determined by measuring the actual tumor size over a period of time. Alternatively, tumor inhibition may be determined by estimating the size of a tumor (over a period of time) utilizing methods well known to those of skill in the art. More specifically, a variety of radiologic imaging methods (e.g., single photon and positron emission computerized tomography; see generally, "Nuclear Medicine in Clinical Oncology," Winkler, C. (ed.) Springer-Verlag, New York, 1986), may be utilized to estimate tumor size. Such methods may also utilize a variety of imaging agents, including for example, conventional imaging agents (e.g., Gallium-67 citrate), as well as specialized reagents for metabolite imaging, receptor imaging, or immunologic imaging (e.g., radiolabeled monoclonal antibody specific tumor markers). In addition, non-radioactive methods such as ultrasound (see, "Ultrasonic Differential Diagnosis of Tumors", Kossoff and Fukuda, (eds.), Igaku-Shoin, New York, 1984), may also be utilized to estimate the size of a tumor.

In addition to the in vivo methods for determining tumor inhibition discussed above, a variety of in vitro methods may be utilized in order to predict in vivo tumor inhibition. Representative examples include lymphocyte mediated anti-tumor cytolytic activity determined for example, by a $^{51}$Cr release assay, tumor dependent lymphocyte proliferation (Ioannides et al., J. Immunol. 146(5):1700-1707, 1991), in vitro generation of tumor specific antibodies (Herlyn et al., J. Immunol. Meth. 73:157-167, 1984), cell (e.g., CTL, helper T cell) or humoral (e.g., antibody) mediated inhibition of cell growth in vitro (Gazit et al., Cancer Immunol. Immunother 35:135-144, 1992), and, for any of these assays, determination of cell precursor frequency (Vose, Int. J. Cancer 30:135-142 (1982), see also F. Saade et al. Exp Rev Vaccines 11:1459-1470 2012 for a review of such methods Alternatively, for other forms of cancer, inhibition of tumor growth may be determined based upon a change in the presence of a tumor marker. Examples include prostate specific antigen ("PSA") for the detection of prostate cancer (see. U.S. Pat. No. Re. 33,405), and Carcino-Embryonic Antigen ("CEA") for the detection of colorectal and certain breast cancers. For yet other types of cancers such as leukemia, inhibition of tumor growth may be determined based upon the decreased numbers of leukemic cells in a representative blood cell count.

A variety of tumors may be selected for treatment in accordance with the methods described herein. Solid tumors, leukemias and lymphomas may be treated. Representative examples of suitable tumors include melanomas, colorectal carcinomas, lung carcinomas (including large cell, small cell, squamous and adeno-carcinomas), renal cell carcinomas, glioblastomas and breast adeno-carcinomas.

As noted above, a variety of anti-tumor agents may be utilized in accordance with the disclosure. Within the context of the disclosure, "anti-tumor agents" are understood to refer to compounds or molecules which inhibit the growth of a selected tumor as discussed above. Representative examples of anti-tumor agents include immune activators and tumor proliferation inhibitors. Briefly, immune activators function by improving immune recognition of tumor-specific antigens such that the immune system becomes "primed." Priming may consist of lymphocyte proliferation, differentiation, or evolution to higher affinity interactions. The immune system thus primed will more effectively inhibit or kill tumor cells. Immune activation may be subcategorized into immune modulators (molecules which affect the interaction between lymphocyte and tumor cell) and lymphokines, that act to proliferate, activate, or differentiate immune effector cells. Representative examples of immune modulators include CD3, ICAM-1, ICAM-2, LFA-1, LFA-3, β-2-microglobulin, chaperones, interferon-a and -γ, B7/BB1 and major histocompatibility complex (MHC). Representative examples of lymphokines include gamma interferon, tumor necrosis factor, IL-1, IL-2, IL-3, IL4, IL-5, IL-6, IL-7, IL-8, IL-9, IL-10, IL-11, IL-12, IL-15, IL-23 GM-CSF, CSF-1, and G-CSF. The coding sequences for all of these factors are well known in the art.

Sequences which encode the above-described anti-tumor agents may be obtained from a variety-of sources from public data bases such as Genbank or PubMed and can be synthesized de novo by commercial vendors. Alternatively the sequence can be PCR amplified and cloned from cDNA libraries by methods well known to those skilled in the art. Plasmids that contain sequences which encode anti-tumor agents may be obtained in the same ways or from a depository such as the American Type Culture Collection (ATCC, Manasassas, Va.), Representative sources sequences which encode the above-noted anti-tumor agents include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains sequences encoding beta interferon), ATCC No 67024 (which contains a sequence which encodes Interleukin-1β), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6).

In addition to the anti-tumor agents described above, the disclosure also provides anti-tumor agents which comprise a fusion protein of, for example, two or more cytokines, immune modulators, toxins or differentiation factors. Preferred anti-tumor agents in this regard include alpha interferon—Interleukin-2, GM-CSF-IL-4, GM-CSF-IL-2, GM-CSF-IL-3 (see U.S. Pat. Nos. 5,082,927 and 5,108,910), GM-CSF—gamma interferon, and gamma interferon—IL-4. Within a particularly preferred embodiment, the anti-tumor agent is a gamma interferon-Interleukin-2 fusion protein. The construction of these anti-tumor agent(s) may be readily accomplished given the disclosure provided herein. The construction of a particularly preferred anti-tumor agent, gamma interferon—Interleukin-2, is described in more detail below in Example 1F.

Tumor proliferation inhibitors act by directly inhibiting cell growth, or by directly killing the tumor cell. Representative examples of tumor proliferation inhibitors include toxins such as ricin (Lamb et al., Eur. J. Biochem. 148:265-270, 1985), abrin (Wood et al., Eur. J. Biochem. 198:723-732, 1991; Evensen, et al., J. of Biol. Chem. 266:6848-6852, 1991: Collins et al., J. of Biol. Chem. 265:8665-8669, 1990; Chen et al, Fed. of Eur. Biochem Soc. 309:115-118, 1992), diphtheria toxin (Tweten et al., J. Biol. Chem. 260:10392-10394, 1985), cholera toxin (Mekalanos et al., Nature 306: 551-557, 1983; Sanchez & Holmgren, PNAS 86:481-485, 1989), gelonin (Stirpe et al., J. Biol. Chem. 255:6947-6953, 1980), pokeweed (Irvin, Pharmac. Ther. 21:371-387, 1983), antiviral protein (Barbieri et al., Biochem. J. 203:55-59, 1982; Irvin et al., Arch. Biochem. & Biophys. 200:418-425, 1980; Irvin, Arch. Biochem & Biophys. 169:522-528, 1975), tritin, *Shigella* toxin (Calderwood et al., PNAS 84:4364-4368, 1987; Jackson et al., Microb. Path. 2:147-153, 1987), and *Pseudomonas* exotoxin A (Carroll and Collier, J. Biol. Chem. 262:8707-8711, 1987), herpes simplex virus thymidine kinase (HSVTK) (Field et al., J. gen. Virol. 49:115-124, 1980), cytosine deaminases, and *E. coli*. guanine phosphoribosyl transferase. Additional examples of tumor proliferation inhibitors include antisense, siRNA and miRNA sequences which inhibit tumor cell growth by preventing the cellular synthesis of critical proteins needed for cell growth or inhibiting antagonists of immune potentiating agents. Examples of antisense sequences include antisense thymidine kinase, antisense dihydrofolate reductase (Maher and Dolnick, Arch. Biochem. & Biophys. 253:214-220, 1987; Bzik et al., PNAS 84:8360-8364, 1987), antisense HER2 (Coussens et al., Science 230:1132-1139, 1985), antisense ABL (Fainstein, et al., Oncogene 4:1477-1481, 1989), antisense Myc (Stanton et al., Nature 310:423-425, 1984) and antisense ras, as well as antisense sequences which block any of the enzymes in the nucleotide biosynthetic pathway. Finally, tumor proliferation inhibitors also include tumor suppressors such as p53, retinoblastoma (Rb), and MCC and APC for colorectal carcinoma.

Packaging cell lines suitable for use with the above-described retroviral vector constructs may be readily prepared (see, e.g., PCT Patent Publication No. WO 2010/148203, PCT Patent Publication No. WO 95/30763; and PCT Patent Publication No. WO 92/05266, the disclosure of which are incorporated herein), and utilized to create producer cell lines (also termed vector producer cell lines or "VCLS") for the production of recombinant vector particles. Within some embodiments, the packaging cell lines are made from human (e.g., HT1080 cells) thereby allowing production of recombinant retroviruses that are capable of surviving inactivation in human serum. In some embodiments of this disclosure, the packaging cell lines lack a function interferon gamma pathway to promote optimal viral production.

Mouse models are routinely used to test biological agents. The vector of the disclosure can be analyzed using mouse models. For example, mouse tumor systems may be utilized to show that cell mediated immune responses can be enhanced by direct administration of a vector construct which expresses at least one anti-tumor agent. For example, six to eight week old female Balb/C or C57Bl/6 mice can be injected subcutaneously with $1\times10^5$ to $2\times10^5$ tumor cells (CT26 or B16F10 respectively) which are allowed to grow within the mice for one to two weeks. The resulting tumors can be of variable size (usually 1-4 $mm^3$ in volume) so long as the graft is not compromised by either infection or ulceration. Five to two hundred microliters of a vector construct of the disclosure, which expresses an anti-tumor agent such as, for example, IFNγ, (minimum titer $10^6$ TU/ml) is then injected intratumorally. Multiple injections of the vector are given to the tumor every two to three days. Depending on the parameters of the particular experiment, the nature of the vector preparations can be variable as well. The vector can be from filtered or unfiltered supernatant from vector producing cell lines (VCL), or may be processed further by filtration, concentration or dialysis and formulation. Other standard purification techniques, such as gel filtration and ion exchange chromatography may also be utilized to purify the vector. For example, dialysis can be used to eliminate IFNγ that has been produced by the VCL itself (and which, if administered, may effect tumor growth).

Dialysis may also be used to remove possible inhibitors of transduction. Another option is to perform intratumor injections of the IFNγ VCL itself, in order to more extensively introduce the vector. Briefly, cells can be injected after being spun down from culture fluid and resuspended in a pharmaceutically acceptable medium (e.g., PBS plus 1 mg/ml HSA). As few as $10^5$ cells may be used in such an embodiment. Efficacy of the vector construct may be determined by measuring the reduction in primary tumor growth, the reduction in tumor burden (as determined by decreased tumor volume), or by the induction of increased T-cell activity against tumor target cells (as measured in an in vitro assay system using lymphocytes isolated from the spleens of these tumor bearing animals). In a metastatic murine tumor model, efficacy may also be determined by first injecting tumor cells that are metastatic, and, when the tumor is 1-4 $mm^3$ in volume, injecting vector several times into that tumor. The primary tumor graft may then be surgically removed after 2-3 weeks, and the reduction in metastases to the established target organ (lung, kidney, liver, etc.) counted. To measure the change in metastases in a target organ, the organ can be removed, weighed, and compared to a non-tumor bearing organ. In addition, the amount of metastases in the target organ can be measured by counting the number of visible metastatic nodules by using a low powered dissecting microscope.

For humans, the location for direct administration of a vector construct depends on the location of the tumor or tumors. The human IFNγ gene or other sequences which encode anti-tumor agents can be introduced directly into solid tumors by vector administration (the vectors may be purified as previously described). They may also be delivered to leukemias, lymphomas or ascites tumors. For skin lesions such as melanomas, the vector may be directly injected into or around the lesion. At least $10^5$ TU of vector particles should be administered, typically more than $10^5$ TU in a pharmaceutically acceptable formulation (e.g., 10 mg/ml mannitol, 1 mg/ml HAS, 25 mM Tris pH 7.2 and 105 mM NaCl). If a companion 5-FC course is used subjects are dose for 1 week at 150 mg/kg/day. For internal tumor lesions, the affected tumor can be localized by X-ray, CT scan, antibody imaging or other methods known to those skilled in the art of tumor localization. Vector injection can be through the skin into internal lesions, or by adaptations of bronchoscopy (for lungs), colonoscopy (for colorectal or esophageal tumors) or intra-arterial or intra-blood vessel catheter (for many types of vascularized solid tumors). The injection can be into or around the tumor lesion. The efficiency of induction of a biological response may be measured by CTL or other T cell assay or by delayed type hypersensitivity (DTH) reactions to the tumor. Efficacy and clinical responses may be determined by measuring the tumor burden using X-ray, CT scan or antibody imaging or other methods known to those skilled in the art of tumor localization.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) Gene 105:61-72). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508; E. Angov Biotechnol J. 6: 650-659 2011, doi: 10.1002/biot.201000332) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA, respectively. The preferred stop codon for monocotyledonous plants is UGA, whereas insects and *E. coli* prefer to use UAA as the stop codon (Dalphin et al. (1996) Nucl. Acids Res. 24: 216-218).

Codon usage bias refers to differences among organisms in the frequency of occurrence of codons in protein-coding DNA sequences (genes). A codon is a series of three nucleotides (triplets) that encodes a specific amino acid residue in a polypeptide chain. Because there are four nucleotides in DNA, adenine (A), guanine (G), cytosine (C) and thymine (T), there are 64 possible triplets encoding 20 amino acids, and three translation termination (nonsense) codons. Because of this redundancy, all but two amino acids are encoded by more than one triplet. Different organisms often show particular preferences for one of the several codons that encode the same amino acid. How these preferences arise is a much debated area of molecular evolution.

It is generally acknowledged that codon preferences reflect a balance between mutational biases and natural selection for translational optimization. Optimal codons in fast-growing microorganisms, like *Escherichia coli* or *Saccharomyces cerevisiae* (baker's yeast), reflect the composition of their respective genomic tRNA pool. It is thought that optimal codons help to achieve faster translation rates and high accuracy. As a result of these factors, translational selection is expected to be stronger in highly expressed genes, as is indeed the case for the above-mentioned organisms. In other organisms that do not show high growing rates or that present small genomes, codon usage optimization is normally absent, and codon preferences are determined by the characteristic mutational biases seen in that particular genome. Examples of this are *Homo sapiens* (human) and *Helicobacter pylori*. Organisms that show an intermediate level of codon usage optimization include *Drosophila melanogaster* (fruit fly), *Caenorhabditis elegans* (nematode worm) or *Arabidopsis thaliana* (wall cress).

TABLE 3 human codon usage and codon preference. For each codon, the table displays the frequency of usage of each codon (per thousand) in human coding regions (first column) and the relative frequency of each codon among synonymous codons (second column).

The Human Codon Usage Table

| | | | | | | | | | | | | | | | |
|---|---|---|---|---|---|---|---|---|---|---|---|---|---|---|---|
| Gly | GGG | 17.08 | 0.23 | Arg | AGG | 12.09 | 0.22 | Trp | TGG | 14.74 | 1.00 | Arg | CGG | 10.40 | 0.19 |
| Gly | GGA | 19.31 | 0.26 | Arg | AGA | 11.73 | 0.21 | End | TGA | 2.64 | 0.61 | Arg | CGA | 5.63 | 0.10 |
| Gly | GGT | 13.66 | 0.18 | Ser | AGT | 10.18 | 0.14 | Cys | TGT | 9.99 | 0.42 | Arg | CGT | 5.16 | 0.09 |

TABLE 3-continued human codon usage and codon preference. For each codon, the table displays the frequency of usage of each codon (per thousand) in human coding regions (first column) and the relative frequency of each codon among synonymous codons (second column).
The Human Codon Usage Table

| | | | | | | | | | | | | | | | |
|---|---|---|---|---|---|---|---|---|---|---|---|---|---|---|---|
| Gly | GGC | 24.94 | 0.33 | Ser | AGC | 18.54 | 0.25 | Cys | TGC | 13.86 | 0.58 | Arg | CGC | 10.82 | 0.19 |
| Glu | GAG | 38.82 | 0.59 | Lys | AAG | 33.79 | 0.60 | End | TAG | 0.73 | 0.17 | Gln | CAG | 32.95 | 0.73 |
| Glu | GAA | 27.51 | 0.41 | Lys | AAA | 22.32 | 0.40 | End | TAA | 0.95 | 0.22 | Gln | CAA | 11.94 | 0.27 |
| Asp | GAT | 21.45 | 0.44 | Asn | AAT | 16.43 | 0.44 | Tyr | TAT | 11.80 | 0.42 | His | CAT | 9.56 | 0.41 |
| Asp | GAC | 27.06 | 0.56 | Asn | AAC | 21.30 | 0.56 | Tyr | TAC | 16.48 | 0.58 | His | CAC | 14.00 | 0.59 |
| Val | GTG | 28.60 | 0.48 | Met | ATG | 21.86 | 1.00 | Leu | TTG | 11.43 | 0.12 | Leu | CTG | 39.93 | 0.43 |
| Val | GTA | 6.09 | 0.10 | Ile | ATA | 6.05 | 0.14 | Leu | TTA | 5.55 | 0.06 | Leu | CTA | 6.42 | 0.07 |
| Val | GTT | 10.30 | 0.17 | Ile | ATT | 15.03 | 0.35 | Phe | TTT | 15.36 | 0.43 | Leu | CTT | 11.24 | 0.12 |
| Val | GTC | 15.01 | 0.25 | Ile | ATC | 22.47 | 0.52 | Phe | TTC | 20.72 | 0.57 | Leu | CTC | 19.14 | 0.20 |
| Ala | GCG | 7.27 | 0.10 | Thr | ACG | 6.80 | 0.12 | Ser | TCG | 4.38 | 0.06 | Pro | CCG | 7.02 | 0.11 |
| Ala | GCA | 15.50 | 0.22 | Thr | ACA | 15.04 | 0.27 | Ser | TCA | 10.96 | 0.15 | Pro | CCA | 17.11 | 0.27 |
| Ala | GCT | 20.23 | 0.28 | Thr | ACT | 13.24 | 0.23 | Ser | TCT | 13.51 | 0.18 | Pro | CCT | 18.03 | 0.29 |
| Ala | GCC | 28.43 | 0.40 | Thr | ACC | 21.52 | 0.38 | Ser | TCC | 17.37 | 0.23 | Pro | CCC | 20.51 | 0.33 |

As previously discussed, general texts, and commercial, non-profit and academic web sites which describe molecular biological techniques useful herein, including the use of vectors, promoters and many other relevant topics, include Current Protocols ([www.]_[currentprotocols.com; [www.]_[springerprotocols.com; [http://]_[cshprotocols.chslp.org/; Nature Protocols ([http://www.][nature.com/nprot/index-.html; Methods in Enzymology series ([http://www.][else-vier.com/books/book-series/methods-in-enzymology).

In another embodiment, the disclosure provides a method of treating a subject having a cell proliferative disorder. The subject can be any mammal, and is preferably a human. The subject is contacted with a recombinant vector of the disclosure. The contacting can be in vivo or ex vivo. Methods of administering the vector of the disclosure are known in the art and include, for example, systemic administration, topical administration, intraperitoneal administration, intramuscular administration, intracranial, cerebrospinal, as well as administration directly at the site of a tumor or cell-proliferative disorder. Other routes of administration known in the art.

Infectious vector for in vitro and small scale use were made by transient transfection of target cells as described. Typically this give s titers of 2×10^6 to 2×10^7 Transducing Units(TU)/ml. The vector can be used as a crude preparation or further purified as described in WO2010148203. Infectious vector can also be made using a permanent producer cell line and grown in serum free and/or suspension culture to generate crude harvests of several hundred liters and purified material in a clinically acceptable formulation as described (WO2010/148203). Purified material typically has titers of about 10^9 TU/ml.

The vectors of this disclosure can be used according to the properties of the target tumor. Treatment is usually includes an ablative step in conjunction with one or two differently targeted siRNA molecules. The ablative step can be through use of 5-FC administration after administration of a vector encoding anti-PD-L1 siRNA and cytosine deaminase. Alternatively ablation can be through chemotherapy before or after administration of a vector encoding both anti-PD-L1 siRNA and anti-IDO-1 siRNA. The chemotherapy can be with any drug known to allow rapid immune recovery or preferential recovery of activated immune cells over immune suppressive immune cells such as Temolozolomide or Cyclophosphamide (T regs) or 5-FC/5-FU (5-FU is preferentially toxic to Myeloid derived suppressor cells.

The vectors described here allow the long term delivery of pairs of agents, which are known to be advantageous as opposed to administration of a single agent. The vectors can be delivered intratumorally, into resection cavities after resection or Intravenously. Intratumoral or resection cavity injection can cause regression of the local lesion, but also lead to systemic effects, with control of remote lesions through immune responses. Intratumoral or resection cavity doses can be between 10^6 TU to 10^11 TU, with a single injection or alternatively with serial administration spaced between 3, 6, 12, 24 or 36 months. IV administration uses doses that are up to 1,000 fold higher, but more likely about 100 or 10 fold higher. IV vector is preferably delivered on multiple sequential days, for example, each of 3 days or each of 5 days or each of 7 days as in animals (Huang et al., Hum Gen Ther 26:82-93, 2015). Alternatively the delivery can be on multiple days that are not sequential.

Thus, the disclosure includes various pharmaceutical compositions useful for treating a cell proliferative disorder. The pharmaceutical compositions according to the disclosure are prepared by bringing a vector containing a heterologous polynucleotide sequence useful in treating or modulating a cell proliferative disorder according to the disclosure into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The following Examples are intended to illustrate, but not to limit the disclosure. While such Examples are typical of those that might be used, other procedures known to those skilled in the art may alternatively be utilized.

EXAMPLES

Human tumor infiltrating lymphocytes (TIL) can produce tumor-specific immune responses when stimulated with cognate cellular targets. Specifically, targets such as tumors or antigen-presenting cells expressing a tumor-specific antigenic peptide presented in the context of a matched HLA molecule can bind to the T-cell receptor (TCR) on the TIL, which initiates a signaling cascade ultimately driving the TIL to proliferate, express cell-surface activation markers and produce effector cytokines such as TNF-alpha and interferon gamma (IFNg, Smith-Garvin et al., Annu Rev Immunol 27: 591-619, 2009). TILs interacting with matched tumors can be useful tools to understand basic immunological mechanisms or evaluate immunological parameters of an experimental immunotherapy.

Example 1: IDO1 Expression is Induced by IFNγ in Glioma

Figure 2:
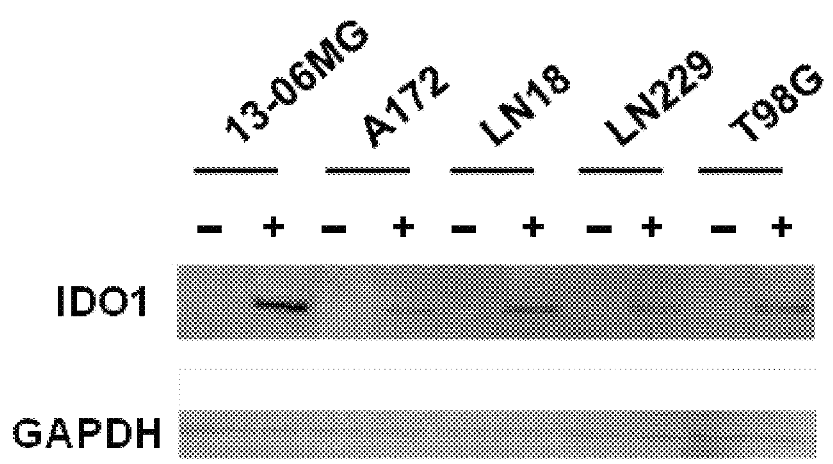
FIG. 2 shows IDO1 protein expression in various glioma cell lines.

IDO1 expression known to be upregulated in gliomas and is induced by IFNγ. A panel of glioma cell lines were surveyed for their IDO1 expression after IFNγ induction. FIG. 2 shows that IDO1 (anti-human IDO1 at 1:1500, Cell Signaling) is upregulated by IFNγ and the level of induction varies among glioma cell lines. GAPDH (anti-human GAPDH at 1:500, Cell Signaling) detection was included as a loading control.

Figure 3:
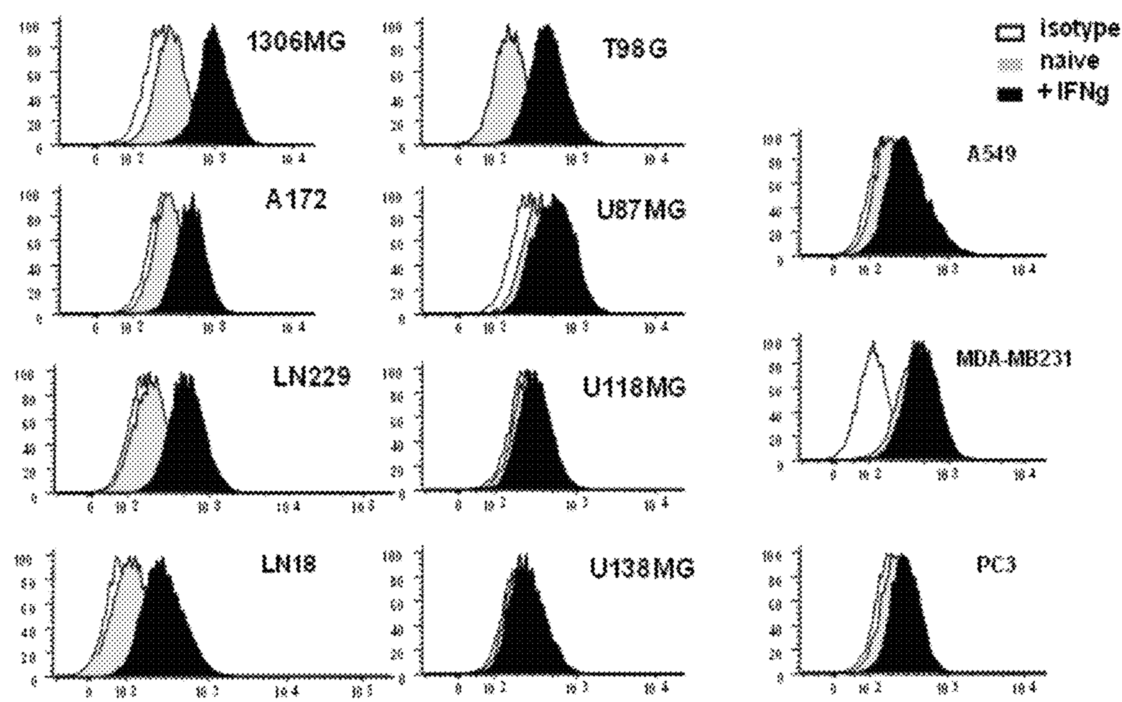
FIG. 3 shows PD-L1 cell surface expression in various cancer cell lines.

Example 2: PD-L1 Cell Surface Expression is Induced by IFNγ in Glioma and Other Tumor Cell Lines PDL1 expression is known to be upregulated in glioma and other tumor cell lines. Its expression can be further induced by IFNγ. A panel of cancer cell lines including glioma cell lines is surveyed for their PDL1 expression (anti-human PD-L1 antibody, eBioscience) before and after IFNγ induction. FIG. 3 shows that the basal expression of PDL1 varies among cell lines and that most of the cells lines, but not all, tested here are responsive to IFNγ to further induce PDL1 expression.

Figure 4:
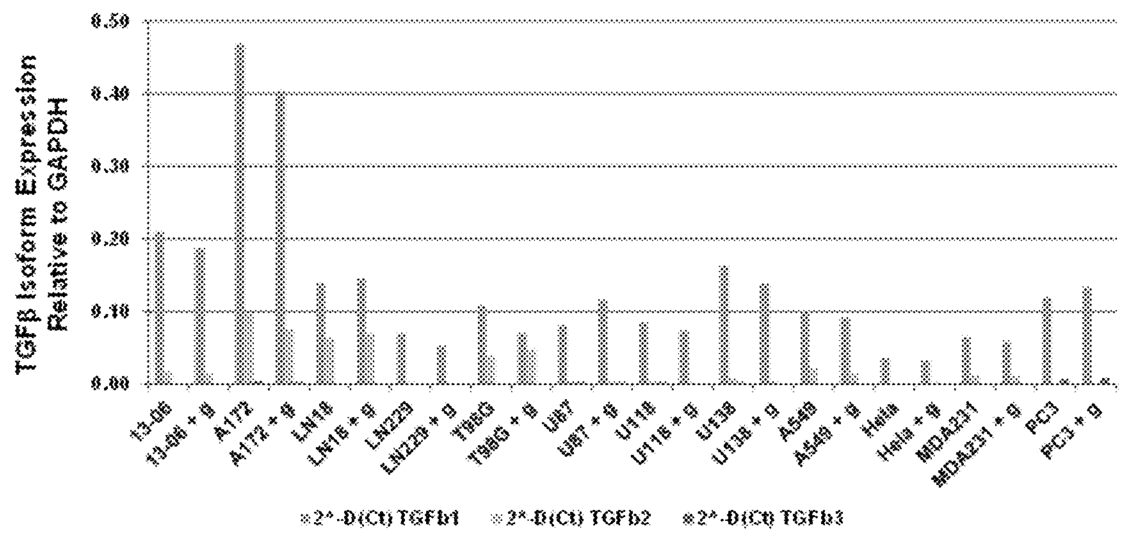
FIG. 4 shows gene expression of TGFβ1, 2 and 3 isoforms in various cancer cell lines.

Example 3: TGFβ1 and 2 Expressions are Upregulated in a Panel of Glioma and Other Tumor Cell Lines TGFβ1 and TGFβ2 expression is known to be upregulated in glioma and other tumor cell lines. A panel of cancer cell lines including glioma cell lines were surveyed for their TGFβ1, 2 and 3 expression before and after IFNγ treatment using human TGF isoform-specific Taqman primers (Life Technology). FIG. 4 shows that TGFβ1, 2 and 3 expression levels vary among cell lines. Some expression more TGFβ1 and others express more TGFβ2. In all cases, TGFβ3 expression is low. In contrast to IDO1 and PDL1, TGFβ1, 2 and 3 expression is not induced by IFNγ.

Example 4: Cloning and Characterization of pAC3-U6shRNA and pAC3-U6miR30shRNAs Against IDO1, PDL1 and TGFβ2

Figure 5:
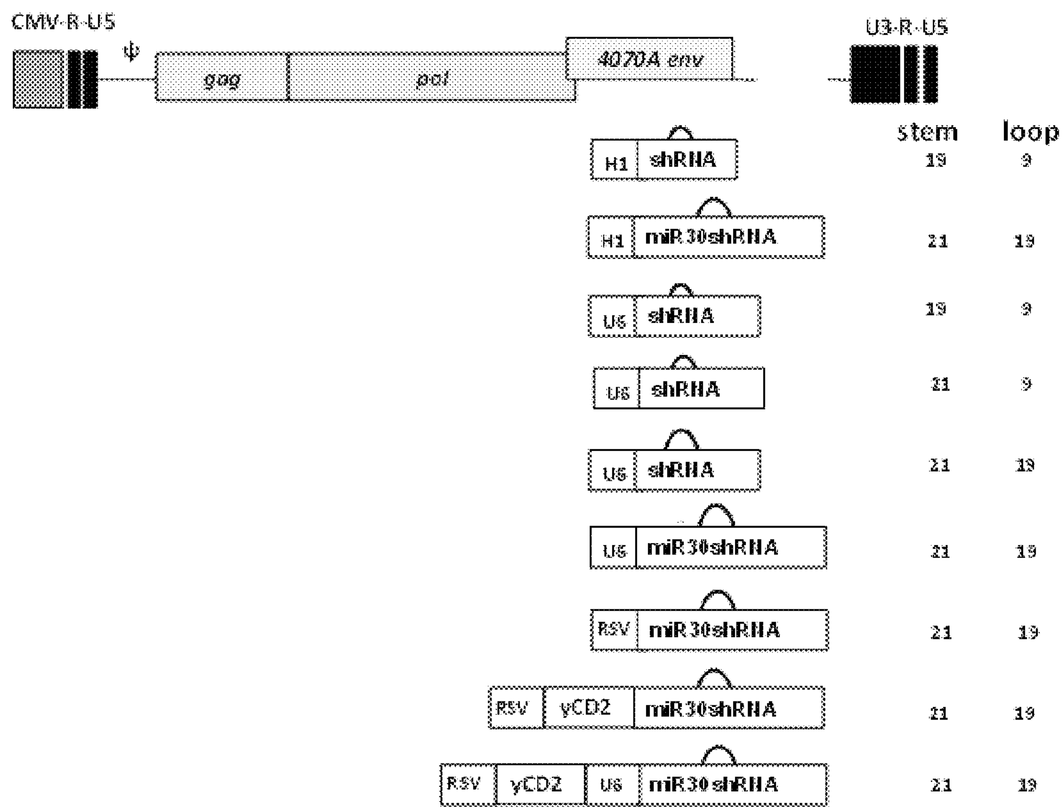
FIG. 5 shows schematics of RRV-shRNA vectors of the disclosure.

The replication competent retroviral vectors, pAC3-U6-miR30shRNA, were derived from the backbone of pAC3-yCD2 (SEQ ID NO:1). The pAC3 backbone was isolated by endonuclease digestion of the pAC3-yCD2 plasmid DNA with Mlu I and Not I. The U6-shRNA cassette contains a human U6 promoter and target-specific shRNA sequence targeting IDO1, PDL1 and TGFβ2. The U6-miR30shRNA cassette contains a U6 promoter and target-specific shRNA sequence embedded in microRNA30 (miR30) backbone targeting IDO1, PDL1 and TGFβ2 (FIG. 5). Each U6miR30shRNA DNA fragment was synthesized with Mlu I and Not I restriction enzyme site present at each end of the DNA fragment for subsequent insertion at the corresponding site in the pAC3 backbone.

Vector stock was produced by transient transfection of the vector-encoding plasmid DNA into 293T cells using calcium phosphate method. Forty-eight hours post transfection, the supernatant containing the vector was collected and filtered through a 0.45 μm syringe filter and used immediately or stored in aliquots at −80° C. for later use. Titer values from these vectors were determined on PC3 cells by qPCR method using the primer set (5-MLV-U3-B: 5'-AGCCCACAACCCCTCACTC-3' (SEQ ID NO:2), 3-MLV-Psi: 5'-TCTCCCGATCCCGGACGA-3' (SEQ ID NO:3). Probe: FAM-5'-CCCCAAATGAAAGACCCCCGCTGACG-3'-BHQ1 (SEQ ID NO:4)). Twenty microliters of the collected vector stocks was used to infect human prostate cancer cells, PC3. Forty-eight hours post infection, genomic DNA of infected PC3 cells was extracted for titer assay. The titer of the vector stocks was determined by qPCR with an inclusion of standards of known copy numbers.

A MOI of 0.1 was used to infect LN18 cells which are known to express marked level of IDO1, PDL1 and TGFb2. The knockdown activity of miR30shRNA for each specific target gene was measured directly at the protein level. Approximately at day 14 post infection, cells infected with pAC3-U6-30shRNA and pAC3-U6miR30shRNA vectors were harvested for different assays, depending upon the target gene of interest, to measure the shRNA knockdown activity.

Figure 6:
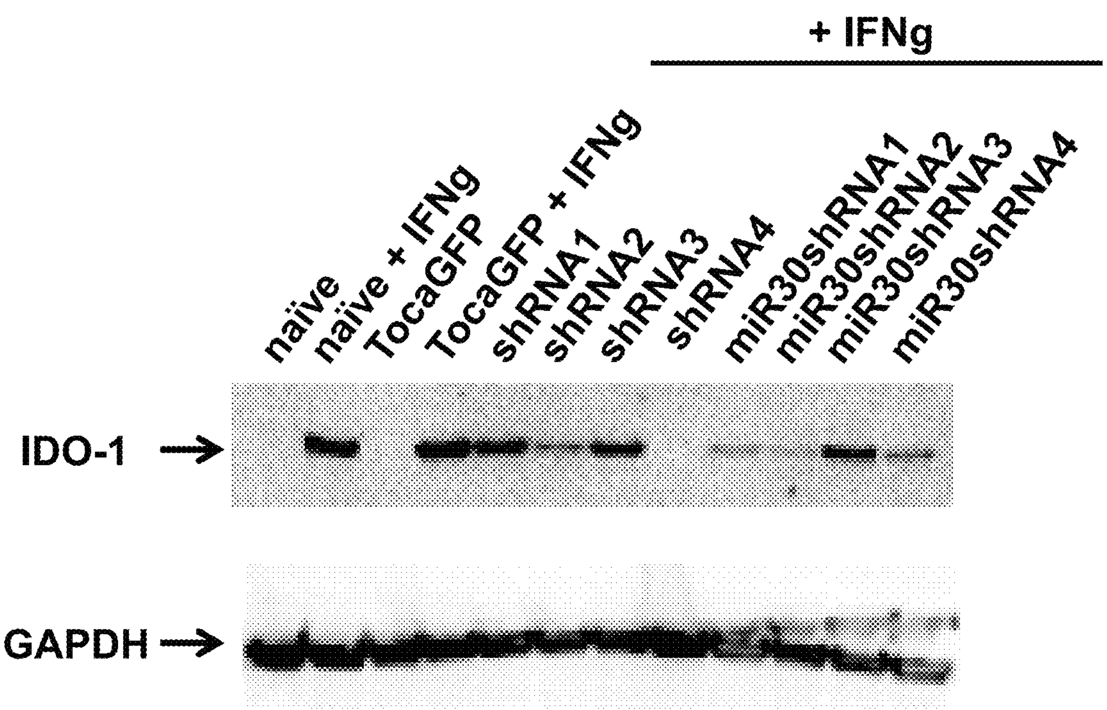
FIG. 6 shows knockdown of IDO1 expression by RRV-U6-IDO1shRNA and RRV-U6-IDO1miR30shRNA.
Figure 7:
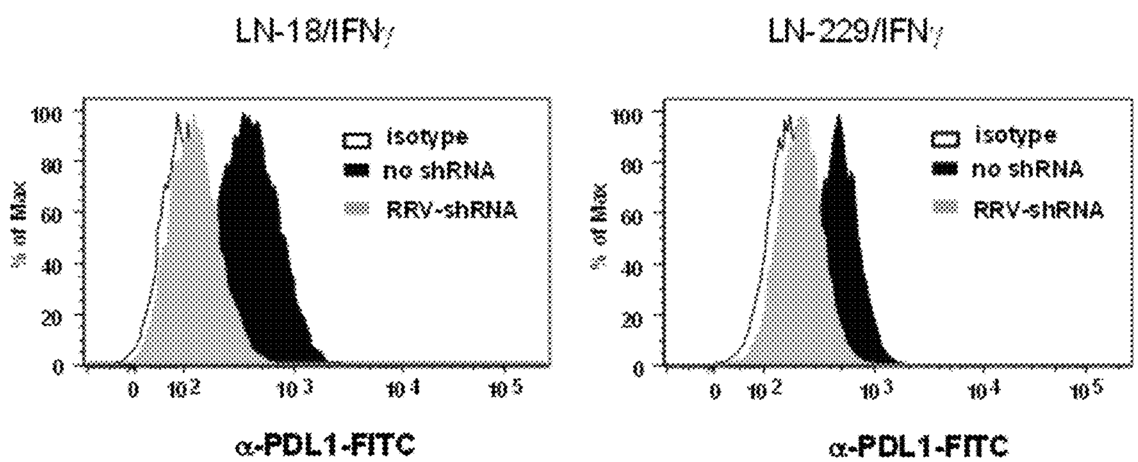
FIG. 7 shows knockdown of PDL1 cell surface expression by RRV-U6-PDL1shRNA and RRV-U6-PDL1miRshRNA.
Figure 8:
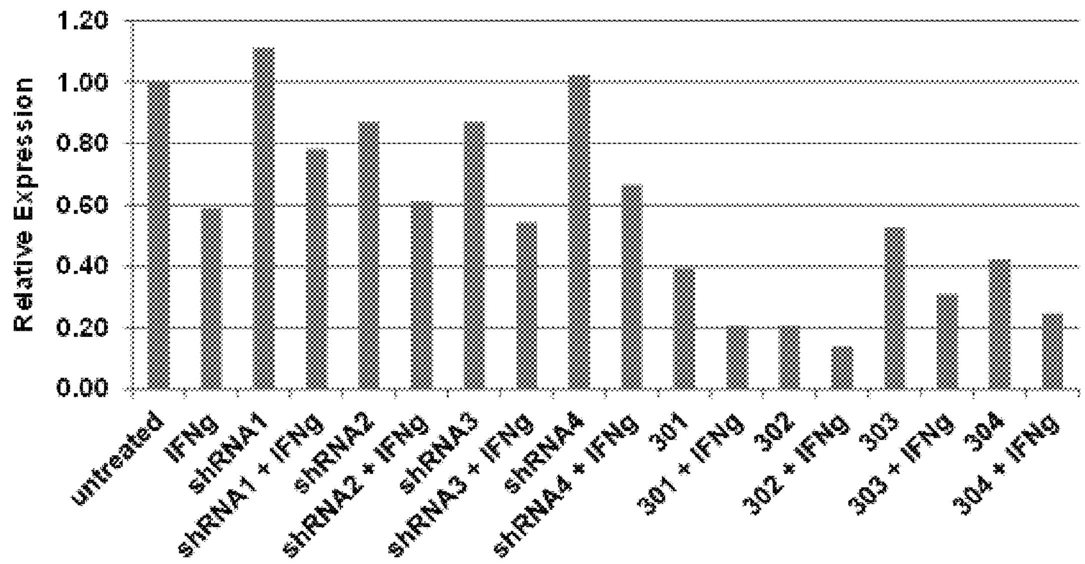
FIG. 8 shows knockdown of TGFβ2 expression by RRV-U6-TGFb2shRNA and RRV-U6-TGFb2miRshRNA.

LN18 cells infected with pAC3-U6-IDO1shRNA or pAC3-U6-IDO1miR30shRNA vectors were harvested for qualitative analysis of IDO1 expression level after IFNγ induction. FIG. 6 shows that pAC3-U6-IDO1shRNA2, pAC3-U6-IDO1miR30shRNA1 and pAC3-U6-IDOmiR30shRNA2 have greater than 50% knockdown activity against IDO1 compares to that of uninfected cells. Likewise, LN18 and LN229 cells infected with pAC3-U6-PDL1miR30shRNA4 vector also have greater than 50% knockdown activity (FIG. 7). For measurement of TGFβ2 knockdown activity, LN18 cells uninfected or fully infected with pAC3-U6-TGFb2shRNA1, pAC3-U6-TGFb2shRNA2 or pAC3-U6-TGFb2shRNA3 vectors are seeded with same number of cells in T25 flask. Supernatant from confluent cell density was collected to measure the level of bioactive TGFβ2 by ELISA (R & D Systems). FIG. 8 shows that pAC3-U6-TGFb2shRNA1, pAC3-U6-TGFb2shRNA2 and pAC3-U6TGFb2shRNA4 have greater than 50% knockdown activity. In addition, IFNγ treatment and shRNA have synergistic effect on TGFβ2 downregulation.

The vector stability of some pAC3-U6-miR30shRNA vectors against IDO1, PDL1 or TGFβ2 described above was evaluated by end-point PCR in infected LN18 cells. Cells infected with vectors at an MOI of 0.1 are passaged in culture for up to 21 days. Genomic DNA was extracted from infected cells followed by end point PCR using primer set spanning the 3' env and 3'UTR region (UCLA-5-127: 5'-CTGATCTTACTCTTTGGACCTTG-3' (SEQ ID NO:5); UCLA-3-37: 5'-CCCCTTTTTCTGGAGACTAAATAA-3'

Figure 9:
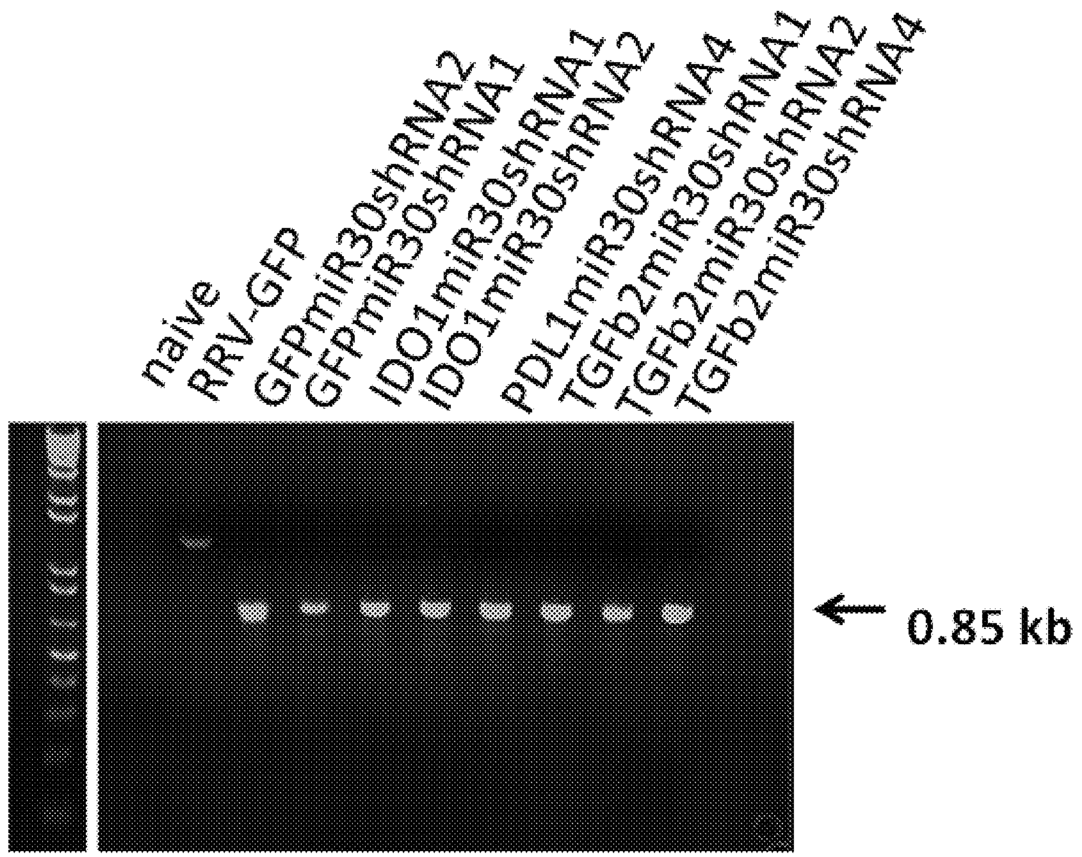
FIG. 9 shows vector stability of RRV-U6-miR30shRNA vectors targeting IDO1, PDL1 and TGFβ2.

(SEQ ID NO:6)). FIG. 9 shows that pAC3-U6-IDO1miR30shRNA1, pAC3-U6-IDO1miR30shRNA2, pAC3-U6-PDL1miR30shRNA4, pAC3-U6-TGFb2miR30shRNA1, pAC3-U6-TGFb2miR30shRNA2, and pAC3-U6-TGFb2miR30shRNA4 are stable in LN18 cells.

Example 5: Cloning and Characterization of pAC3-H1-miR30shRNAs Against IDO1, PDL1

The replication competent retroviral vectors, pAC3-H1-IDO1miR30shRNA and pAC3-H1-PDL1miR30shRNA, are derived from the backbone of pAC3-yCD2 (SEQ ID NO:1). The pAC3 backbone was isolated by endonuclease digestion of the pAC3-yCD2 plasmid DNA with Mlu I and Not I. The H1-miR30shRNA cassette contains a human H1 promoter and target-specific shRNA sequence targeting IDO1 and PDL1 (FIG. 5). Each H1miR30shRNA DNA fragment was synthesized with Mlu I and Not I restriction enzyme site present at each end of the DNA fragment for subsequent insertion at the corresponding site in the pAC3 backbone.

Vector stock was produced by transient transfection of the vector-encoding plasmid DNA into 293T cells using calcium phosphate method. Forty-eight hours post transfection, the supernatant containing the vector were collected and filtered through a 0.45 μm syringe filter and used immediately or stored in aliquots at −80° C. for later use. Titer values from these vectors were determined on PC3 cells by qPCR method using the primer set (5-MLV-U3-B: 5'-AGCC-CACAACCCCTCACTC-3' (SEQ ID NO:2), 3-MLV-Psi: 5'-TCTCCCGATCCCGGACGA-3' (SEQ ID NO:3). Probe: FAM-5'-CCCCAAATGAAAGACCCCCGCTGACG-3'-BHQ1 (SEQ ID NO:4)). Twenty microliters of the collected vector stocks was used to infect human prostate cancer cells, PC3. Forty-eight hours post infection, genomic DNA of infected PC3 cells was extracted for titer assay. The titer of the vector stocks was determined by qPCR with an inclusion of standards of known copy numbers.

A MOI of 0.1 was used to infect LN18 cells which are known to express marked level of IDO1 and PDL1. The knockdown activity of miR30shRNA for each specific target gene was measured directly at the protein level. Approximately at day 14 post infection, cells infected with pAC3-H1-miR30shRNA vectors were harvested for different assays, depending upon the target gene of interest, to measure the shRNA knockdown activity.

Figure 10:
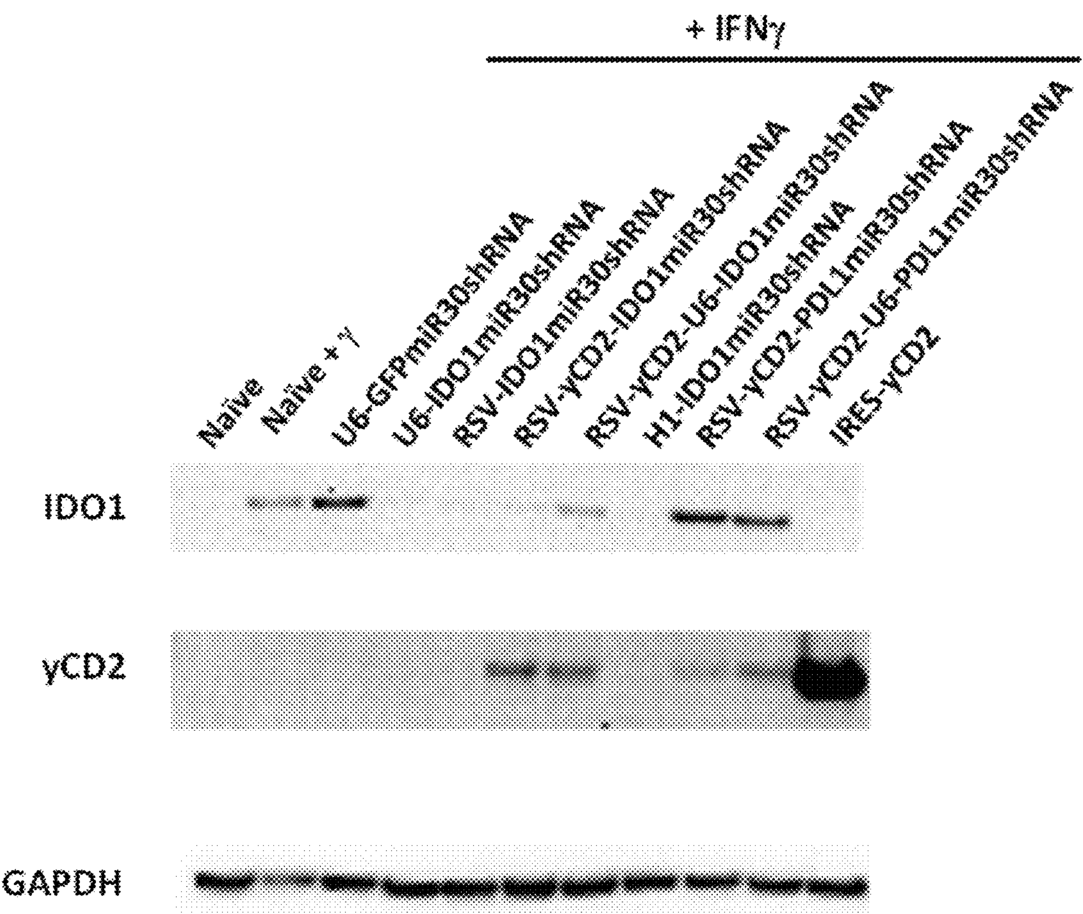
FIG. 10 shows knockdown of IDO1 expression by RRV-H1-IDO1miR30shRNA, RRV-RSV-IDO1miR30shRNA, RRV-RSV-yCD2-IDO1miR30shRNA and RRV-RSV-yCD2-U6-IDO1miR30shRNA.
Figure 11:
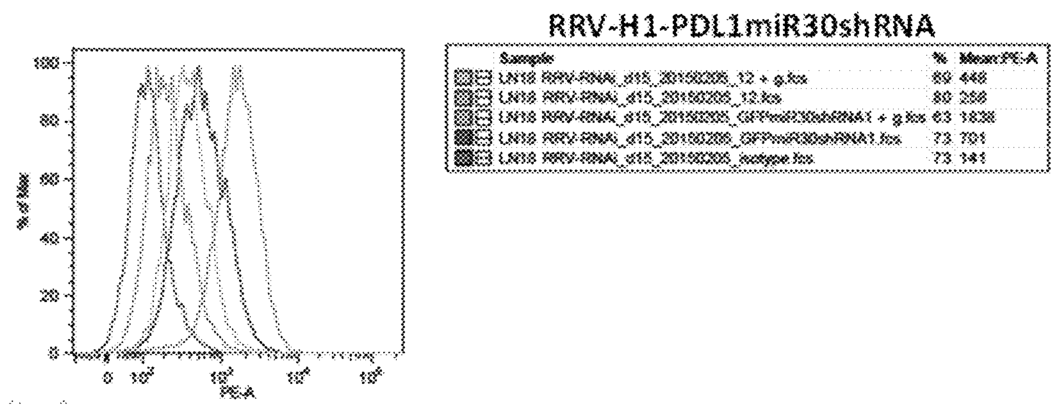
FIG. 11 shows knockdown of PDL1 cell surface expression by RRV-H1-PDL1miR30shRNA.

LN18 cells infected with pAC3-H1IDO1shRNA vectors were harvested for qualitative analysis of IDO1 expression level after IFNγ induction. FIG. 10 shows that pAC3-H1-IDO1miR30shRNA2 has greater than 50% knockdown activity against IDO1 compares to that of uninfected cells. Likewise, LN18 cells infected with pAC3-H1-PDL1miR30shRNA4 vector also showed greater than 50% knockdown activity (FIG. 11).

Figure 12:
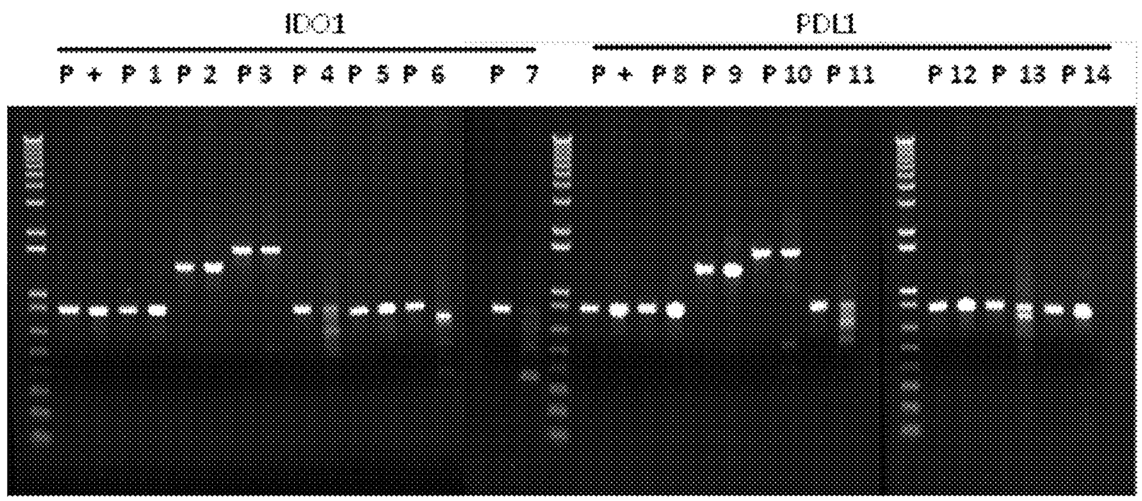
FIG. 12 shows vector stability of RRV-U6-miR30shRNA, RRV-H1-miR30shRNA, RRV-RSV-miR30shRNA, RRV-RSV-yCD2-miR30shRNA and RRV-RSV-yCD2-U6-miR30shRNA targeting IDO1 and PDL1.

The vector stability of some pAC3-H1-miR30shRNA vectors against IDO1 or PDL1 described above was evaluated by end-point PCR in infected LN18 cells. Cells infected with vectors at an MOI of 0.1 were passaged in culture for up to 21 days. Genomic DNA was extracted from infected cells followed by end point PCR using primer set spanning the 3' env and 3'UTR region (UCLA-5-127: 5'-CTGATCT-TACTCTTTGGACCTTG-3' (SEQ ID NO:5); UCLA-3-37: 5'-CCCCTTTTTCTGGAGACTAAATAA-3' (SEQ ID NO:6)). FIG. 12 shows that pAC3-H1-IDO1miR30shRNA2 and pAC3-H1-PDL1miR30shRNA4 are stable in LN18 cells.

Example 6: Cloning and Characterization of pAC3-RSV-miR30shRNAs Against IDO1, PDL1

The replication competent retroviral vectors, pAC3-RSV-IDO1miR30shRNA and pAC3-RSV-PDL1miR30shRNA, are derived from the backbone of pAC3-yCD2 (SEQ ID NO:1). The pAC3 backbone was isolated by endonuclease digestion of the pAC3-yCD2 plasmid DNA with Mlu I and Not I. The RSVmiR30shRNA cassette contains an RSV promoter and target-specific shRNA sequence targeting IDO1 and PDL1 (FIG. 5). Each RSVmiR30shRNA DNA fragment was synthesized with Mlu I and Not I restriction enzyme site present at each end of the DNA fragment for subsequent insertion at the corresponding site in the pAC3 backbone.

Vector stock was produced by transient transfection of the vector-encoding plasmid DNA into 293T cells using calcium phosphate method. Forty-eight hours post transfection, the supernatant containing the vector is collected and filtered through a 0.45 μm syringe filter and used immediately or stored in aliquots at −80° C. for later use. Titer values from these vectors were determined on PC3 cells by qPCR method using the primer set (5-MLV-U3-B: 5'-AGCC-CACAACCCCTCACTC-3' (SEQ ID NO:2), 3-MLV-Psi: 5'-TCTCCCGATCCCGGACGA-3' (SEQ ID NO:3). Probe: FAM-5'-CCCCAAATGAAAGACCCCCGCTGACG-3'-BHQ1 (SEQ ID NO:4)). Twenty micro-liter of the collected vector stocks was used to infect human prostate cancer cells, PC3. Forty-eight hours post infection, genomic DNA of infected PC3 cells was extracted for titer assay. The titer of the vector stocks was determined by qPCR with an inclusion of standards of known copy numbers.

A MOI of 0.1 was used to infect LN18 cells which are known to express marked level of IDO1 and PDL1. The knockdown activity of miR30shRNA for each specific target gene is measured directly at the protein level. Approximately at day 14 post infection, cells infected with pAC3-RSV-miR30shRNA vectors were harvested for different assays, depends on the target gene of interest, to measure the shRNA knockdown activity.

Figure 13:
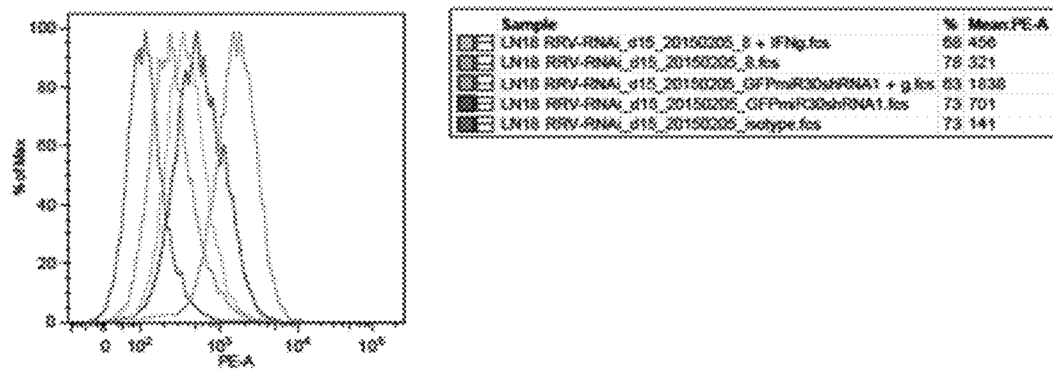
FIG. 13 shows knockdown of PDL1 cell surface expression by RRV-RSV-PDL1miR30shRNA.

LN18 cells infected with pAC3-RSV-IDO1shRNA vectors were harvested for qualitative analysis of IDO1 expression level after IFNγ induction. FIG. 10 shows that pAC3-RSV-IDO1miR30shRNA2 has greater than 50% knockdown activity against IDO1 compares to that of uninfected cells. Likewise, LN18 cells infected with pAC3-RSV-PDL1miR30shRNA4 vector also showed greater than 50% knockdown activity (FIG. 13).

The vector stability of some pAC3-RSV-PDL1miR30shRNA vectors against IDO1 or PDL1 described above were evaluated by end-point PCR in infected LN18 cells. Cells infected with vectors at an MOI of 0.1 are passaged in culture for up to 21 days. Genomic DNA was extracted from infected cells followed by end point PCR using primer set spanning the 3' env and 3'UTR region (UCLA-5-127: 5'-CTGATCT-TACTCTTTGGACCTTG-3' (SEQ ID NO:5); UCLA-3-37: 5'-CCCCTTTTTCTGGAGACTAAATAA-3' (SEQ ID NO:6)). FIG. 12 shows that pAC3-RSV-IDO1miR30shRNA2 and pAC3-RSV-PDL1miR30shRNA4 are stable in LN18 cells.

Example 7: Cloning and Characterization of pAC3-RSV-yCD2-IDO1miR30shRNA2 and pAC3-RSV-yCD2-PDL1miR30shRNA4

The replication competent retroviral vectors, pAC3-RSV-yCD2-IDO1miR30shRNA2 and pAC3-RSV-yCD2-

PDL1miR30shRNA4, are derived from the backbone of pAC3-yCD2 (SEQ ID NO:1). The pAC3 backbone was isolated by endonuclease digestion of the pAC3-yCD2 plasmid DNA with Mlu I and Not I. The RSV-yCD2-miR30shRNA cassette contains an RSV promoter and target-specific shRNA sequence targeting IDO1 and PDL1 (FIG. 5). Each RSV-yCD2-miR30shRNA DNA fragment was synthesized with Mlu I and Not I restriction enzyme site present at each end of the DNA fragment for subsequent insertion at the corresponding site in the pAC3 backbone.

Vector stock was produced by transient transfection of the vector-encoding plasmid DNA into 293T cells using calcium phosphate method. Forty-eight hours post transfection, the supernatant containing the vector was collected and filtered through a 0.45 μm syringe filter and used immediately or stored in aliquots at −80° C. for later use. Titer values from these vectors are determined on PC3 cells by qPCR method using the primer set (5-MLV-U3-B: 5'-AGCCCACAACCCCTCACTC-3' (SEQ ID NO:2), 3-MLV-Psi: 5'-TCTCCCGATCCCGGACGA-3' (SEQ ID NO:3). Probe: FAM-5'-CCCCAAATGAAAGACCCCCGCTGACG-3'-BHQ1 (SEQ ID NO:4)). Twenty micro-liter of the collected vector stocks was used to infect human prostate cancer cells, PC3. Forty-eight hours post infection, genomic DNA of infected PC3 cells was extracted for titer assay. The titer of the vector stocks was determined by qPCR with an inclusion of standards of known copy numbers.

A MOI of 0.1 was used to infect LN18 cells which are known to express marked level of IDO1 and PDL1. The knockdown activity of miR30shRNA for each specific target gene was measured directly at the protein level. Approximately at day 14 post infection, cells infected with pAC3-H1miR30shRNA vectors were harvested for different assays, depends on the target gene of interest, to measure the shRNA knockdown activity.

Figure 14:
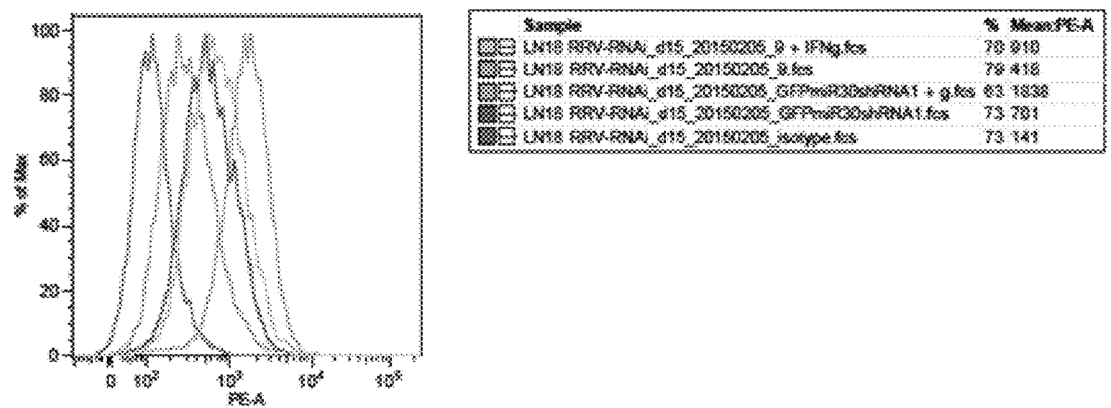
FIG. 14 shows knockdown of PDL1 cell surface expression by RRV-RSV-yCD2-PDL1miR30shRNA.

LN18 cells infected with pAC3-RSV-yCD2-IDO1miR30shRNA vectors were harvested for qualitative analysis of IDO1 expression level after IFNγ induction. FIG. 10 shows that pAC3-RSV-yCD2-IDO1miR30shRNA2 has greater than 50% knockdown activity against IDO1 compares to that of uninfected cells. Likewise, LN18 cells infected with pAC3-RSV-yCD2-PDL1miR30shRNA4 vector also showed approximately 50% knockdown activity (FIG. 14).

The vector stability of some pAC3-RSV-yCD2miR30shRNA vectors against IDO1 or PDL1 described above was evaluated by end-point PCR in infected LN18 cells. Cells infected with vectors at an MOI of 0.1 are passaged in culture for up to 21 days. Genomic DNA was extracted from infected cells followed by end point PCR using primer set spanning the 3' env and 3'UTR region (UCLA-5-127: 5'-CTGATCTTACTCTTTGGACCTTG-3' (SEQ ID NO:5); UCLA-3-37: 5'-CCCCTTTTTCTGGAGACTAAATAA-3' (SEQ ID NO:6)). FIG. 12 shows that pAC3-RSV-yCD2-IDO1miR30shRNA2 and pAC3-RSV-yCD2-PDL1miR30shRNA4 are stable in LN18 cells.

Example 8: Cloning and Characterization of pAC3-RSV-yCD2-U6-IDO1miR30shRNA2 and pAC3-RSV-yCD2-U6-PDL1miR30shRNA4

The replication competent retroviral vectors, pAC3-RSV-yCD2-U6-IDO1miR30shRNA2 and pAC3-RSV-yCD2-U6-PDL1miR30shRNA4, are derived from the backbone of pAC3-yCD2. The pAC3 backbone was isolated by endonuclease digestion of the pAC3-yCD2 plasmid DNA with Mlu I and Not I. The RSV-yCD2-U6-miR30shRNA cassette contains an RSV promoter and target-specific shRNA sequence targeting IDO1 and PDL1 (FIG. 5). Each RSV-yCD2-U6-miR30shRNA DNA fragment was synthesized with Mlu I and Not I restriction enzyme site present at each end of the DNA fragment for subsequent insertion at the corresponding site in the pAC3 backbone.

Vector stock was produced by transient transfection of the vector-encoding plasmid DNA into 293T cells using calcium phosphate method. Forty-eight hours post transfection, the supernatant containing the vector was collected and filtered through a 0.45 μm syringe filter and used immediately or stored in aliquots at −80° C. for later use. Titer values from these vectors were determined on PC3 cells by qPCR method using the primer set (5-MLV-U3-B: 5'-AGCCCACAACCCCTCACTC-3' (SEQ ID NO:2), 3-MLV-Psi: 5'-TCTCCCGATCCCGGACGA-3' (SEQ ID NO:3). Probe: FAM-5'-CCCCAAATGAAAGACCCCCGCTGACG-3'-BHQ1 (SEQ ID NO:4)). Twenty micro-liter of the collected vector stocks was used to infect human prostate cancer cells, PC3. Forty-eight hours post infection, genomic DNA of infected PC3 cells was extracted for titer assay. The titer of the vector stocks was determined by qPCR with an inclusion of standards of known copy numbers.

A MOI of 0.1 was used to infect LN18 cells which are known to express marked level of IDO1 and PDL1. The knockdown activity of miR30shRNA for each specific target gene is measured directly at the protein level. Approximately at day 14 post infection, cells infected with pAC3-RSV-yCD2-U6-miR30shRNA vectors were harvested for different assays, depends on the target gene of interest, to measure the shRNA knockdown activity.

Figure 15:
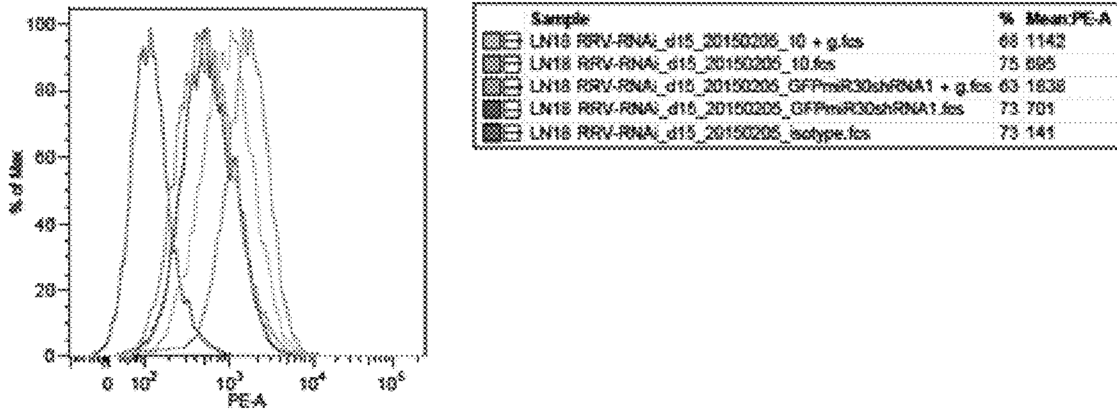
FIG. 15 shows knockdown of PDL1 cell surface expression by RRV-RSV-yCD2-U6-PDL1miR30shRNA.

LN18 cells infected with pAC3-RSV-yCD2-U6-IDO1miR30shRNA vectors were harvested for qualitative analysis of IDO1 expression level after IFNγ induction. FIG. 10 shows that pAC3-RSV-IDO1-U6-miR30shRNA2 has greater than 50% knockdown activity against IDO1 compares to that of uninfected cells. Likewise, LN18 cells infected with pAC3-RSV-yCD2-U6-PDL1miR30shRNA4 vector also showed approximately 40% knockdown activity (FIG. 15).

Figure 16A:
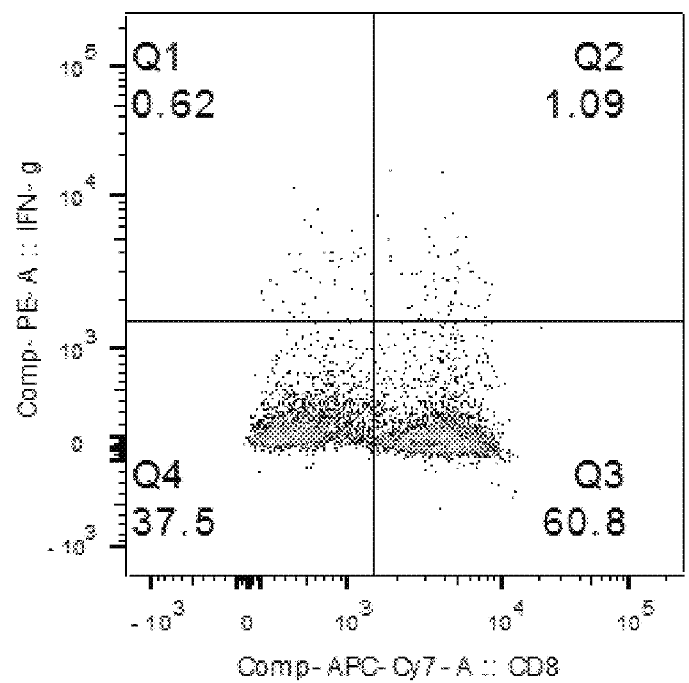
FIG. 16A-C shows FACS sort of TIL cells (IFNγ on the y-axis; CD8 on x-axis).
Figure 16B:
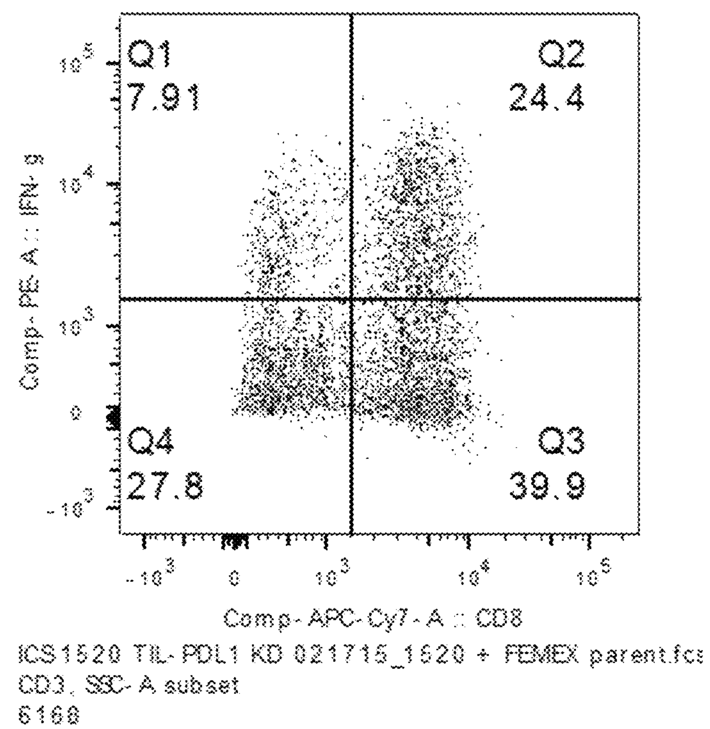

The vector stability of some pAC3-RSV-yCD2-U6-miR30shRNA vectors against IDO1 or PDL1 described above was evaluated by end-point PCR in infected LN18 cells. Cells infected with vectors at an MOI of 0.1 are passaged in culture for up to 21 days. Genomic DNA was extracted from infected cells followed by end point PCR using primer set spanning the 3' env and 3'UTR region (UCLA-5-127: 5'-CTGATCTTACTCTTTGGACCTTG-3' (SEQ ID NO:5); UCLA-3-37: 5'-CCCCTTTTTCTGGAGACTAAATAA-3' (SEQ ID NO:6)). FIG. 12 shows that pAC3-RSV-yCD2-U6-IDO1miR30shRNA2 and pAC3-RSV-yCD2-U6-PDL1miR30shRNA4 are stable in LN18 cells Example 9: Co-Cultivation of a TIL Line (1520 TIL) with a Target Cell Line (FEMX) Activates the T Cells and Leads to IFN-γ Production The immunological effects of modulating PD-L1 expression on tumor targets were investigated using a melanoma-based TIL (1520 TIL) reactive against FEMX melanoma cell line expressing the differentiation antigen gp100 (Voss et al., Immunol Res 45: 13-24, 2008). First, the TIL tumor system produced IFN-γ in a tumor-specific fashion as measured in a standard 12-hour intracellular cytokine release (ICS) assay. The data is shown in FIG. 16. 1% of the $CD3^{+}CD8^{+}$ TILs made IFN-γ when cultured alone (FIG. 16A-upper right quadrant) but greater than 24% of the $CD3^{+}CD8^{+}$ TILs made IFN when co-cultured with tumors (FIG. 16B-upper right quadrant).

Example 10: Blocking PD-L1 Increases the Frequency of Tumor-Specific CD8+ T Cells Making IFN-γ

Figure 16C:
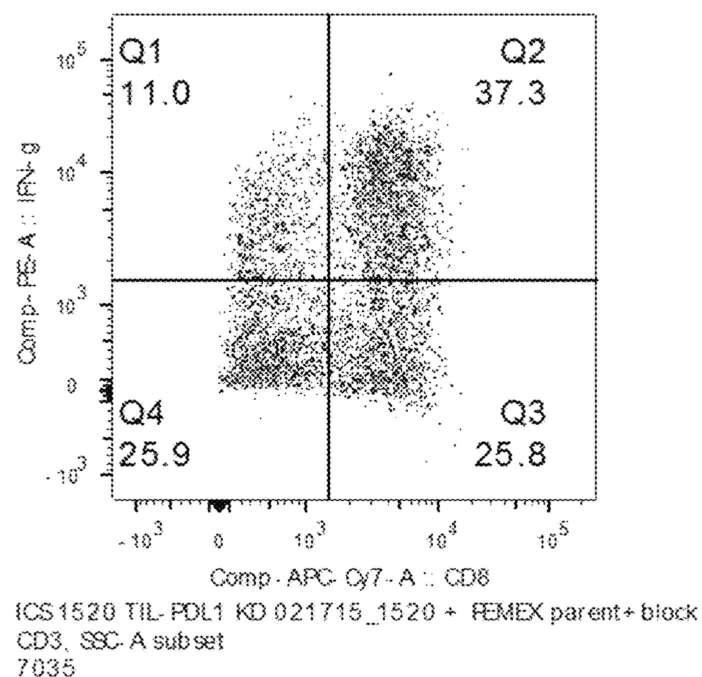
Figure 17:
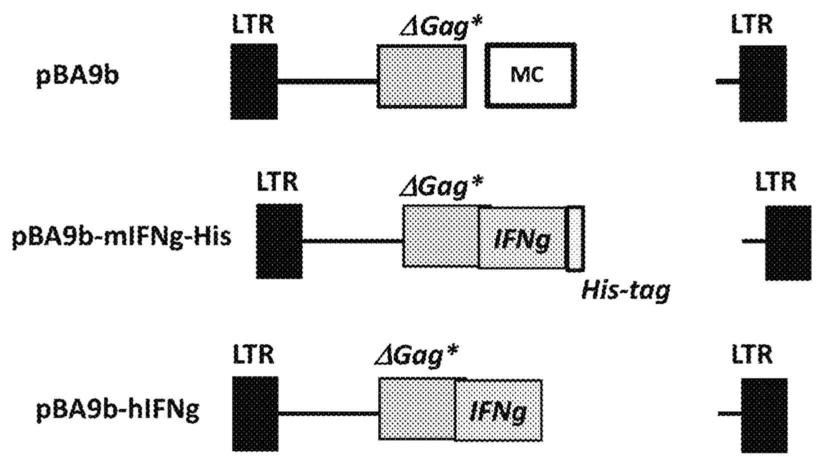
FIG. 17 shows a schematic diagram of pBA9b-IFNγ retroviral non-replicating vectors.

The Experiment in Example 9 also included an arm where 10 μg of a blocking anti-PD-L1 antibody (Biolegend clone 29E.2A3) was added to the FEMX tumors just before adding the TIL to the co-culture to a final concentration of 10 μg/mL. The results of this arm of the study showed that the PD-L1 blocking activity enhanced the fraction of T cells making IFN-gamma from 24.4% to 37.3% (FIG. 16C-upper right quadrant). Other immunological endpoints such as a CFSE proliferation assay or polychromatic flow cytometric-based phenotypic analysis can be used to confirm the effects of this perturbation of the PD-L1:PD-1 axis in the TIL system, and the result can be demonstrated in other T cell: tumor pairs.

Example 11: Knock Down of PD-L1 Gene Expression after Infection with an RRV-PDL1miR30shRNA FEMX cells were infected at a multiplicity of infection (MOI) of 0.1 with the RRV vector expressing the PD-L1shRNA shown in FIG. 20. The infection was allowed to proceed until the tumor cells were maximally infected and the cell surface expression of PD-L1 was measured by flow cytometry. The FEMX tumors transduced with RRV vector expressing the PD-L1shRNA demonstrating significant knock-down in the expression of PD-L1 compared to the parental and non-specific shRNA tumor lines.

Example 12: RRV-Mediated Down Regulation of PD-L1 in Tumor Targets Increases T Cell Recognition and Activation FEMX cells are treated as described in Example 3 and the experiment shown in Examples 1 and 2 repeated, with the target FEMX line in the RRV-anti-PD-L1 modulated and unmodulated forms. This modulation of PD-L1 expression, enhanced the tumor specific T-cell function at levels comparable to the blocking antibody as measured in our TIL system using the read out in Example 10. Other immunological endpoints such as a CFSE proliferation assay or polychromatic flow cytometric-based phenotypic analysis can be used to confirm the effects of this perturbation of the PD-L1:PD-1 axis in the TIL system, and the result can be demonstrated in other T cell: tumor pairs.

Example 13: Depletion of Tryptophan and Subsequent Production of Kynurenine Relates to the Quantity of IDO in Tumor Cells Depletion of the essential amino acid tryptophan from complete media while increasing the concentration of kynurenine (a toxic metabolite of tryptophan catabolism) occurs when culturing tumors that express high amounts of IDO. Expression levels of IDO in tumors can be modulated by stable transduced with a lentiviral vector expressing the IDO cDNA sequence (Origene). Parental, control (scrambled sequence) and IDO-overexpressing LN-18 (a human glioblastoma) are cultured with 500 U of IFN-γ for 72 hours and are assayed for the expression of IDO by western blot as well as the levels of tryptophan and kynurenine by ELISA (Rocky Mountain Diagnostic) The expression of IDO enzyme detected by Western strongly correlates with the increase of kynurenine and decrease of tryptophan as detected by ELISA.

Example 14: T Cells Co-Cultured with IDO+ Tumors are Anergized by the Lack of Tryptophan and High Amounts of Kynurenine Supernatants are isolated from 72 hour cultures of parental, control (scrambled sequence) and IDO-overexpressing LN-18 and are used as the culture media for peripheral blood mononuclear cells (PBMC) stimulation assays. CFSE-labeled (Thermo) PBMCs isolated from healthy donors are polyclonally stimulated with anti-CD3/CD28 beads (Milteny) overnight and three endpoints are used to measure the impact of kynurenine and tryptophan concentration on T-cell function: secretion of IFN-□ and TNF-a as measured by ELISA, proliferation of T cells as determined by the dilution of CFSE and cell surface expression levels of activation markers CD69, CD25 and CD71 on the flow cytometer (Critchley et al., PLoS Med., 4(5), 2007). Results from all three endpoints align which each other where PBMCs cultured in the supernatants from IDO-overexpressing LN-18 display relatively limited proliferation, cytokine release and expression of activation markers compared to PBMCs cultured in supernatant from parental or control LN-18.

Example 15: Knock Down of IDO Gene Expression after Infection with an RRV-IDO1miR30shRNA LN-18 cells were infected with an MOI of 0.1 using the RRV vector expressing the IDOshRNA shown in FIG. 20. The infection was allowed to proceed until the tumor cells were maximally infected and the expression of IDO was measured by western blot (Cell Signaling). The LN-18 tumors transduced with RRV vector expressing the IDOshRNA demonstrating significant knock-down in the expression of IDO-1 compared to the parental and non-specific shRNA tumor lines when treated with IFN-γ (FIGS. 6 and 10).

Example 16: Knock Down of IDO Gene Expression in Human Glioma with RRV Reduces IDO-Mediated T Cell Anergy Similar to the set of experiments in Example 14, supernatants are isolated from 72 hour cultures of parental, control (scrambled sequence) and IDO-overexpressing and IDO-knockdown LN-18 cell lines and are used as done above to measure the impact of kynurenine and tryptophan concentration on T-cell function. Similar to Example 14, PBMCs cultured in the supernatants from IDO-knockdown LN-18 display enhanced proliferation, cytokine release and expression of activation markers compared to PBMCs cultured in supernatant from parental or control LN-18 and especially the IDO-overexpressing LN-18 cells.

Example 17: Construction of pBA9b-IFNg Vectors pBA9b is derived from pBA-5b vector and has the same retroviral vector backbone sequence (Sheridan et al., 2000). It encodes MLV-based retroviral non-replicating vector containing an extended packaging region. The open reading frame of mouse (accession # BC119063) and human IFNγ (accession # BC070256) containing the Xho I and Not I restriction enzyme site at each end for directed cloning are codon optimized synthesized (IDT Inc). The synthesized fragments were cloned into pBA9b backbone at the corresponding restriction enzyme sites ("MC"). In mouse IFNg ORF, a His-tag was subsequently introduced to the C-terminus of the ORF by PCR. The resulting plasmid DNA were designated pBA9b-hIFNg and pBA9b-mIFNg. In both constructs, the IFNg expression is mediated by the viral LTR promoter (See FIG. 16).

Example 18: Virus Producer Cells Produce High Viral Titer and Functional IFNg Depending on Whether the Producer Line is from a Heterologous Species or not The vectors were first produced by transient transfection in 293GP producer cells. 293GP cells are derived from HEK293 cells stably producing MLV-based gag-pol. Vectors produced by transient transfection are pseudotyped with VSV-G envelope protein and subsequently transduce HA-L2 producer cells which stably express MLV-based gag-pol and 4070A amphotropic envelop protein. HA-L2 is a human packaging cell line constructed in the same way as the VPCL HA-LB (Sheridan et al., 2000) pBA9b-hIFNg and pBA9b-mIFNg vectors generated from stably transduced cells are titrated on human prostate PC-3 cells using qPCR method (5-MLV-U3-B: 5'-AGCCCACAACCCCTCACTC-3' (SEQ ID NO:2), 3-MLV-Psi: 5'-TCTCCCGATC CCGGACGA-3' (SEQ ID NO:3), probe: FAM-5'-CCCCAAATGAAAGACCCCCGCTGACG-3'-BHQ1 (SEQ ID NO:4)). The result showed that the titer values of pBA9b-hIFNg and pBA9b-mIFN produced by HA-L2 cells vary substantially (Table A). The titer of pBA9b-hIFNg is at least 2-log lower than pBA9b-mIFNg. However, when the vectors are produced in a dog cell line (DA-T1), the viral titer of pBA-hIFNg increased and was comparable that of pBA9b-mIFNg (Table B). DA-T1 is a dog packaging cell line constructed in the same way as the VPCL DA (Sheridan et al. 2000). Viral supernatant was also used to measure the IFNg expression by ELISA (R & D Systems). Table A and B show that substantial amount of mIFNg are produced by HAL2 and DA-T1 cells. DA-T1 cells transduced with pBA9b-hIFNg vector also produced high level of IFNg. In contrast, the low titer of pBA9b-hIFNg produced by HA-L2 cells correlated with low level of hIFNg production. The data suggest that human IFNg signaling interferes with the viral production and hIFNg production in human producer cells.

TABLE A

Viral titer and IFNg expression from HA-L2 transduced cells.

| | Titer (TU/mL) | IFNg (ng/mL) |
|---|---|---|
| HAL2-pBA9b | 3.51E+06 | — |
| HAL2-pBA9b-hIFNg | <2e4 | 0.3 |
| HAL2-pBA9b-mIFNg | 3.19E+06 | 41 |

TABLE B

Viral titer and IFNg expression from DA-T1 transduced cells.

| | Titer (TU/mL) | IFNg (ng/mL) |
|---|---|---|
| DAT1-pBA9b | 2.12E+06 | — |
| DAT1-pBA9b-hIFNg | 3.03E+06 | 20 |
| DAT1-pBA9b-mIFNg | 1.94E+06 | 96 |

Figure 18A:
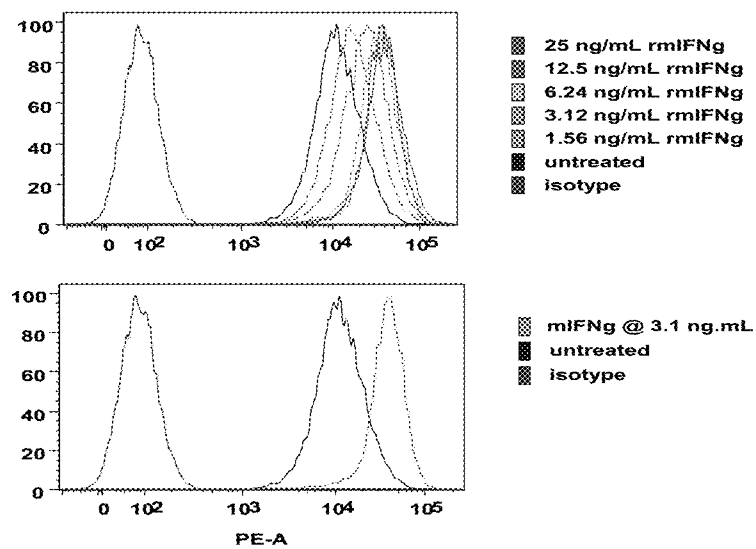
FIG. 18A shows mIFNg-induced MHC Class I upregulation in CT-26 cells.
Figure 18B:
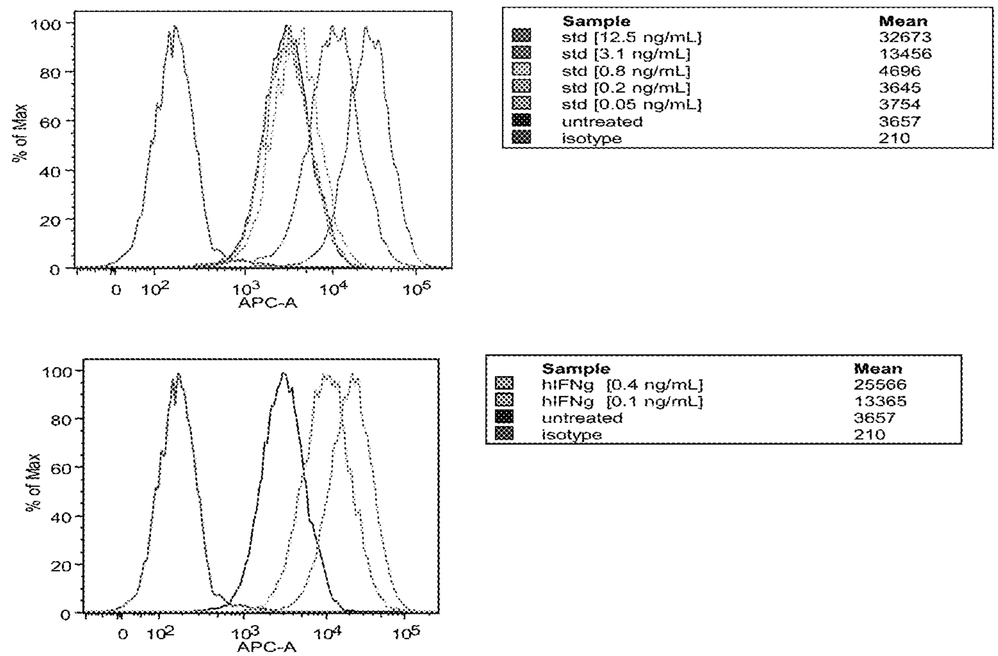
FIG. 18B shows hIFNg-induced MHC Class I upregulation in HT-1080 cells.

To verify the bioactivity of recombinant hIFNg and mIFNg produced from the virus producer cell, upregulation of MHC Class I cell surface expression by flow cytometry was performed. Supernatant of known IFNg concentration were incubated with species-matched mouse colon carcinoma cell line, CT-26 or human fibrosarcoma cell line, HT1080. The degree of upregulation measured by mean fluorescent intensity (MFI) was compared to a standard which are purified recombinant protein expressed from *E. coli*. FIG. 18A shows that recombinant mIFNg produced by the virus producer cells has bioactivity comparable to that of recombinant mIFNg produced by *E. coli*. Similarly, recombinant hIFNg produced by the virus producer cells also demonstrate bioactivity. The recombinant hIFNg produced from the virus producer cells are 3-5 fold higher than that produced from *E. coli* (FIG. 2B). The difference is likely due to the differences in amino acid composition as well as glycosylation pattern.

Example 19: Generation of Human IFNgR1-Knockout Virus Producer Cell Line

Recently developed technologies for genome editing include the use of zinc-finger nucleases (ZNFs), transcription activator-like effector nucleases (TALENs) and clustered, regularly interspaced palindromic repeat associated (CRISPR-Cas) proteins methods to generate targeted, permanent changes to genes of interest (Gaj et al., 2014, Bogdanove & Voytas, 2011; Jinek, et al., 2012; Shalem, et al., 2014; Wang, et al., 2014). In eukaryotic cells, the double stranded breaks introduced by ZNFs, TALENs and CRISPR-Cas are repaired by homologous recombination, which provides researchers options for more defined gene knockout. Using such methods, genome editing including deletion, insertional and single-base mutations can be introduced in site-specific defined region to achieve gene knockout. Among the 3 methods, CRISPR-Cas method was chosen to generate a genetic null allele by deletion.

Two single-guide RNA sequence are designed (GeneCopoeia) to knockout approximately 500 nts within the exon 3 region of human IFNgR1 subunit (accession # NG_007394) located in chromosome 6. The knockout is complemented by a donor DNA carrying a selection marker for positive selection. A pool of IFNgR1-modified cells containing either single allele, double or multiple allele knockout is further screened by clonal dilution. Approximately 50 clones are screened for complete knockout by PCR method. Three clones designated HAL2g1, HAL2g2 and HAL2g3 with complete IFNgR1-knockout gene are chosen and tested for their resistance to IFNg using the bioassay described above. The data indicate no upregulation of MHC Class I on cell surface compares to their basal expression level.

Example 20: IFNgR1-Knockout Virus Producer Cells Produce High Viral Titer and Functional hIFNg The pBA9b-hIFNg vector pseudotyped with VSV-G is first produced by transient transfection in 293GP producer cells and subsequently transduced into HA-L2g1, HA-L2g2 and HA-L2g3 producer cell lines. Supernatant collected from stably transduced cells are then titrated on human prostate PC-3 cells using qPCR method to determine viral titer. The data show all 3 clones produced similar level of titers and the titer value are comparable to or better than that produced by the DA-T1 cells. The level of hIFNg expression measured by ELISA also indicate amount similar to or greater than that produced by DA-T1 cells.

Example 21: In Vitro Positive Selection of pBA9b-hIFNg-yCD2 Transduced HA-L2g Cells Various genes can be used as positive selectable markers. These include: dyhdrofolate reductase (DHFR, Simonsen et al., Nuc Acid Res., 16: 2235-2246, 1988) with methotrexate in conjunction with a nucleotide transport inhibitor such as dipyridamole (Warlick et al. Biochemical Pharmacology, 59: 141-151, 2000) or nitrobenzylmercaptopurine riboside phosphate (Allay et al., Stem Cells, 16(suppl 1):223-233, 1998); Cytosine deaminase using N-(phosphonacetyl)-L-aspartate (PALA) to block de novo synthesis of uracil and anabolically downstream bases and cytosine to supply these through pyrimidine salvage pathways (Wahl et al., J Biol Chem., 254:8679 and Unger et al., Can. Gene Ther. 14:30-38); and various other selectable markers, obvious to those skilled in the art. In general higher levels of the selection agent select for better expression. The pBA9b-hIFNg-yCD2 vector encoding the yCD2 selectable marker leads to selection for the best expressing yCD2 in the presence of PALA cytosine and inosine. Presumably it can also lead to co-selection of clones that produce higher viral titer and higher level of hIFNg expression.

The concentration PALA required to kill HA-L2g cells transduced with pBA9b-hIFNg-yCD2 vector is determined. Cells are seeded at 1e3 cells in 96-well plates the day before. At 24 hour post cell seeding, PALA at 1, 10, 50 and 100 µM are added to the culture for 4 consecutive days followed MTS assay to determine the cell viability. The results show that cells are sensitive to PALA at 10 µM and plateau at 50 µM. A range of cytosine concentrations are also determined (0.2, 1, 5 10 mM) in culture by performing the same experiment described above. The data indicate that the cells can tolerate cytosine in all concentrations tested.

For positive in vitro selection, a pool of pBA9b-hIFNg transduced HA-L2g cells are seeded at 1e5 cells in T25 flask in the presence of 50 µM PALA and 10 mM cytosine and 4 mM inosine. One week after selection, clonal dilution is performed to isolate single cell clone for further selection. Twenty-five clones are then selected and expanded to measure their yCD2 expression by immunoblotting and IFNg expression by ELISA as well as viral titer. The data show that several clones express higher level of yCD2, hIFNg and produce higher titer compare to the pooled cells.

Figure 19:
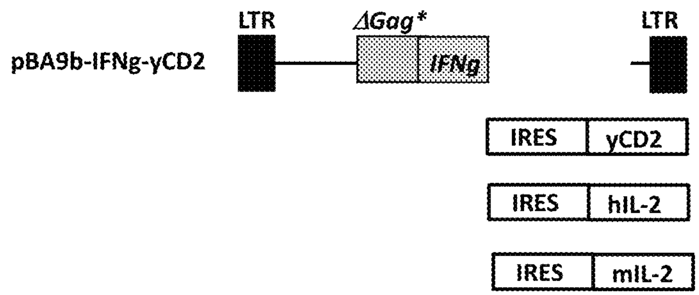
FIG. 19 shows a schematic diagram of pBA9b-IFNg-yCD2 and pBA9b-IL2 retroviral non-replicating vectors.

Example 22: Construction of pBA9b-IFNg-yCD2 Vectors and pBA9b-IL2 Vectors pBA9b-IFNg-yCD2 vectors are generated by subcloning of IRES-yCD2 DNA fragment into the pBA9b-hIFNg and pBA9b-mIFNg backbone. IRES-yCD2 DNA fragment is amplified by PCR using the pAC3-yCD2 vector as the template and the following primers: SalI-IRES-F: 5'-GTAC <u>GTCGAC</u>TACTGGCCGAAGCCGCTTGGA-3' (SEQ ID NO:17) and ClaI-yCD2-R: 5'-GTAC<u>ATCGAT</u>TT ACTCGCCGATATCCTCGAAC-3' (SEQ ID NO:18). The amplified PCR DNA fragment was gel purified and digested with Sal I and Cla I. The digested fragment was then subcloned into pBA9b-hIFNg and pBA9b-mIFNg backbone at the corresponding sites (FIG. 19).

Similarly, human IL-2 (accession # BC066257) and mouse IL-2 (accession # NM_008366) in pAC3 backbone are amplified using the following PCR primers: IRES-yCD2 DNA fragment is amplified by PCR using the pAC3-yCD2 vector as the template and the following primers: SalI-IRES-F: 5'-GTAC <u>GTCGAC</u>TACTGGCCGAAGCCGCTTGGA-3' (SEQ ID NO:17), ClaI-hIL-2-R: 5'-GTAC <u>ATCGAT</u>TCAAGTCAGTGTTGAGATGATG-3' (SEQ ID NO:19) and ClaI-mIL-2-R: 5'-GTAC <u>ATCGAT</u>TTATTGAGGGCTTGTTGAGATG-3' (SEQ ID NO:20). The amplified PCR DNA fragment was gel purified and digested with Sal I and Cla I. The digested fragment was then subcloned into pBA9b-hIFNg and pBA9b-mIFNg backbone at the corresponding sites (FIG. 19).

Example 23: Virus Producer Cells Produce Relative High Viral Titer, CD Expression and Functional IL-2

The VSV-G psueodypted vectors are first produced by transient transfection in 293GP producer cells and subsequently transduce HA-L2 cells. pBA9b-hIFNg-yCD2 and pBA9b-mIFNg-ycD2 vectors generated from stably transduced HA-L2 cells are titrated on human prostate PC-3 cells using qPCR. Viral supernatant is also used to measure amount of IL-2 expression by ELISA (R & D Systems). The result showed titer values similar to that of pBA9b-hIFNg and pBA9b-mIFNg produced by HA-L2g and HA-L2 cells, respectively.

To measure the bioactivity of recombinant hIL-2 and mIL-2 produced from the HA-L2 cells, cell proliferation assay is performed using a murine cytotoxic T-cell line derived from C57/Bl/6 mouse strain, CTLL-2, which constitutively express IL-2 receptors. CTLL-2 cell growth depends greatly on the presence of IL-2. The bioactivity of IL-2 is determined by the level of $^{3}$H-thymidine incorporation into the DNA of proliferating cells. Due to >60% homology between mouse and human IL-2, the cell line responds to both hIL-2 and mIL-2 in a dose dependent manner in the concentration range of approximately 50 pg/mL to 50 ng/mL. The data show that both recombinant hIL-2 and mIL-2 produced by the HA-L2 cells have bioactivity comparable to that of recombinant hIL-2 and mIL-2 produced by *E. coli*. In addition, the level of CD expression from pBA9b-IFNg-yCD2 transduced HA-L2 cells is also detected by immunoblotting using an antibody against CD.

Example 24: Construction of pBA9b-IFNg-miR30shRNA and pBA9b-IFNg-shRNA Vectors

Figure 20A:
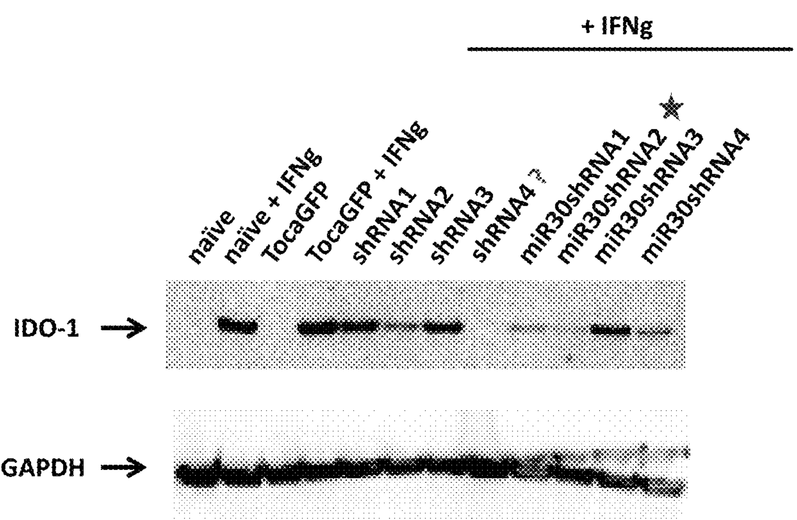
FIG. 20A shows bioactivity of shRNA targeted to IDO-1 in RRV-shRNA infected cells.
Figure 20B:
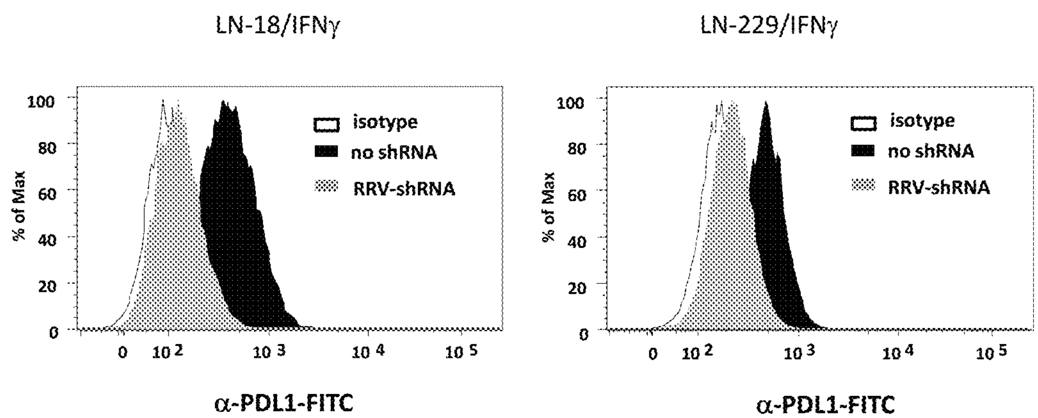
FIG. 20B shows bioactivity of shRNA targeted to PDL-1 in RRV-shRNA infected cells.
Figure 20C:
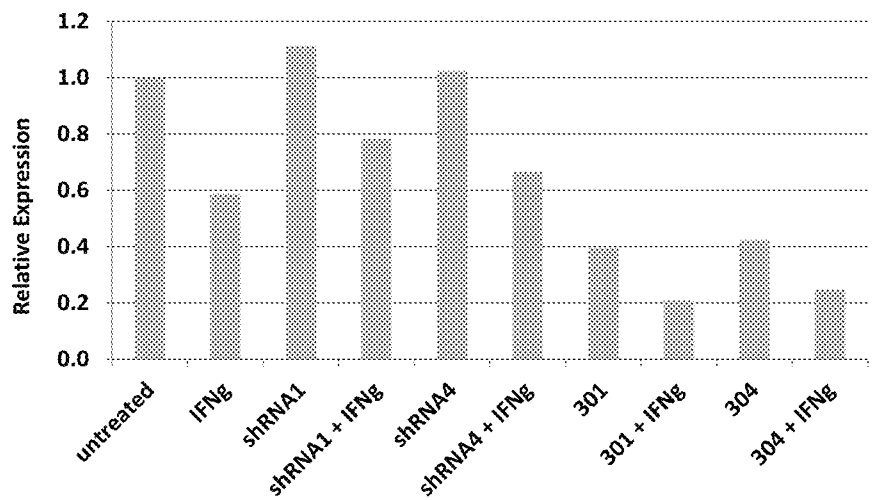
FIG. 20C shows bioactivity of shRNA targeted to TGF-β2 in RRV-shRNA infected cells.

Many cancers express or secrete a number of immunosuppressive molecules, including HLA G, IDO, FasL, PDL-1 and TGF-β 1, 2 and 3, in order to escape the anti-tumor immune responses (Jackson et al., 2011, Avril et al., 2010). These molecules suppress T cell proliferation, inhibit T cell activation and differentiation into cytotoxic effector cells, or trigger T cells apoptosis. FIG. 20A-C shows preliminary proof of principle for RRV as a delivery vehicle for these types of molecules in vitro. Design of a multimodal configurations containing IFNg and shRNA targeted to PDL-1, IDO and TGF-3 in retroviral non-replicating vector is presented here as a combination immunotherapy.

pBA9b-IFNg-shRNA vectors are generated by subcloning of DNA fragment into the pBA9b-hIFNg and pBA9b-mIFNg backone at the Not I restriction enzyme site. U6-shRNA DNA fragments are amplified by PCR using the pAC3-shRNA vectors as the templates and the following universal primers with Not I restriction enzyme site at the end (Table C).

TABLE C universal primers for amplifying U6-shRNA and U6-miR30shRNA cassettes.

| Primer name | Primer sequence | Priming site |
|---|---|---|
| hU6-Not I-F | 5'-GATCGCGGCCGCACGCGTAAGGTCG GGCAGGAA-3' (SEQ ID NO: 21) | U6 |
| shRNA-Not I-R | 5'-ATCTGCGGCCGCCTAGAAAAAA-3' (SEQ ID NO: 22) | downstream of shRNA |
| miR30-Not I-R | GCGGCCGCCGCATTAGTCTTCCAATTG (SEQ ID NO: 23) | Downstream of miR30shRNA |

Figure 21:
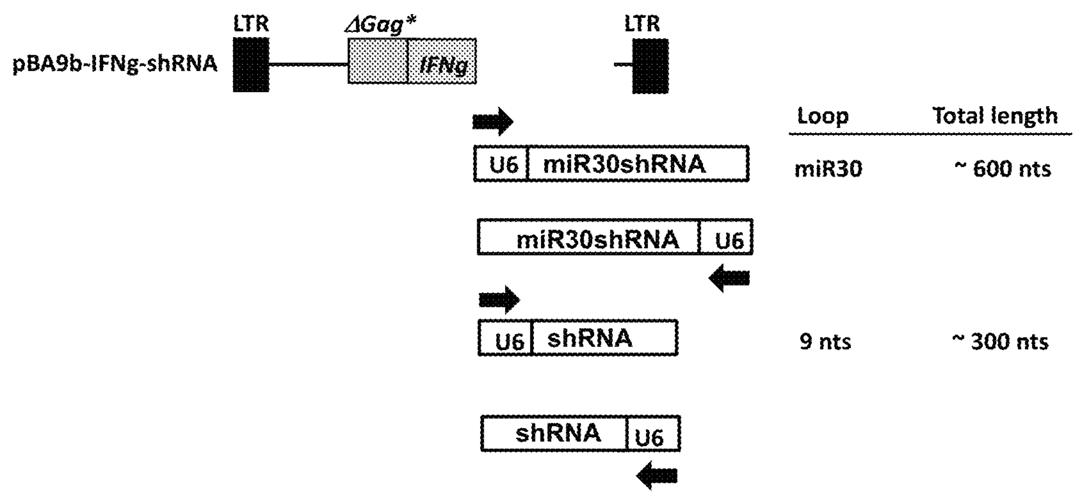
FIG. 21 shows a schematic diagram of pBA9b-IFNg-shRNA retroviral non-replicating vectors.

U6-shRNA and U6-miR30shRNA cassettes targeting murine IDO1, PDL-1 and TGF-β are cloned into the pBA9b-mIFNg backbone. Likewise, U6-shRNA and U6-miR30shRNA cassettes targeting human IDO1, PDL-1 and TGF-β are cloned into the pBA9b-hIFNg backbone. Vectors with both forward and reversed orientation relative to the 5' LTR are generated (FIG. 21).

Example 25: Virus Producer Cells Produce High Viral Titer and Functional IFNg

The VSV-G pseudotyped vectors are first produced by transient transfection in 293GP producer cells and subsequently transduce HA-L2 or HA-L2g cells pBA9b-mIFNg-shRNA vectors generated from stably transduced HA-L2 or HA-L2g cells are titrated on human prostate PC-3 cells using qPCR. Viral supernatant is also used to measure amount of IFNg expression by ELISA (R & D Systems). The result show titer values similar to that of pBA9b-hIFNg and pBA9b-mIFNg produced by HA-L2g and HA-L2 cells, respectively.

The bioactivity of human IFNg is performed as described. The bioactivity of shRNA targeted to human IDO1, PDL-1 and TGF-β2, is performed by transducing human glioma cell line LN-18, which expresses high level of IDO1, PDL-1 and TGFb2, at MOI of 10-20. One week after transduction, the knockdown activity of shRNA in transduced cells is confirmed by assessing protein expression of IDO1, PDL-1 and TGF-β2 by immunoblotting, flow cytometry or ELISA.

The bioactivity of mouse IFNg is performed as described. The bioactivity of shRNA targeted to mouse IDO1, PDL-1 and TGF-β2, is performed by transducing murine tumor cell lines which expresses high level of IDO1, PDL-1 and TGF-β2, at MOI of 10-20. One week after transduction, the knockdown activity of shRNA in transduced cells is confirmed by assessing protein expression of IDO1, PDL-1 and TGF-β2 by immunoblotting, flow cytometry or ELISA.

Tables D-H as set forth in the provisional application (U.S. Patent Application No. 61/970,823) provide RNAi sequences that can be used to promote immune-stimulating. Tables E-H from the provisional application are incorporated herein by reference and demonstrate other sequences that can be inserted downstream of a polIII or RSV promoter in a vector of the disclosure. One of skill in the art can readily identify and make use of the sequences disclosed in Tables E-H.

TABLE D siRNA sequences targeting mouse IDO1, PDL1 and TGFb2

| target | Accession # | Antisense seq (SEQ ID NOs) | Predicted percentage of mRNA remained in cells after siRNA directed cleavage |
|---|---|---|---|
| IDO-1 | NM 008324 | TATTCTATAGTCTTACTTG (24) | 8 |
| | | TCAACTTCTTCTCGAAGCT (25) | 24 |
| | | TGAAATGACAAACTCACGG (26) | 11 |
| PDL-1 | NM_021893/ | TAGTTCATGCTCAGAAGTG (27) | 12 |
| | | AATGCTAGACAATGAACTG (28) | 18 |
| | | TATGCAGCAGTAAACGCCT (29) | 18 |
| | | AGTCCGCACCACCGTAGCT (30) | 43 |
| TGF-beta2 | NM_009367 | TTGTGGTGAAGCCACTCCT (31) | 16 |
| | | TCTCCTGCAGTAAGTCCCT (32) | 36 |
| | | AACAAACAGAACACAAGCT (33) | 22 |

Example 26: Anti-Melanoma Efficacy Studies with Mouse IFN Gamma Expressing Vectors in a Mouse Subcutaneous Melanoma Model The objective of this study is to assess the effect of a retroviral non-replicating vector (RNV) carrying the mouse IFN gamma gene and a modified yeast cytosine deaminase (CD) gene (Perez et al., Mol. Ther., 2012) delivered via intratumoral (IT) injection in DBA/2 mice bearing subcutaneous melanoma (Cloudman S91).

Female DBA/2 mice (age ~8 weeks) are purchased from Jackson Laboratories (Bar Harbor, Me.). Mice are acclimated for 7 days after arrival before start of studies.

Cloudman S91 cells (ATCC, Manassas Va.) are a spontaneously arising melanoma derived from DBA/2 mice. Cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. S91 cells (1E6 in 100 μL) are injected into the right flank of DBA/2 mice.

Vectors preparations are made by transient transfection of the vector plasmid with an amphotropic envelope expressing plasmid on a 293gag pol line (Burns et al., PNAS 90:8833-8037, 1993); alternatively a producer cell line (either clonal or a pool) based on a human HT1080 based amphotropic MLV packaging cell line or the dog D-17 based amphotropic packaging cell line with titers of approximately 10E6TU/ml or greater. For initial studies vector is not further purified or concentrated. For follow-on experiments to determine full dose response curves, high titer purified material is prepared with a titer expected around 1-5×10E8/ml. Vector is administered IT in a volume of 5-100 μL and IV in 100 μL in portions for 1 to 7 days, and the total dose/mouse between approximately 4×10E4-2.5×10E8 TU/mouse.

High titer purified retroviral vector preparations were prepared from cells grown in Corning® CellSTACK® Cell Culture Chambers or equivalent. Cells were grown at 37° C. in DMEM high glucose (Irvine Scientifics, Irvine, Calif.) supplemented with 10% fetal bovine serum (FBS), and allowed to expand for several days. Supernatants were harvested, clarified by filtration, treated with nucleases and further purified and concentrated by ion exchange columns and by size-exclusion column chromatography. Concentrated vector was stabilized and formulated in a suitable formulation buffer (e.g. 20 mM Tris, 100 mM NaCl, 10 mg/mL sucrose, and 10 mg/mL mannitol, pH 7.4). Formulation buffers may also include a protein component such as Fetal Bovine Serum or Human Serum Albumin.

The titers of vector preparations used in the in vivo studies were 2-5×10E8 TU/ml. Vector was stored frozen at −80"C and quick-thawed just prior to injection.

Five groups of female DBA/2 (55 mice, 9-10 weeks of age) are implanted subcutaneously with S91 melanoma cells (Day 0) and then dosed (day 4-10) depending on growth rate of the S91 tumor; approximately 50-100=$^3$) with vehicle (Groups 1), with control vector [pBA-9b or pBA-9b-CD vector], (Group2), intratumor (IT) (CD-IFN gamma vector injection (Groups 3), or intravenous CD-IFN gamma vector injection (group 4). Groups 3 and 4 were further divided into groups 3a and 4a that were not treated with 5-fluorocytosine (5-FC), and groups 3b and 4b that were.

Vector is injected at increasing doses from 10E4 to 5×10E8, both by changing the concentration of vector and by increasing the number of days of administration. This is performed for both the IT and IV groups. This strategy allows comparison of relative efficacy of different therapeutic strategies across a wide range of vector doses. In the 5-FC groups 5-FC is delivered IP 2 x/day at 500 mg/kg for 5 days from starting at 3-10 days after vector administration.

Tumor growth analysis is carried out to 2000 mm$^3$ or to 60 days based on whichever comes first. 10 mice from each group will be plotted for tumor size over time. Statistical significance will be determined using analysis of variance (ANOVA). P values of <0.05 are considered statistically significant in all analyses, which are performed with Prism 5 statistical software (GraphPad Software) or equivalent. In-life observations are also taken to assess any adverse events to IFN gamma expression during treatment.

Delivery of IFN gamma by RNV intratumorally shows a statistically significant retardation of growth compared to the controls that is also dependent on dose. Delivery of IFN gamma by RNV intravenously shows a statistically significant retardation of growth compared to the controls treated with control expressing CD alone or empty vector, and mitigates melanoma burden from the DBA/2-Cloudman S91 mouse melanoma model. Delivery of IFN gamm-CD vector followed by 5-FC administration shows increase efficacy compared to those groups treated with the same vector and without 5-FC treatment.

Example 27: Anti-Tumor Efficacy Studies with Mouse IFN Gamma Expressing Vectors in a Mouse Melanoma and Colorectal Models, with Subcutaneous and Disseminate Tumor Six- to 8-week-old female BALB/c and C57BL/6 mice are purchased from Harlan Sprague-Dawley (Indianapolis, Ind.), housed in autoclaved microisolator cages containing sterile bedding, and given irradiated food and acidified water ad libitum.

CT26, a murine colorectal carcinoma line of BALB/c origin (Corbett et al., 1915) and B16F10, a spontaneous murine melanoma cell line of C57BL/6 origin are cultured in Dulbecco's modified Eagle's medium (DMEM) plus 10% fetal bovine serum supplemented with 2 mM glutamine, I mM sodium pyruvate, 100 microM nonessential amino acids, and 18 mM HEPES buffer. Cells are grown in vitro under standard tissue culture conditions, and maintained in log phase prior to inoculation.

Tumor cells are maintained in log-phase growth and are harvested with trypsin-EDTA, washed, and resuspended in Hanks' basal salt solution immediately prior to inoculation of animals. For the formation of subcutaneous tumors, B16F10 cells are injected at $1\times10^5$ cells/mouse in 0.1 ml in the ventral abdominal region of C57BL/6 mice. CT26 cells are injected at $2\times10^5$ cells/mouse in 0.1 ml in the ventral abdominal region of BALB/c mice. When the tumors grow to volumes of 25-40 mm$^3$, the animals are redistributed to obtain similar average starting tumor volumes in each treatment group of 7-10 mice. A single course of therapy consisted of 50 microL of formulation buffer, control vector, or therapeutic vector injected intratumorally once per day for 1-7 days. Tumors are measured every 3-4 days and volume is calculated according to the following equation: volume=length x width x height x n16. Statistical significance between treatment groups is determined using analysis of variance (ANOVA).

To model disseminated disease, animals are inoculated concurrently with $2\times10^5$ unmodified tumor cells subcutaneously (as described above) and with $1\times10^4$ or $1\times10^5$ cells intravenously per mouse, to seed the lungs. Subcutaneous tumor size is monitored twice a week until tumor volumes in the untreated or buffer treated groups reach sizes>1500 mm$^3$. Mice are then sacrificed and lungs are either weighed to determine tumor burden and/or visually examined to record the number of tumor cell foci. Values for tumor volumes and pulmonary tumor foci are reported as average+ SEM unless indicated otherwise. Differences among the treatment groups are investigated using ANOVA. Correlation between tumor volume and lung weight is examined using Spearman's rho test.

Vector is injected at increasing doses from 10E4 to 5×10E8, both by changing the concentration of vector and by increasing the number of days of administration. This is performed for both IT and IV routes of administration. This strategy allows comparison of relative efficacy of the different vector strategies across a wide range of vector doses. Groups treated with 5-FC are treated with a schedule similar to that in example 26.

Delivery of IFN gamma by RNV intratumorally shows a statistically significant retardation of growth compared to the controls that is also dependent on dose. Delivery of IFN gamma by RNV intravenously shows a statistically significant retardation of growth compared to the controls treated with control expressing CD alone or empty vector, and mitigates melanoma burden from the B16 and CT26mouse melanoma model. Delivery of IFN gamma-CD vector followed by 5-FC administration shows increased efficacy compared to those groups treated with the same vector without 5-FC treatment, in the SQ tumor and also the disseminated tumor model. Treatment with IFN gamma-miRPDL1 showed increased efficacy compared to IFN-gamma vector alone in the SQ tumor models and the disseminated tumor models.

These methods (in examples 26 and 27) can be used to determine the relative potency of any set of viral vector, with or without the IFNgamma gene, and the results extrapolated to human use with the species homologous sequences for IFNgamma, siRNA constructs and the like.

Example 28: Dosing of Patients with RRV Encoding an siRNA or a Single-Chain Antibody that Down Regulates an Immune Inhibitory Function in a Cell or Tissue Patients with newly diagnosed stage 3 or 4 malignant glioma are enrolled and vector is administered by administration into the resection cavity using vector in the range of 10^6 to 10^11TU, depending on the patient and on the value delivered at the time of resection. Standard of care for GBM in USA calls for resection followed about 6 weeks later with Temozolomide and radiation (Stupp et al., NEJM, 352:987-996, 2005), so 5-FC is administered in conjunction with TMZ and or radiation treatment, 4-6 weeks later. Mouse studies have shown that RRV-CD vectors with 5-FC is at least additive to Temozolomide and radiation. Patient outcomes are measured by response rates from MRI scans, progression-free survival, overall survival or other accepted marker, and show a significant advantage over the standard of care.

A number of embodiments of the disclosure been described. Nevertheless, it will be understood that various modifications may be made without departing from the spirit and scope of the disclosure. Accordingly, other embodiments are within the scope of the following claims.

What is claimed is:

1. A recombinant replication competent retroviral vector comprising a sequence encoding at least one agent that down regulates an immune inhibitory agent, wherein the at least one agent is a sequence encoding an antibody to a programmed death ligand (PDL) wherein the replication competent retroviral vector has a genome of the general structure from 5' to 3' comprising a long terminal repeat (LTR)-gag sequence-pol sequence-env sequence-at least one expression cassette-LTR, wherein said recombinant retroviral vector comprises a first cassette comprising a polIII promoter operably linked to a first inhibitory nucleic acid sequence, and a second cassette comprising a mini-promoter operably linked to the sequence encoding the antibody to the PDL.

2. The recombinant retroviral vector of claim 1, wherein the vector comprises a second sequence encoding at least one agent that down regulates an immune inhibitory agent.

3. The recombinant retroviral vector of claim 1, wherein the antibody is a single-chain antibody and the first inhibitory nucleic acid sequence is a miRNA encoding sequence.

4. The recombinant retroviral vector of claim 1, wherein the vector further comprises a polynucleotide encoding a polypeptide having cytosine deaminase activity.

5. The retroviral vector of claim 1, wherein the vector further comprises a third agent selected from the group consisting of (i) a polynucleotide encoding a polypeptide that converts a prodrug to a cytotoxic drug, and (ii) a polynucleotide encoding a cytokine or chemokine.

6. The recombinant retroviral vector of claim 1, wherein the vector comprises a retroviral polynucleotide sequence engineered from murine leukemia virus (MLV), Moloney murine leukemia virus (MoMLV), Feline leukemia virus (FeLV) or Gibbon ape leukemia virus (GALV).

7. The recombinant retroviral vector of claim 6, wherein the MLV is an amphotropic MLV.

8. The recombinant retroviral vector of claim 1, where the vector comprises:

a retroviral GAG protein;

a retroviral POL protein;

a retroviral envelope:

a retroviral polynucleotide comprising:

LTR sequences at the 3' end of the retroviral polynucleotide sequence;

a promoter sequence at the 5' end of the retroviral polynucleotide sequence, said promoter being suitable for expression in a mammalian cell, a gag nucleic acid domain;

a pol nucleic acid domain; and an env nucleic acid domain;

Wherein the first cassette and the second cassette are positioned 5' of the 3' LTR and 3' to the env nucleic acid domain; and cis-acting sequences necessary for reverse transcription, packaging, and integration in a target cell.

9. The recombinant retroviral vector of claim 8, wherein the env domain encodes an amphotropic env protein.

10. The recombinant retroviral vector of claim 1, wherein the second cassette comprises an RSV promoter operably linked to the sequence encoding the antibody.

11. The recombinant retroviral vector of claim 1, wherein the polIII promoter comprises an H1 or U6.

* * * * *